United States Patent [19]
Ivy et al.

[11] Patent Number: 6,165,477
[45] Date of Patent: Dec. 26, 2000

[54] SUBUNIT IMMONOGENIC COMPOSITION AGAINST DENGUE INFECTION

[75] Inventors: John Ivy, Kailua; Eilen Nakano, Hon.; David Clements, Honolulu, all of Hi.

[73] Assignee: Hawaii Biotechnology Group, Inc., Aiea, Hi.

[21] Appl. No.: 08/915,152

[22] Filed: Aug. 20, 1997

Related U.S. Application Data

[63] Continuation of application No. 08/500,469, Jul. 10, 1995, abandoned, which is a continuation-in-part of application No. 08/488,807, Jun. 7, 1995, abandoned, which is a continuation-in-part of application No. 08/448,734, May 24, 1995, abandoned.

[51] Int. Cl.$^7$ .................................................. A61K 39/193
[52] U.S. Cl. .................................... 424/218.1; 424/184.1; 424/186.1; 435/69.3; 435/70.1
[58] Field of Search .............................. 424/218.1, 202.1; 536/27.72; 435/5; 530/300, 350; 475/69.1, 257.3

[56] References Cited

U.S. PATENT DOCUMENTS

| | | | |
|---|---|---|---|
| 5,494,671 | 2/1996 | Lai et al. ............................... | 424/218.1 |
| 5,514,375 | 5/1996 | Paoletti et al. ........................ | 424/199.1 |

FOREIGN PATENT DOCUMENTS

| | | |
|---|---|---|
| 9202548 | of 0000 | WIPO . |
| 9203545 | of 0000 | WIPO . |

OTHER PUBLICATIONS

Harlow, E., et al., 1988, "Immunizations", in *Antibodies: A Laboratory Manual*, Harlow, E., et al., eds., Cold Spring Harbor Laboratory, Cold Spring Harbor, New York, pp. 53–137.

Monath et al., "Flaviviruses," in Fields Virology, Third Edition, Fields et al., eds., Lippincott–Raven Publishers, Philadelphia, pp. 961–977 and 1002–1004, 1996.

Schlesinger et al., "New approaches to flavivirus vaccine development," Biotech. 20:289–307, 1992.

(List continued on next page.)

*Primary Examiner*—Laurie Scheiner
*Assistant Examiner*—Jeffrey S. Parkin
*Attorney, Agent, or Firm*—Morrison & Foerster LLP

[57] ABSTRACT

The Flaviviridae comprise a number of medically important pathogens that cause significant morbidity in humans including the dengue (DEN) virus, Japanese encephalitis (JE) virus, tick-borne encephalitis virus (TBE), and yellow fever virus (YF). Flaviviruses are generally transmitted to vertebrates by chronically infected mosquito or tick vectors. The viral particle which is enveloped by host cell membranes, comprises a single positive strand genomic RNA and the structural capsid (CA), membrane (M), and envelope (E) proteins. The E and M proteins are found on the surface of the virion where they are anchored in the membrane. Mature E is glycosylated and contains functional domains responsible for cell surface attachment and intraendosomal fusion activities. Problems have arisen in the art with respect to producing recombinant forms of the E glycoprotein that retain their native configuration and attendant properties associated therewith (i.e., ability to induce neutralizing antibody responses). To date, recombinantly produced E glycoproteins have suffered from a number of limitations including improper glycosylation, folding, and disulfide bond formation. The claimed invention has addressed these concerns by providing secreted recombinant forms of the E glycoprotein that are highly immunogenic and appear to retain their native configuration. Carboxy-terminally truncated forms of E containing the amino terminal 395 amino acids and a suitable secretion signal sequence were generated in *Drosophila melanogaster* Schneider cell lines. Immunogenic compositions comprising these recombinant envelope glycoproteins were capable of inducing protective, neutralizing antibody responses when administered to a suitable host.

13 Claims, 19 Drawing Sheets

OTHER PUBLICATIONS

Stephenson, J., "Flavivirus vaccines," Vaccine 6:471–480, 1988.

Rico–Hesse et al., "Molecular evolution of dengue type 2 virus in thailand," Am. J. Trop. Med. Hyg. 58(1):96–101, 1998.

Igarashi, A., "Impact of dengue virus infection and its control," FEMS Immunol. Med. Microbiol. 18:291–300, 1997.

Bancroft, W., "Current status of dengue vaccines and prospects for the future," PRHSJ 6(1):23–26, 1987.

Culp et al., "Regulated expression allows high level production and secretion of HIV–1 gp120 envelope glycoprotein in drosophila schneider cells," Biotech. 9:173–177, 1991.

de Oliveira et al., "Immunogenicity of an alum–adsorbed synthetic multiple–antigen peptide based on B–and T–cell epitopes of the Plasmodium falciparum CS protein: possible vaccine application," Vaccine 12(11):1012–1017, 1994.

Delenda et al., "Protective efficacy in mice of a secreted form of recombinant dengue–2 virus envelope protein produced in baculovirus infected insect cells," Arch. Virol. 139(1–2):197–207, 1994(a).

Delenda et al., "Analysis of C–terminally truncated dengue 2 and dengue 3 virus envelope glycoproteins: processing in insect cells and immunogenic properties in mice," J. Gen. Virol. 75:1569–1578, 1994(b).

Nowak, T. and Wengler, G., "Analysis of Disulfides Present in the Membrane Proteins of the West Nile Flavivirus," *Virology* (1987) 156:127–137.

Putnak, R.A.,"Progress in the Development of Recombinant Vaccines Against Dengue and Other Arthopod–borne Flaviviruses," *Modern Vaccinology*, E. Kurstak, ed. New York: Plenum Medical, 1994, chapter 11, 231–252.

Roehrig et al., "Mapping of Biologically Active Helper T–cell Epitopes on the Flavivirus Envelope Glycoprotein," *Vaccines* 92, Cold Spring Harbor Laboratory Press, 1992, p. 277–281.

Srivastava, A.K. et al., "Immunogenicity of Peptides Cleaved by Cyanogen Bromide from Japanese Encephalitis Virus Envelope Glycoprotein E," *Acta Virol* (1990) 34:228–238.

Srivastava, A.K. et al., "Japanese Encephalitis Virus Fusion Protein with Protein A Expressed in *Escherichia coli* Confers Protective Immunity in Mice," *Microbiol Immunol* (1991) 35:863–870.

Trirawatanapong, T. et al., "Mapping of a region of dengue virus type–2 glycoprotein required for binding by a neutralizing monoclonal antibody," *Gene* (1992) 116:139–150.

Brandt, E.E., "Development of Dengue and Japanese Encephilitis Vaccines,"*J. Infect Disease* (1990) 162:577–583.

Chambers, T.J. et al., "Flavivirus Genome Organization, Expression and Replication," *Annual Rev Microbiol* (1990) 44:649–688.

Hahn, Y.S. et al., "Nucleotide Sequence of Dengue 2 RNA and Comparison of the Encoded Proteins with Those of Other Flaviviruses," *Virology* (1988) 162:167–180.

Halstead, S.B., "Pathogenesis of Dengue: Challenges to Molecular Biology," *Science* (1988) 239:476–481.

Henchal, E.A. and Putnak, J.R., "The Dengue Viruses," *Clin Microbiol Rev.* (1990) 3:376–396.

Jan, L., et al., "Increased Immunogenicity and Protective Efficacy in Outbread and Inbread Mice by Strategic Carboxyl–Terminal Truncation of Japanese Encephalitis Virus Envelope Glycoprotein," *Am. J. Trop. Med. Hyg.*, 48(3), (1993) pp. 412–423.

Mandl, C.W. et al., "Antigenic Structure of the Flavivirus Envelope Protein E at the Molecular Level, Using Tick–Borne Encephalitis Virus as a Model," *Virology* (1989) 63:564–571.

Mason, P.W. et al., "The antigenic structure of dengue type 1 virus envelope and NS1 proteins expressed in *Escherichia coli*," *J. Gen. Virol* (1990) 71:2107–2114.

Mason, P.W., et al., "Molecular Characterization of a Neutralizing Domain of the Japanese Encephalitis Virus Structural Glycoprotein," *J. Gen Virol* (1989) 70:2037–2048.

Megret, F. et al., "Use of Recombinant Fusion Proteins and Monoclonal Antibodies to Define Linear and Discontinuous Antigenic Sites on the Dengue Virus Envelope Gylcoprotein," *Virlogy* (1992) 187:480–491.

Men, R. et al., "Carboxy–Terminally Truncated Dengue Virus Envelope Glycoproteins Expressed on the Cell Surface and Secreted Extracellularly Exhibit Increased Immunogenicity in Mice," *J. Virol* (1991) 65:1400–1407.

Winkler, G. et al., "Characterization of a Disulphide Bridge–stabilized Antigenic Domain of Tick–borne Encephalitis Virus Structural Glycoprotein," *J. Gen Virol* (1987) 68:2239–2244.

Control of Virus Disease, Second Edition 1993.

FIG.1

Capsid
|  *
97       ATGA ATAACCAACG GAAAAAGGCG AGAAACACGC CTTTCAATAT
141 GCTGAAACGC GAGAGAAACC GCGTGTCAAC TGTACAACAG TTGACAAAGA
191 GATTCTCACT TGGAATGCTG CAGGGACGAG GACCACTAAA ATTGTTCATG
241 GCCCTGGTGG CATTCCTTCG TTTCCTAACA ATCCCACCAA CAGCAGGGAT
291 ATTAAAAAGA TGGGGAACAA TTAAAAAATC AAAGGCTATT AATGTTCTGA
341 GAGGCTTCAG GAAAGAGATT GGAAGGATGC TGAATATCTT AAACAGGAGA preMembrane
|
391 CGTAGAACTG CAGGCATGAT CATCATGCTG ATTCCAACAG TGATGGCGTT
441 TCATCTGACC ACACGCAACG GAGAACCACA CATGATCGTC AGTAGACAAG
491 AAAAAGGGAA AAGCCTTCTG TTTAAGACAA AGGACGGCAC GAACATGTGT
541 ACCCTCATGG CCATGGACCT TGGTGAGTTG TGTGAAGACA CAATCACGTA
591 TAAATGTCCC TTTCTCAAGC AGAACGAACC AGAAGACATA GATTGTTGGT
641 GCAACTCCAC GTCCACATGG GTAACTTATG GACATGTAC CACCACAGGA Membrane
|
691 GAGCACAGAA GAGAAAAAAG ATCAGTGGCG CTTGTTCCAC ACGTGGGAAT
741 GGGATTGGAG ACACGAACTG AAACATGGAT GTCATCAGAA GGGGCCTGGA
791 AACATGCCCA GAGAATTGAA ACTTGGATTC TGAGACATCC AGGCTTTACC
841 ATAATGGCCG CAATCCTGGC ATACACCATA GGAACGACGC ATTTCCAAAG Envelope
|
891 AGTCCTGATA TTCATCCTAC TGACAGCCAT CGCTCCTTCA ATGACAATGC
941 GCTGCATAGG AATATCAAAT AGGGACTTTG TGGAAGGAGT GTCAGGAGGG
991 AGTTGGGTTG ACATAGTTTT AGAACATGGA AGTTGTGTGA CGACGATGGC
1041 AAAAAATAAA CCAACACTGG ACTTTGAACT GATAAAAACA GAAGCCAAAC
1091 AACCCGCCAC CTTAAGGAAG TACTGTATAG AGGCTAAACT GACCAACACG
1141 ACAACAGACT CGCGCTGCCC AACACAAGGG GAACCCACCC TGAATGAAGA
1191 GCAGGACAAA AGGTTTGTCT GCAAACATTC CATGGTAGAC AGAGGATGGG
1241 GAAATGGATG TGGATTATTT GGAAAAGGAG CATCGTGAC CTGTGCCATG
                                A
1291 TTCACATGCA AAAAGAACAT GGAGGGAAAA ATTGTGCAGC CAGAAAACCT
                  G
1341 GGAATACACT GTCGTTATAA CACCTCATTC AGGGGAAGAA CATGCAGTCG
1391 GAAATGACAC AGGAAAACAT GGTAAAGAAG TCAAGATAAC ACCACAGAGC
1441 TCCATCACAG AGGCGGAACT GACAGGCTAT GGCACTGTTA CGATGGAGTG
1491 CTCTCCAAGA ACGGGCCTCG ACTTCAATGA GATGGTGTTG CTGCAAATGA
1541 AAGACAAAGC TTGGCTGGTG CACAGACAAT GGTTCCTAGA CCTACCGTTG
1591 CCATGGCTGC CCGGAGCAGA CACACAAGGA TCAAATTGGA TACAGAAAGA

FIG.2A

```
1641 GACACTGGTC ACCTTCAAAA ATCCCCATGC GAAAAAACAG GATGTTGTTG
1691 TCTTAGGATC CCAAGAGGGG GCCATGCATA CAGCACTCAC AGGGGCTACG
1741 GAAATCCAGA TGTCATCAGG AAACCTGCTG TTCACAGGAC ATCTTAAGTG
1791 CAGGCTGAGA ATGGACAAAT TACAACTTAA AGGGATGTCA TACTCCATGT
                              A
1841 GCACAGGAAA GTTTAAAGTT GTGAAGGAAA TAGCAGAAAC ACAACATGGA
                                                        *
1891 ACAATAGTCA TTAGAGTACA ATATGAAGGA GACGGCTCTC CATGCAAGAT
1941 CCCTTTTGAG ATAATGGATC TGGAAAAAAG ACATGTTTTG GGCCGCCTGA
          *                                    T*
1991 TCACAGTCAA CCCAATTGTA ACAGAAAAGG ACAGCCCAGT CAACATAGAA
2041 GCAGAACCTC CATTCGGAGA CAGCTACATC ATCATAGGAG TGGAACCAGG
2091 ACAATTGAAG CTGGACTGGT TCAAGAAAGG AAGTTCCATC GGCCAAATGT
2141 TTGAGACAAC AATGAGGGGA GCGAAAAGAA TGGCCATTTT GGGCGACACA
2191 GCCTGGGATT TTGGATCTCT GGGAGGAGTG TTCACATCAA TAGGAAAGGC
2241 TCTCCACCAG GTTTTTGGAG CAATCTACGG GGCTGCTTTC AGTGGGGTCT
2291 CATGGACTAT GAAGATCCTC ATAGGAGTTA TCATCACATG GATAGGAATG
2341 AACTCACGTA GCACATCACT GTCTGTGTCA CTGGTATTAG TGGGAATCGT
                                                    NS1
                        N                           |
2391 GACACTGTAC TTGGGAGTTA TGGTGCAGGC CGATAGTGGT TGCGTTGTGA
2441 GCTGGAAGAA CAAAGAACTA AAATGTGGCA GTGGAATATT CGTCACAGAT
2491 AACGTGCATA CATGGACAGA ACAATACAAG TTCCAACCAG AATCCCCTTC
2541 AAAACTGGCT TCAGCCATCC AGAAAGCTCA TGAAGAGGGC ATCTGTGGAA
2591 TCCGCTCAGT AACAAGACTG GAAAATCTTA TGTGGAAACA AATAACATCA
2641 GAATTGAATC ATATTCTATC AGAAAATGAA GTGAAACTGA CCATCATGAC
2691 AGGAGACATC AAAGGAATCA TGCAGGTAGG AAAACGATCT CTGCGGCCTC
2741 AACCCACTGA GTTGAGGTAT TCATGGAAAA CATGGGGTAA AGCGAAAATG
2791 CTCTCCACAG AACTCCATAA TCAGACCTTC CTCATTGATG GTCCCGAAAC
2841 AGCAGAATGC CCCAACACAA ACAGAGCTTG GAATTCACTA GAAGTTGAGG
2891 ACTACGGCTT TGGAGTATTC ACTACCAATA TATGGCTAAG ATTGAGAGAA
2941 AAGCAGGATG CATTTTGTGA CTCAAAACTC ATGTCAGCGG CCATAAAGGA
2991 CAACAGAGCC GTCCATGCTG ATATGGGTTA TTGGATAGAA AGCGCACTCA
3041 ATGATACATG GAAGATAGAG AAAGCTTCTT TCATTGAAGT CAAAAGTTGC
3091 C CTGGCCAA AGTCACACAC TCTATGGAGT AATGGAGTGC TAGAAAGCGA
3141 GATGGTAATT CCAAAGAATT TCGCTGGACC AGTGTCACAA CATAATAACA
3191 GACCAGGCTA TCACACACAA ACAGCAGGAC CTTGGCATCT AGGCAAGCTT
3241 GAGATGGACT TTGATTTCTG CGAAGGGACT ACAGTGGTGG TAACCGAGGA
3291 CTGTGGAAAC AGAGGGCCCT CTTTAAGAAC AACCACTGCC TCAGGAAAAC
3341 TCATAACGGA ATGGTGTTGT CGATCTTGCA CACTACCACC ACTAAGATAC
3391 AGAGGTGAGG ATGGATGCTG GTACGGGATG GAAATCAGAC CATTGAAAGA
3441 GAAAGAAGAA AATCTGGTCA GTTCTCTGGT CACAGCC
```

FIG.2B

97                              ATGA ATAACCAACG GAAAAAGGCG AGAAACACGC
                                Met  AsnAsnGlnArg LysLysAla  ArgAsnThr>
                                ◆ Capsid 131 CTTTCAATAT GCTGAAACGC GAGAGAAACC GCGTGTCAAC TGTACAACAG TTGACAAAGA
    ProPheAsnMet LeuLysArg GluArgAsn ArgValSerThr ValGlnGln LeuThrLys>

191 GATTCTCACT TGGAATGCTG CAGGGACGAG GACCACTAAA ATTGTTCATG GCCCTGGTGG
    ArgPheSerLeu GlyMetLeu GlnGlyArg GlyProLeuLys LeuPheMet AlaLeuVal>

251 CATTCCTTCG TTTCCTAACA ATCCCACCAA CAGCAGGGAT ATTAAAAAGA TGGGGAACAA
    AlaPheLeuArg PheLeuThr IleProPro ThrAlaGlyIle LeuLysArg TrpGlyThr>

311 TTAAAAAATC AAAGGCTATT AATGTTCTGA GAGGCTTCAG GAAAGAGATT GGAAGGATGC
    IleLysLysSer LysAlaIle AsnValLeu ArgGlyPheArg LysGluIle GlyArgMet>

371 TGAATATCTT AAACAGGAGA CGTAGAACTG CAGGCATGAT CATCATGCTG ATTCCAACAG
    LeuAsnIleLeu AsnArgArg ArgArgThr AlaGlyMetIle IleMetLeu IleProThr>

431 TGATGGCGTT TCATCTGACC ACACGCAACG GAGAACCACA CATGATCGTC AGTAGACAAG
    ValMetAlaPhe HisLeuThr ThrArgAsn GlyGluProHis MetIleVal SerArgGln>
                                                            ◆ PreMembrane 491 AAAAAGGGAA AAGCCTTCTG TTTAAGACAA AGGACGGCAC GAACATGTGT ACCCTCATGG
    GluLysGlyLys SerLeuLeu PheLysThr LysAspGlyThr AsnMetCys ThrLeuMet>

551 CCATGGACCT TGGTGAGTTG TGTGAAGACA CAATCACGTA TAAATGTCCC TTTCTCAAGC
    AlaMetAspLeu GlyGluLeu CysGluAsp ThrIleThrTyr LysCysPro PheLeuLys>

611 AGAACGAACC AGAAGACATA GATTGTTGGT GCAACTCCAC GTCCACATGG GTAACTTATG
    GlnAsnGluPro GluAspIle AspCysTrp CysAsnSerThr SerThrTrp ValThrTyr>

671 GGACATGTAC CACCACAGGA GAGCACAGAA GAGAAAAAAG ATCAGTGGCG CTTGTTCCAC
    GlyThrCysThr ThrThrGly GluHisArg ArgGluLysArg SerValAla LeuValPro>
                                                            ◆ Membrane 731 ACGTGGGAAT GGGATTGGAG ACACGAACTG AAACATGGAT GTCATCAGAA GGGGCCTGGA
    HisValGlyMet GlyLeuGlu ThrArgThr GluThrTrpMet SerSerGlu GlyAlaTrp>

791 AACATGCCCA GAGAATTGAA ACTTGGATTC TGAGACATCC AGGCTTTACC ATAATGGCCG
    LysHisAlaGln ArgIleGlu ThrTrpIle LeuArgHisPro GlyPheThr IleMetAla>

FIG.3A

```
 851 CAATCCTGGC ATACACCATA GGAACGACGC ATTTCCAAAG AGTCCTGATA TTCATCCTAC
     AlaIleLeuAla TyrThrIle GlyThrThr HisPheGlnArg ValLeuIle PheIleLeu>

911 TGACAGCCAT CGCTCCTTCA ATGACAATGC GCTGCATAGG AATATCAAAT AGGGACTTTG
     LeuThrAlaIle AlaProSer MetThrMet ArgCysIleGly IleSerAsn ArgAspPhe>
                                       ◆ Envelope 971 TGGAAGGAGT GTCAGGAGGG AGTTGGGTTG ACATAGTTTT AGAACATGGA AGTTGTGTGA
     ValGluGlyVal SerGlyGly SerTrpVal AspIleValLeu GluHisGly SerCysVal>

1031 CGACGATGGC AAAAAATAAA CCAACACTGG ACTTTGAACT GATAAAAACA GAAGCCAAAC
     ThrThrMetAla LysAsnLys ProThrLeu AspPheGluLeu IleLysThr GluAlaLys>

1091 AACCCGCCAC CTTAAGGAAG TACTGTATAG AGGCTAAACT GACCAACACG ACAACAGACT
     GlnProAlaThr LeuArgLys TyrCysIle GluAlaLysLeu ThrAsnThr ThrThrAsp>

1151 CGCGCTGCCC AACACAAGGG GAACCCACCC TGAATGAAGA GCAGGACAAA AGGTTTGTCT
     SerArgCysPro ThrGlnGly GluProThr LeuAsnGluGlu GlnAspLys ArgPheVal>

1211 GCAAACATTC CATGGTAGAC AGAGGATGGG GAAATGGATG TGGATTATTT GGAAAAGGAG
     CysLysHisSer MetValAsp ArgGlyTrp GlyAsnGlyCys GlyLeuPhe GlyLysGly>

WT                                                   GAA(Glu)
1271 GCATCGTGAC CTGTGCCATG TTCACATGCA AAAAGAACAT GGAGGGAAAA ATTGTGCAGC
     GlyIleValThr CysAlaMet PheThrCys LysLysAsnMet GluGlyLys IleValGln>

WT                         GTG(Val)
1331 CAGAAAACCT GGAATACACT GTCGTTATAA CACCTCATTC AGGGGAAGAA CATGCAGTCG
     ProGluAsnLeu GluTyrThr ValValIle ThrProHisSer GlyGluGlu HisAlaVal>

1391 GAAATGACAC AGGAAAACAT GGTAAAGAAG TCAAGATAAC ACCACAGAGC TCCATCACAG
     GlyAsnAspThr GlyLysHis GlyLysGlu ValLysIleThr ProGlnSer SerIleThr>

1451 AGGCGGAACT GACAGGCTAT GGCACTGTTA CGATGGAGTG CTCTCCAAGA ACGGGCCTCG
     GluAlaGluLeu ThrGlyTyr GlyThrVal ThrMetGluCys SerProArg ThrGlyLeu>

1511 ACTTCAATGA GATGGTGTTG CTGCAAATGA AAGACAAAGC TTGGCTGGTG CACAGACAAT
     AspPheAsnGlu MetValLeu LeuGlnMet LysAspLysAla TrpLeuVal HisArgGln>

1571 GGTTCCTAGA CCTACCGTTG CCATGGCTGC CCGGAGCAGA CACACAAGGA TCAAATTGGA
     TrpPheLeuAsp LeuProLeu ProTrpLeu ProGlyAlaAsp ThrGlnGly SerAsnTrp>
```

FIG.3B

```
1601 TACAGAAAGA GACACTGGTC ACCTTCAAAA ATCCCCATGC GAAAAAACAG GATGTTGTTG
     IleGlnLysGlu ThrLeuVal ThrPheLys AsnProHisAla LysLysGln AspValVal>

1691 TCTTAGGATC CCAAGAGGGG GCCATGCATA CAGCACTCAC AGGGGCTACG GAAATCCAGA
     ValLeuGlySer GlnGluGly AlaMetHis ThrAlaLeuThr GlyAlaThr GluIleGln>

1751 TGTCATCAGG AAACCTGCTG TTCACAGGAC ATCTTAAGTG CAGGCTGAGA ATGGACAAAT
     MetSerSerGly AsnLeuLeu PheThrGly HisLeuLysCys ArgLeuArg MetAspLys>

WT                                                      ATT(Ile)
1811 TACAACTTAA AGGGATGTCA TACTCCATGT GCACAGGAAA GTTAAAGTT GTGAAGGAAA
     LeuGlnLeuLys GlyMetSer TyrSerMet CysThrGlyLys PheLysVal ValLysGlu>

1871 TAGCAGAAAC ACAACATGGA ACAATAGTCA TTAGAGTACA AIATGAAGGA GACGGCTCTC
     IleAlaGluThr GlnHisGly ThrIleVal IleArgValGln TyrGluGly AspGlySer>

1931 CATGCAAGAT CCCTTTTGAG ATAATGGATC TGGAAAAAAG ACATGTTTTG GGCCGCCTGA
     ProCysLysIle ProPheGlu IleMetAsp LeuGluLysArg HisValLeu GlyArgLeu>

WT                           AGT(Ser)
1991 TCACAGTCAA CCCAATTGTA ACAGAAAAGG ACAGCCCAGT CAACATAGAA CCAGAACCTC
     IleThrValAsn ProIleVal ThrGluLys AspSerProVal AsnIleGlu AlaGluPro>

2051 CATTCGGAGA CAGCTACATC ATCATAGGAG TGGAACCAGG ACAATTGAAG CTGGACTGGT
     ProPheGlyAsp SerTyrIle IleIleGly ValGluProGly GlnLeuLys LeuAspTrp>

2111 TCAAGAAAGG AAGTTCCATC GGCCAAATGT TTGAGACAAC AATGAGGGGA GCGAAAAGAA
     PheLysLysGly SerSerIle GlyGlnMet PheGluThrThr MetArgGly AlaLysArg>

2171 TGGCCATTTT GGGCGACACA GCCTGGGATT TTGGATCTCT GGGAGGAGTG TTCACATCAA
     MetAlaIleLeu GlyAspThr AlaTrpAsp PheGlySerLeu GlyGlyVal PheThrSer>

2231 TAGGAAAGGC TCTCCACCAG GTTTTTGGAG CAATCTACGG GGCTGCTTTC AGTGGGGTCT
     IleGlyLysAla LeuHisGln ValPheGly AlaIleTyrGly AlaAlaPhe SerGlyVal>

2291 CATGGACTAT GAAGATCCTC ATAGGAGTTA TCATCACATG GATAGGAATG AACTCACGTA
     SerTrpThrMet LysIleLeu IleGlyVal IleIleThrTrp IleGlyMet AsnSerArg>

2351 GCA ATCACT GTCTGTGTCA CTGGTATTAG TGGGAATCGT GACACTGTAC TTGGGACTA
     Ser  SerLeu SerValSer LeuValLeu ValGlyIleVal ThrLeuTyr LeuGlyVal>
```

FIG.3C

```
2411 TGGTGCAGGC CGATAGTGGT TGCGTTGiGA GCTGGAAGAA CAAAGAACTA AAATGTGGCA
     MetValGlnAla AspSerGly CysValVal SerTrpLysAsn LysGluLeu LysCysGly>
            ◆ NS1

2471 GTGGAATATT rGTCACAGAT AACGTGCATA CATGGACAGA ACAATACAAG TTCCAACCAG
     SerGlyIlePhe ValThrAsp AsnValHis ThrTrpThrGlu GlnTyrLys PheGlnPro>

2531 AATCCCCTTC AAAACTGGCT TCAGCCATCC AGAAAGCTCA TGAAGAGGGC ATCTGTGGAA
     GluSerProSer LysLeuAla SerAlaIle GlnLysAlaHis GluGluGly IleCysGly>

2591 TCCGCTCAGT AACAAGACTG GAAAATCTTA TGTGGAAACA AATAACATCA GAATTGAATC
     IleArgSerVal ThrArgLeu GluAsnLeu MetTrpLysGln IleThrSer GluLeuAsn>

2651 ATATTCTATC AGAAAATGAA GTGAAACTGA CCATCATGAC AGGAGACATC AAAGGAATCA
     HisIleLeuSer GluAsnGlu ValLysLeu ThrIleMetThr GlyAspIle LysGlyIle>

2711 TGCAGGTAGG AAAACGATCT CTGCGGCCTC AACCCACTGA GTTGAGGTAT TCATGGAAAA
     MetGlnValGly LysArgSer LeuArgPro GlnProThrGlu LeuArgTyr SerTrpLys>

2771 CATGGGGTAA AGCGAAAATG CTCTCCACAG AACTCCATAA TCAGACCTTC CTCATTGATG
     ThrTrpGlyLys AlaLysMet LeuSerThr GluLeuHisAsn GlnThrPhe LeuIleAsp>

2831 GTCCCGAAAC AGCAGAATGC CCCAACACAA ACAGAGCTTG GAATTCACTA GAAGTTGAGG
     GlyProGluThr AlaGluCys ProAsnThr AsnArgAlaTrp AsnSerLeu GluValGlu>

2891 ACTACGGCTT TGGAGTATTC ACTACCAATA TATGGCTAAG ATTGAGAGAA AAGCAGGATG
     AspTyrGlyPhe GlyValPhe ThrThrAsn IleTrpLeuArg LeuArgGlu LysGlnAsp>

2951 CATTTTGTGA CTCAAAACTC ATGTCAGCGG CCATAAAGGA CAACAGAGCC GTCCATGCTG
     AlaPheCysAsp SerLysLeu MetSerAla AlaIleLysAsp AsnArgAla ValHisAla>

3011 ATATGGGTTA TTGGATAGAA AGCGCACTCA ATGATACATG GAAGATAGAG AAAGCTTCTT
     AspMetGlyTyr TrpIleGlu SerAlaLeu AsnAspThrTrp LysIleGlu LysAlaSer>

3071 TCATTGAAGT CAAAAGTTGC CACTGGCCAA AGTCACACAC TCTATGGAGT AATGGAGTGC
     PheIleGluVal LysSerCys HisTrpPro LysSerHisThr LeuTrpSer AsnGlyVal>

3131 TAGAAAGCGA GATGGTAATT CCAAAGAATT TCGCTGGACC AGTGTCACAA CATAATACA
     LeuGluSerGlu MetValIle ProLysAsn PheAlaGlyPro ValSerGln HisAs· sn>

3191 GACCAGGCTA TCACACACAA ACAGCAGGAC CTTGGCATCT AGGCAAGCTT GAGATGGACT
     ArgProGlyTyr HisThrGln ThrAlaGly ProTrpHisLeu GlyLysLeu GluMetAsp>
```

FIG.3D

```
3251 TTGATTTCTG CGAAGGGACT ACAGTGGTGG TAACCGAGGA CTGTGGAAAC AGAGGGCCCT
     PheAspPheCys GluGlyThr ThrValVal ValThrGluAsp CysGlyAsn ArgGlyPro>

3311 CTTTAAGAAC AACCACTGCC TCAGGAAAAC TCATAACGGA ATGGTGTTGT CGATCTTGCA
     SerLeuArgThr ThrThrAla SerGlyLys LeuIleThrGlu TrpCysCys ArgSerCys>

3371 CACTACCACC ACTAAGATAC AGAGGTGAGG ATGGATGCTG GTACGGGATG GAAATCAGAC
     ThrLeuProPro LeuArgTyr ArgGlyGlu AspGlyCysTrp TyrGlyMet GluIleArg>

3431 CATTGAAAGA GAAAGAAGAA AATCTGGTCA GTTCTCTGGT CACAGCC
     ProLeuLysGlu LysGluGlu AsnLeuVal SerSerLeuVal ThrAla
```

FIG.3E

Before mutagenesis:
```
1789                        Trypsin                          1848
  |                            ↓                               |
5'-TGCAGGCTGAGAATGGACAAATTACAACTTAAAGGGATGTCATACTCCATGTGCACAGGA-3'
   CysArgLeuArgMetAspLysLeuGlnLeuLysGlyMetSerTyrSerMetCysThrGly
```

Mutagenizing Oligonucleotide:
```
   3'-CCGACTCTTACCTGTTTA            CCCTACAGTATGAGG-5'
                         ╲         |
                         ctatcagctgtcga
```

After mutagenesis:      SalI    PvuII
```
                         v       v
5'-TGCAGGCTGAGAATGGACAAATgatagtcgacagctGGGATGTCATACTCCATGTGCACAGGA-3'
...CysArgLeuArgMetAspLysEndEnd          GlyMetSerTyrSerMetCysThrGly...
       C-terminus of 60%E              N-terminus of domain B
```

FIG.4

5318 ATGAGATTTCCTTCAATTTTTACTGCAGTTTTATTCGCAGCATCCTCCGC
     MetArgPheProSerIlePheThrAlaValLeuPheAlaAlaSerSerAla>
     ↦ MFα secretion signal peptide 5368 ATTAGCTGCTCCAGTCAACACTACAACAGAAGATGAAACGGCACAAATTC
     LeuAlaAlaProValAsnThrThrThrGluAspGluThrAlaGlnIle>
         ▲ Signalase cleavage
         ↦ MFα propeptide 5418 CGGCTGAAGCTGTCATCGGTTACTCAGATTTAGAAGGGGATTTCGATGTT
     ProAlaGluAlaValIleGlyTyrSerAspLeuGluGlyAspPheAspVal>

5468 GCTGTTTTGCCATTTTCCAACAGCACAAATAACGGGTTATTGTTTATAAA
     AlaValLeuProPheSerAsnSerThrAsnAsnGlyLeuLeuPheIleAsn>

5518 TACTACTATTGCCAGCATTGCTGCTAAAGAAGAAGGGGTATCTCTCGAGA
     ThrThrIleAlaSerIleAlaAlaLysGlnGluGlyValSerLeuGlu>

5568 AAAGGGAGGCTGGGATGTCATACTCCATGTGCACAGGAAAGTTTAAAGTT
     LysArgGluAlaGlyMetSerTyrSerMetCysThrGlyLysPheLysVal>
         ▲ Kex2p cleavage
         ↦ Domain B 5618 GTGAAGGAAATAGCAGAAACACAACATGGAACAATAGTCATTAGAGTACA
     ValLysGluIleAlaGluThrGlnHisGlyThrIleValIleArgValGln>

5668 ATATGAAGGAGACGGCTCTCCATGCAAGATCCCTTTTGAGATAATGGATC
     TyrGluGlyAspGlySerProCysLysIleProPheGluIleMetAsp>

5718 TGGAAAAAAGACATGTTTTGGGCCGCCTGATCACAGTCAATCCAATTGTA
     LeuGluLysArgHisValLeuGlyArgLeuIleThrValAsnProIleVal>

5768 ACAGAAAAGGACAGCCCAGTCAACATAGAAGCAGAACCTCCATTCGGAGA
     ThrGluLysAspSerProValAsnIleGluAlaGluProProPheGlyAsp>

5818 CAGCTACATCATCATAGGAGTGGAACCAGGACAATTGAAGCTGGACTGGT
     SerTyrIleIleIleGlyValGluProGlyGlnLeuLysLeuAspTrp>

5868 TCAAGAAAGGATAA
     PheLysLysGlyEnd>

FIG.7

```
           220         230         240         250         260         270         280
            *           *           *           *           *           *           *
       GACGGCTCTC CATGCAAGAT CCCTTTTGAG ATAATGGATC TGGAAAAAAG ACATGTTTTG GGCCGCCTGA
       CTGCCGAGAG GTACGTTCTA GGGAAAACTC TATTACCTAG ACCTTTTTC  TGTACAAAAC CCGGCGGACT
       AspGlySer ProCysLysIle ProPheGlu IleMetAsp LeuGluLysArg HisValLeu GlyArgLeu>
                C                      RGARSP-Domain B           C 290         300         310         320         330         340         350
            *           *           *           *           *           *           *
       TCACAGTCAA CCCAATTGTA ACAGAAAAGG ACAGTCCAGT CAACATAGAA GCAGAACCTC CATTCGGAGA
       AGTGTCAGTT GGGTTAACAT TGTCTTTTCC TGTCAGGTCA GTTGTATCTT CGTCTTGGAG GTAAGCCTCT
       IleThrValAsn ProIleVal ThrGluLys AspSerProVal AsnIleGlu AlaGluPro ProPheGlyAsp>
                C                      RGARSP-Domain B           C 360         370         380         390         400         410
            *           *           *           *           *           *
       CAGCTACATC ATCATAGGAG TGGAACCAGG ACAATTGAAG CTGGACTGGT TCAAGAAAGG ATAATAG
       GTCGATGTAG TAGTATCCTC ACCTTGGTCC TGTTAACTTC GACCTGACCA AGTTCTTTCC TATTATC
       SerTyrIle IleIleGly ValGluProGly GlnLeuLys LeuAspTrp PheLysLysGly EndEnd>
                C                      RGARSP-Domain B_C
```

FIG.9B

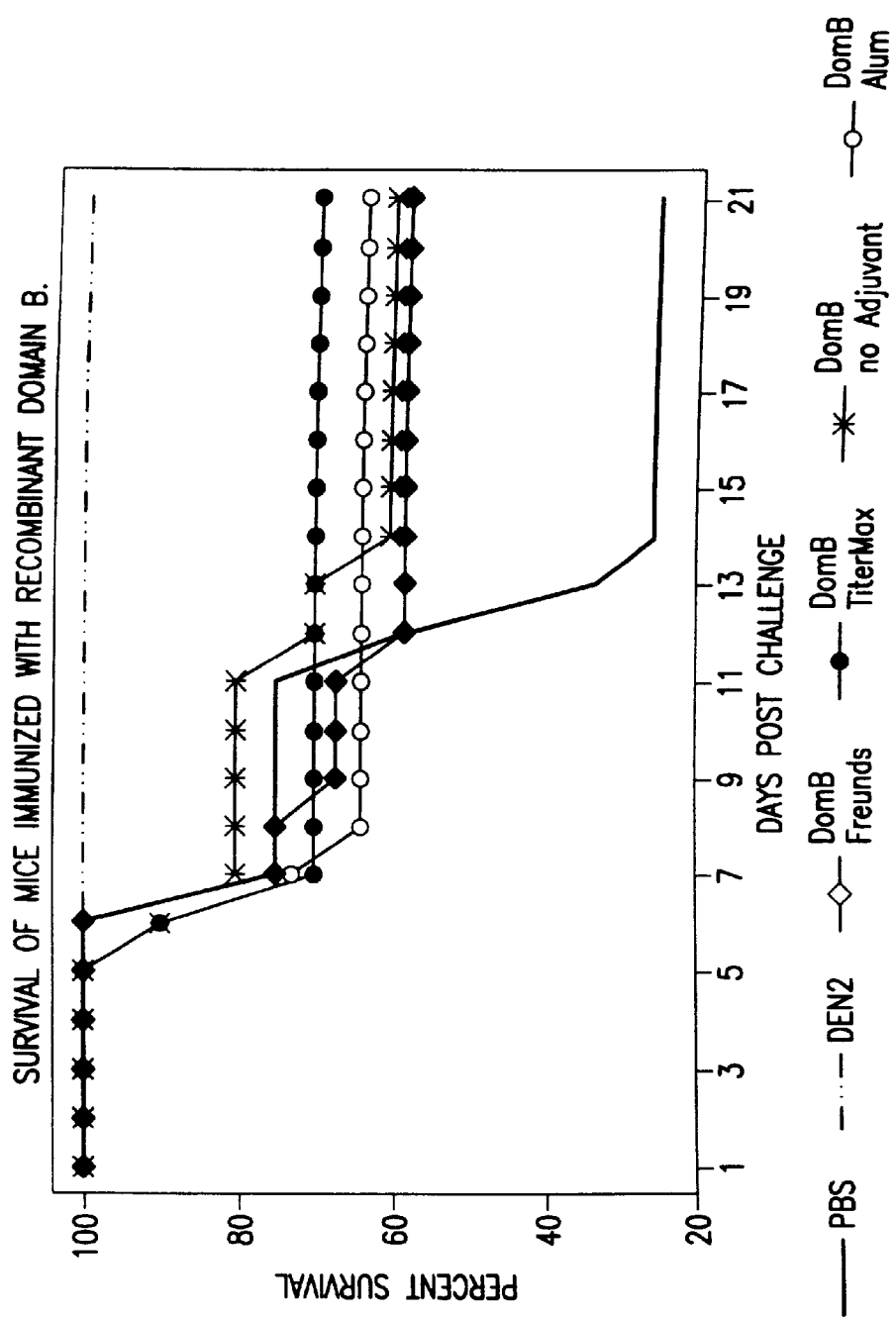

CONSTRUCTION OF THE pMttDomB
EXPRESSION PLASMID

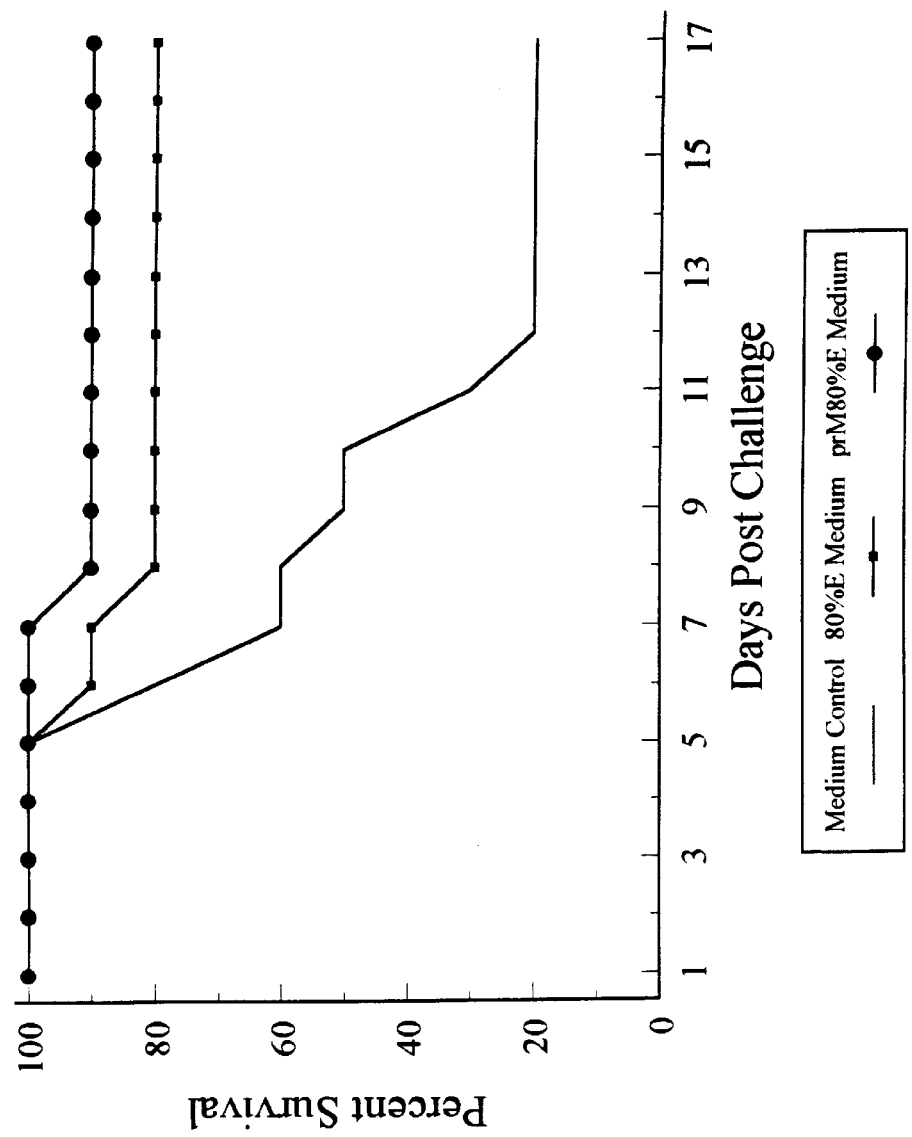

SUBUNIT IMMONOGENIC COMPOSITION AGAINST DENGUE INFECTION

This application is a Continuation of application Ser. No. 08/500,469, filed Jul. 10, 1995, now abandoned, which is a continuation-in-part of application Ser. No. 08/488,807, filed Jun. 7, 1995 which is a continuation-in-part of Ser. No. 08/448,734, filed May 24, 1995, now abandoned. The disclosures of both of these prior applications are incorporated herein by reference in their entireties.

TECHNICAL FIELD

The invention relates to protection against and diagnosis of dengue fever. More specifically, the invention concerns a subunit of the dengue virus envelope protein secreted as a mature recombinantly produced protein from eucaryotic cells which is protective against dengue infection, which raises antibodies useful in passive immunization, and which is useful in diagnosis of infection by the virus.

BACKGROUND ART

The dengue viruses are members of the family Flaviviridae which also includes the Japanese encephalitis (JE) virus, Tick-borne encephalitis (TBE) virus, and the initially discovered prototype of this class, the yellow fever (YF) virus. The flaviviruses contain a single positive strand genomic RNA and are small enveloped viruses affecting animals, but generally transmitted to vertebrates by chronically infected mosquito or tick vectors. Flaviviruses are enveloped by host cell membrane and contain the three structural proteins capsid (C), membrane (M), and envelope (E). The E and M proteins are found on the surface of the virion where they are anchored in the membrane. Mature E is glycosylated, whereas M is not, although its precursor, prM, is a glycoprotein. Glycoprotein E, the largest structural protein, contains functional domains responsible for cell surface attachment and intraendosomal fusion activities. It is also a major target of the host immune system, inducing neutralizing antibodies, protective immunity, as well as antibodies which inhibit hemagglutination.

Dengue virus is the causative agent of dengue fever and is transmitted to man by Aedes mosquitoes, principally Aedes aegypti and Aedes albopictus. Classic dengue fever is an acute illness marked by fever, headache, aching muscles and joints, and rash. A fraction of cases, typically in children, results in more extreme forms of infection, i.e., dengue hemorrhagic fever (DHF) or dengue shock syndrome (DSS). Without diagnosis and prompt medical intervention, the sudden onset and rapid progress of DHF/DSS can be fatal.

Dengue is one of the most important virus groups transmitted to man by arthropods in terms of global morbidity; it has been estimated that dengue is responsible for up to 100 million illnesses annually. With the advent of modern jet travel, dengue has spread globally in the tropics and subtropics, and multiple dengue serotypes in a region are common.

Every flavivirus genome is a single positive-stranded RNA of approximately 10,500 nucleotides containing short 5' and 3' untranslated regions, a single long open reading frame (ORF), a 5' cap, and a nonpolyadenylated 3' terminus. The ten gene products encoded by the single, long open reading frame are contained in a polyprotein organized in the order, C (capsid), prM/M (membrane), E (envelope), NS1 (nonstructural), NS2a, NS2b, NS3, NS4a, NS4b, and NS5 (Chambers, T. J. et al. *Ann Rev Microbiol* (1990) 44:649–688). Processing of the encoded polyprotein is initiated cotranslationally, and full maturation requires both host and viral-specific proteases. The sites of proteolytic cleavage in the YF virus have been determined by comparing the nucleotide sequence and the amino terminal sequences of the viral proteins. Subsequent to initial processing of the polyprotein, prM is converted to M during virus release (Wengler, G. et al. *J Virol* (1989) 63:2521–2526), and anchored C is processed during virus maturation (Nowak et al. *Virology* (1987) 156:127–137).

There are four antigenically related dengue viruses which, however, can be recognized as distinct serotypes. The complete genomic sequence for at least one strain of each of the four dengue serotypes has been reported (DEN-1, Fu, J. et al. *Virology* (1992) 188:953–958; DEN-2, Deubel, V. et al. *Virology* (1986) 155:365–377; Hahn, Y. S. et al. *Virology* (1988) 162:167–180; DEN-3, Osatomi, K. et al. *Virus Genes* (1988) 2:99–108; Osatomi, K. et al. *Virology* (1990) 176:643–647; DEN-4, Zhao, B. E. et al. *Virology* (1986) 155:77–88; Mackow, E. et al. *Virology* (1987) 159:217–228). In addition, the compete genomic sequences of other flaviviruses are known (e.g., YF virus: Rice et al., *Science* (1985) 229:726–733).

It does not appear that infection by one dengue serotype can confer long-term immunity on the individual with respect to other serotypes. In fact, secondary infections with heterologous serotypes are quite common. In general, antibody responses in infected subjects to primary infection are mostly IgM antibodies and these antibodies are directed against type-specific determinants. On the other hand, secondary infections by heterologous serotypes generate IgG antibodies which are flavivirus crossreactive.

Helpful reviews of the nature of the dengue disease, the history of attempts to develop suitable vaccines, and structural features of flaviviruses in general as well as the molecular structural features of the envelope protein of flaviviruses are found in Halstead, S. B. *Science* (1988) 239:476–481; Brandt, W. E. *J Infect Disease* (1990) 162:577–583; Chambers, T. J. et al. *Annual Rev Microbiol* (1990) 44:649–688; Mandl, C. W. et al. *Virology* (1989) 63:564–571; and Henchal, E. A. and J. R. Putnak, *Clin Microbiol Rev* (1990) 3:376–396.

A successful vaccine for protection against dengue infection has never been developed. However, there have been a number of preliminary efforts, many of which focus on the envelope protein, since this protein is exposed at the surface and is believed to be responsible for eliciting immunity.

Monoclonal antibodies (Mabs) directed against purified E of several flaviviruses DEN-2 (Henchal et al. *Am J Trop Med Hyg* (1985) 34:162–169, TBE (Heinz, F. X. et al. *Virology* (1983) 126:525–537), St. Louis encephalitis (SLE, Mathews, J. H. et al. *J Immunol* (1984) 132:1533–1537), Murray Valley encephalitis (MVE, Hawkes, R. A. et al. *J Gen Virol* (1988) 69:1105–1109), and JE (Takegami, T. et al. *Acta Virologica* (1982) 26:312–320) are neutralizing in vitro. Some of these Mabs can also passively confer protection in vivo (Heinz, F. X. et al. (1983, supra)); Mathews, J. H. et al. (1984, supra)); Kimuro-Kuroda and Yasui, *J Immunol* (1988) 141:3603–3610).

Although the primary amino acid sequence of the flavivirus E glycoprotein is variable (45–80% identity), all have twelve conserved cysteine residues, forming six disulfide bridges, and hydrophilicity profiles are nearly superimposable, suggesting that they may all have similar secondary and tertiary structures. Based on the position of the 12 conserved cysteines (determined for West Nile virus, Nowak and Wengler, *Virology* (1987) 156:127–137), monoclonal antibody competitive binding studies, monoclonal antibody binding to purified proteolytic fragments, and analysis of neutralizing antibody escape mutants of Tick-Borne Encephalitis Virus, glycoprotein E was divided into three antigenic domains (A, B, and C) and two transmembrane segments at its carboxy-terminus. See, for example, Mandl, C. W. et al. *J Virol* (1989) 63:564–571. FIG. 1, reproduced from this article, shows the locations of these domains.

Domain A was defined as a denaturation sensitive, highly folded, and disulfide stabilized discontinuous domain composed of the amino acids from 50–125 and 200–250 containing five of the six disulfide bridges. Neutralization and hemagglutination inhibition epitopes are found within domain A, and, for dengue viruses, one of the two N-linked glycosylation sites. A conserved hydrophobic amino acid sequence within domain A as been postulated to provide fusogenic properties after low pH treatment. Amino acid sequences conserved among the flavivirus family are located within this region; thus, broadly flavivirus-cross-reactive epitopes lie within this domain.

Domain B was identified as a continuous domain composed of amino acids 301–395 (an approximate region between amino acids 300–400 for all flaviviruses). The domain can be isolated as a single immunoreactive proteolytic fragment. It has been postulated that this domain forms part of the receptor binding site (Heinz, F. X. et al. *APMIS* (1993) 101:735–745), and attenuating mutations have been mapped to sequences within domain B Heinz et al. (supra). A variety of neutralizing antibodies have been shown to specifically map to Domain B (Heinz et al. (1983, supra)); Trirawatanapong et al., 1992; Megret et al., 1992; Lin et al., 1994). The binding of these neutralizing monoclonal antibodies is dependent on formation of a disulfide bond, and in some cases also is sensitive to detergent denaturation. Species-specific monoclonal antibodies bind this domain.

Domain C represents a hypervariable loop between the two segments of Domain A. Its antigenicity is insensitive to denaturation or reducing agents, and contains one N-linked glycosylation site. Predominantly sub-type specific monoclonal antibodies react with this domain. No specific activity has been assigned to this domain.

Many strategies are currently under investigation to develop an effective and safe dengue vaccine; however, to date, no single strategy has proven completely satisfactory. Attempts to generate live attenuated dengue vaccine strains have not been entirely successful, although research into this area continues. In the absence of effective, live attenuated dengue vaccines, a significant effort has been invested in the development of recombinant, dengue subunit or viral-vectored vaccines.

Recombinant dengue proteins have been expressed in several systems to date (see Putnak, R. A. (1994) *Modern Vaccinology*, E. Kurstak ed., Plenum Medical, New York, pp. 231–252, for review). Most efforts using *Escherichia coli* have yielded poor immunogen unable to elicit neutralizing antibodies. This may reflect non-native conformation of dengue proteins expressed in the bacteria and the necessity to process the viral proteins through the secretion pathway in order to form the proper disulfide bonds, glycosylate the proteins, or both.

Several reports have described vaccinia-flavivirus recombinants expressing envelope protein as part of a polyprotein (e.g. C-prM-E-NS1; [Dengue] Zhao, B. G. et al. *J Virol* (1987) 61:4019–4022; Deubel, V. et al. *J Gen Virol* (1988) 69:1921–1929; Bray, M. et al. *J Virol* (1991) 63:2853–2856; [YF] Hahn, Y. S. et al. *Arch Virol* (1990) 115:251–265), as a single protein (e.g. 100% E; [Dengue] Bray, M. et al., *J Virol* (1989) 63:2853–2856), or as polypeptides (e.g. 79% E-RKG; Men, R. et al. *J Virol* (1991) 65:1400–1407). The most successful recombinant vaccinia viruses, those capable of inducing neutralizing antibodies and protecting mice from virus challenge, were those which were secreted E extracellularly or accumulated E on the cell surface.

Men, R. et al. (1991, supra) described the recombinant production of various C-terminal truncations of the DEN-4 envelope protein using a recombinant Vaccinia virus vector and infecting mammalian CVI cells. The results showed that the recombinants that contain greater than 79% of the coding sequence produced an intracellular protein that could be immunoprecipitated with anti-dengue virus antibodies contained in hyperimmune mouse ascitic fluid (HMAF). Although there was a reduced level of detection for protein which contained 79% of envelope or less, this did not appear to result from reduced production of the protein. It was also found that only truncations which contained 79% of E or less were secreted efficiently; E polypeptides equal to or larger than 81% E were not secreted efficiently.

Men et al. (1991, supra) constructed additional C-terminal truncations between 79% E and 81% E to map the amino acids responsible for the difference in secretion and immunoreactivity with HMAF of these two truncated E polypeptides. The results demonstrated that 79% E containing the additional tripeptide sequence RKG was also secreted. Although both 59% E and 79% E-RKG were secreted, only 79% E-RKG was detected at the cells' surface. The recombinant Vaccinia viruses containing various truncations were also used to immunize mice. Mice immunized with recombinants expressing 79% E-RKG or larger portions of the envelope protein were protected. However, except for 59% E, mice immunized with 79% E or a smaller product were only partially protected. The 59% E elicited high protection rates (>90%) comparable to 79% E-RKG and larger C-terminal truncated E polypeptides. Protection correlated with binding to HMAF.

Combinations of immunogenic structural and nonstructural JE virus, DEN-1, DEN-2, and DEN-4 proteins have been expressed by baculovirus recombinants(Matsuura, Y. et al. *Virology* (1989) 173:674–682; Putnak, R. A. et al. *Am J Trop Med Hyg* (1991) 45:159–167; Deubel, V. et al. *Virology* (1991) 180:442–447). Baculovirus-expressed dengue and JE E glycoprotein elicited neutralizing antibodies, protected mice from a lethal dengue virus challenge, or both. In spite of these successes, the expression levels reported in baculovirus are low and the recombinant protein is less immunogenic than the viral protein (Putnak, R. A. et al. *Am J Trop Med Hyg* (1991) supra).

Research with purified polypeptides released by proteolysis of flavivirus envelope proteins, with recombinant polypeptides, and with synthetic peptides has indicated where protective epitopes may map. The isolated 9000 dalton domain B trypsin fragment from TBE virus spontaneously refolds and is stabilized by disulfide bridges (Winkler, G. et al. *J Gen Virol* (1987) 68:2239–2244). This disulfide stabilized fragment elicited neutralizing antibodies in mice (Heinz, F. X. et al. *Virology* (1984) 130:485–501). In contrast, a 28,000 dalton trypsin fragment from WN virus containing domain B sequences was unable to spontaneously refold and did not elicit neutralizing antibodies (Wengler and Wengler, 1989).

A cyanogen bromide-cleaved 8 kD fragment (amino acids 375–456) overlapping domain B from JE envelope protein was found to induce neutralizing antibodies in mice (Srivastava, A. K. et al. *Acta Virol* (1990) 34:228–238). Immunization of mice with a larger polypeptide (JE E amino acid 319 to NS1 amino acid 65) spanning the 8 kD peptide expressed in *Escherichia coli* as a fusion to protein A elicited neutralizing antibodies and protected mice from lethal virus challenge (Srivastava, A. K. et al. *Microbiol Immunol* (1991) 35:863–870). This polypeptide begins between the two cysteines within domain B, and, therefore, cannot form the stabilizing disulfide bond that earlier reports suggest is necessary for presentation of protective epitopes.

Immunization of mice with synthetic peptides corresponding to amino acids within domain B, aa 356–376 from MVE (Roehrig, J. T. et al. *Virology* (1989) 171:49–60) or aa 352–368 from DEN-2 virus (Roehrig, J. T. et al. *Virology* (1990) 177:668–675), elicited low levels of neutralizing antibodies in mice, suggesting the presence in domain B of a weak linear neutralizing epitope (Roehrig, J. T. et al. 1989 and 1990, supra).

Mason, P. W. et al. *J Gen Virol* (1990) 71:2107–2114 identified two domains of the DEN-1 envelope protein: domain I which includes amino acids 76–93 of the E protein and domain II (equivalent to domain B) which includes amino acids 293–402. These domains were identified from deletion analysis using recombinant fusion proteins expressed in *E. coli* and reacted with antiviral monoclonal antibodies. Recombinant fusion proteins containing *E. coli* trpE sequences fused to the envelope protein (amino acids 1 to 412) elicited antibodies in mice which reacted with a portion of the protein containing domain II.

In addition, Mason, P. W. et al. (*J Gen Virol* (1989) 70:2037–2049) expressed a collection of *E. coli* trpE fusion proteins to segments of JE virus envelope protein spanning domain B. The trpE fusion proteins containing the smallest JE E fragments that retained immunoreactivity with a panel of neutralizing monoclonal antibodies included amino acid residues from methionine 303 through tryptophan 396. However, animals immunized with immunoreactive trpE fusion polypeptides did not produce neutralizing antibodies nor were they protected from lethal challenge.

Trirawatanapong, T. et al. Gene (1992) 116:139–150 prepared several truncated forms of dengue 2 envelope proteins in *E. coli* for epitope mapping, and mapped monoclonal antibody 3H5 to its corresponding epitope. This was first localized between amino acids 255 and 422. Targeted gene deletions in the plasmid constructs encoding the truncated proteins permitted mapping of the binding site to the 12 amino acids between positions 386 and 397. The mapping was apparently confirmed by the ability of a synthetic peptide containing E protein amino acids 386–397 to bind 3H5 specifically.

Megret, F. et al. *Virology* (1992) 187:480–491 prepared 16 overlapping fragments of DEN-2 envelope protein as trpE fusion products in *E. coli* for epitope mapping. The fusion proteins are produced intracellularly and obtained from the lysates. These products were used to map epitopes defined by a panel of 20 monoclonal antibodies. Six antigenic domains were described: non-neutralizing antibodies bound to peptides containing amino acids 22–58, amino acids 304–332, amino acids 60–97, and amino acids 298–397. Neutralizing antibodies bound to peptides containing amino acids 60–135, 60–205, and 298–397.

Significantly, Megret et al. (1992, supra) demonstrated that all MAbs (including 3H5), with two exceptions (below), that recognize "full-length" domain B (amino acids 298–397) are unable to recognize slightly shorter polypeptides. For example, in contrast to the findings of Trirawatanapong et al. *Gene* (1992, supra), MAb 3H5 was unable to bind to trpE fusion proteins containing DEN-2 E amino acids 304–397, 298–385, or 366–424. The two exceptional MAbs in the findings of Megret et al. are MAbs 5A2 and 9D12. The pattern of binding of MAb 5A2 suggests that it recognizes a linear epitope between amino acids 304 to 332, while MAb 9D12 binds to a polypeptide, amino acids 298–385, which is slightly shorter than the smallest polypeptide (amino acids 298–397) to which MAb 3H5 binds. These results indicate that both the disulfide bond in domain B and the domain B C-terminal amino acids are involved in forming the immunodominant domain B epitopes.

Although it appears established from the art that the B domain of the flavivirus envelope protein contains epitopes which bind neutralizing antibodies, problems have arisen with respect to producing recombinant polypeptides containing the B domain in a form which mimics the native protein and is thus capable of eliciting an immune response. The only recombinantly produced E polypeptides containing the B domain that elicited a protective immune response in mice were expressed from Vaccinia and baculovirus vectors. Generally, recombinantly produced proteins lack the appropriate glycosylation, folding, and disulfide bond formation for producing a proper immune response.

It has now been found that the B domain of the envelope protein can be successfully secreted from yeast in a form which elicits the production of neutralizing antibodies. This permits, for the first time, the production of a successful recombinantly produced subunit dengue vaccine.

DISCLOSURE OF THE INVENTION

The invention provides vaccines containing, as an active ingredient, a secreted recombinantly produced the dengue envelope protein or a subunit thereof. The vaccines are capable of eliciting the production of neutralizing antibodies against dengue virus. In the illustrations below, the B domain of the envelope protein (E) is secreted from yeast by producing it in an expression vector containing the α-mating factor prepropeptide leader sequence (preproMFα$_L$). Peptide subunits representing 60% E and 80% E are secreted from Drosophila cells using the human tissue plasminogen activator secretion signal sequence for the propeptide (tPA$_L$) or from the homologous premembrane (prM) leader. The secreted products can easily be purified and prepared as a vaccine.

Thus, in one aspect, the invention is directed to a vaccine for protection of a subject against infection by dengue virus. The vaccine contains, as active ingredient, the envelope protein of a dengue virus serotype or a subunit thereof. The E or subunit is secreted as a recombinantly produced protein from eucaryotic cells. The vaccine may further contain portions of additional dengue virus serotype E proteins similarly produced.

In other aspects, the invention is directed to methods to protect subjects against infection by administering the invention vaccines, to antibodies generated in a mammalian subject administered an immunogenic amount of the vaccine; immortalized B cell lines which generate monoclonal antibodies of this type; methods to effect passive immunization by administering the antibodies of the invention; methods to detect the presence or absence of antidengue virus immunoglobulins utilizing the secreted recombinantly produced peptides of the invention and the recombinant materials important in the secretion of the B domain and methods for its production.

BRIEF DESCRIPTION OF THE DRAWINGS

FIG. 1 is a drawing reproduced from Mandl, et al. (supra) showing a model of the envelope protein of flaviviruses.

FIG. 2 (SEQ ID NO:1) shows the partial nucleotide sequence for DEN-2 PR159 S1 mutant strain and differences from the wild-type strain reported by Hahn (1988, supra).

FIG. 3 (SEQ ID NO:2 and SEQ NO:3) shows the partial nucleotide sequence and deduced amino acid sequence of the genome of DEN-2 PR159/S1 strain in comparison with wild-type.

FIG. 4 (Residues 1693–1732 of SEQ ID NO:1 and SEQ ID NO:4 through SEQ ID NO:7) shows the oligonucleotide used to mutagenize an 80% cDNA clone to obtain the domain B coding sequence.

FIG. 7 (SEQ ID NO:8 and SEQ ID NO:9) shows the preproMFα$_L$/domain B fusion protein.

FIG. 10 shows the survival times of mice immunized with recombinant domain B and challenged with Dengue-2.

FIG. 13 shows the survival times of mice immunized with *D. melanogaster* Schneider cell-secreted 80% E.

MODES OF CARRYING OUT THE INVENTION

Figure 5:
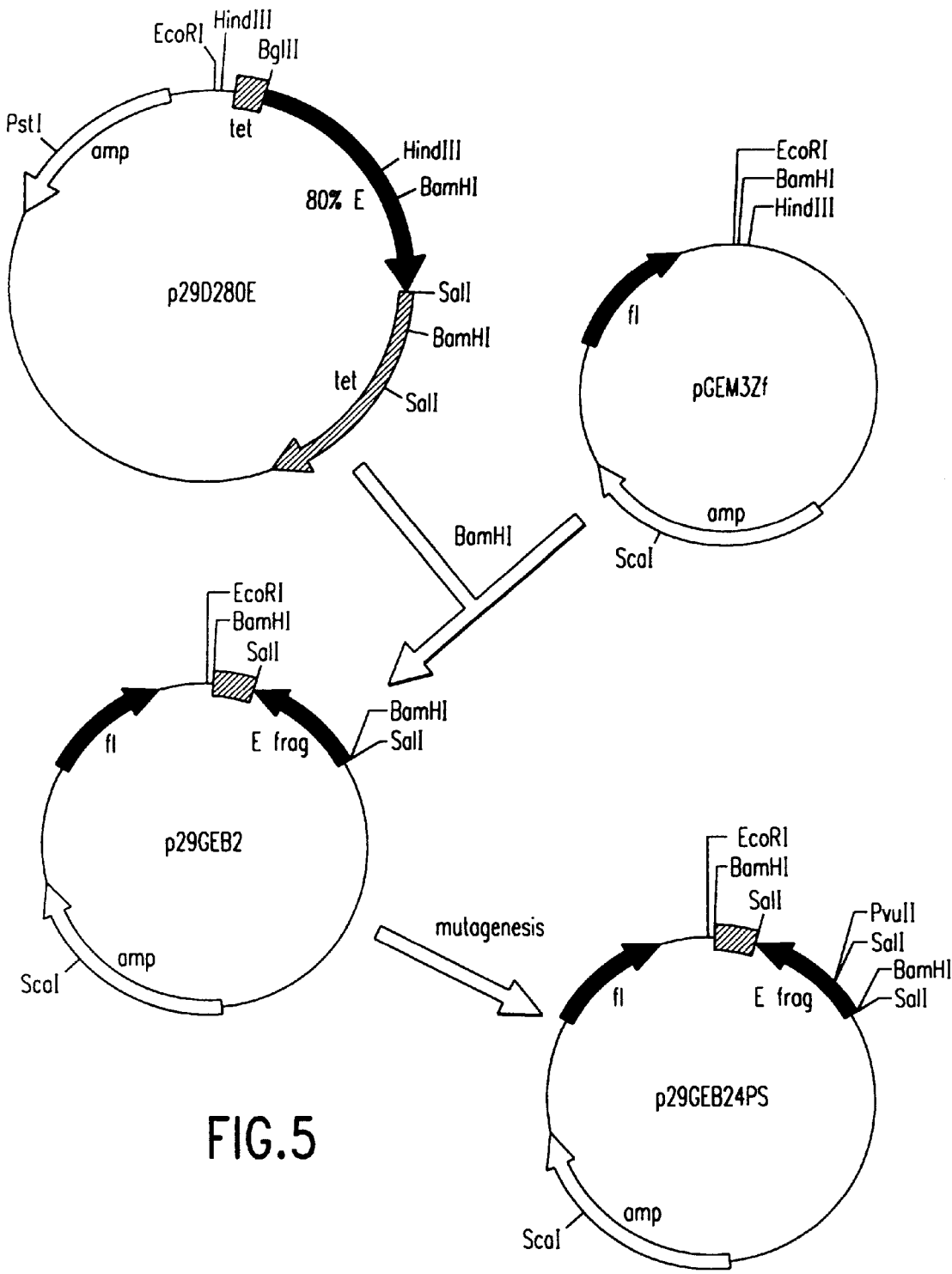
FIG. 5 shows the construction of a cloning vector containing the nucleotide sequence encoding domain B.
Figure 6:
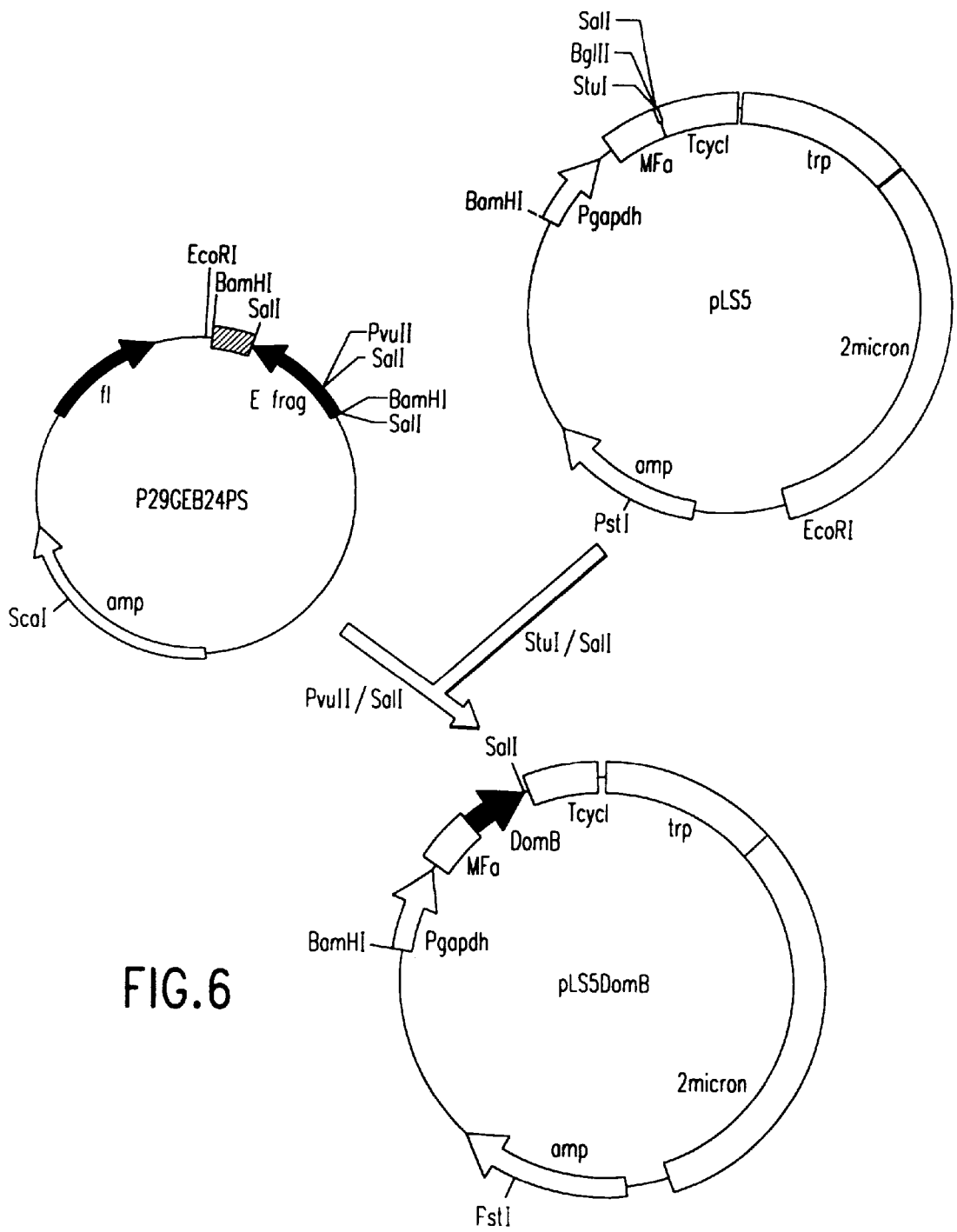
FIG. 6 shows the insertion of the domain B coding sequence into the yeast expression vector pLS5.
Figure 8:
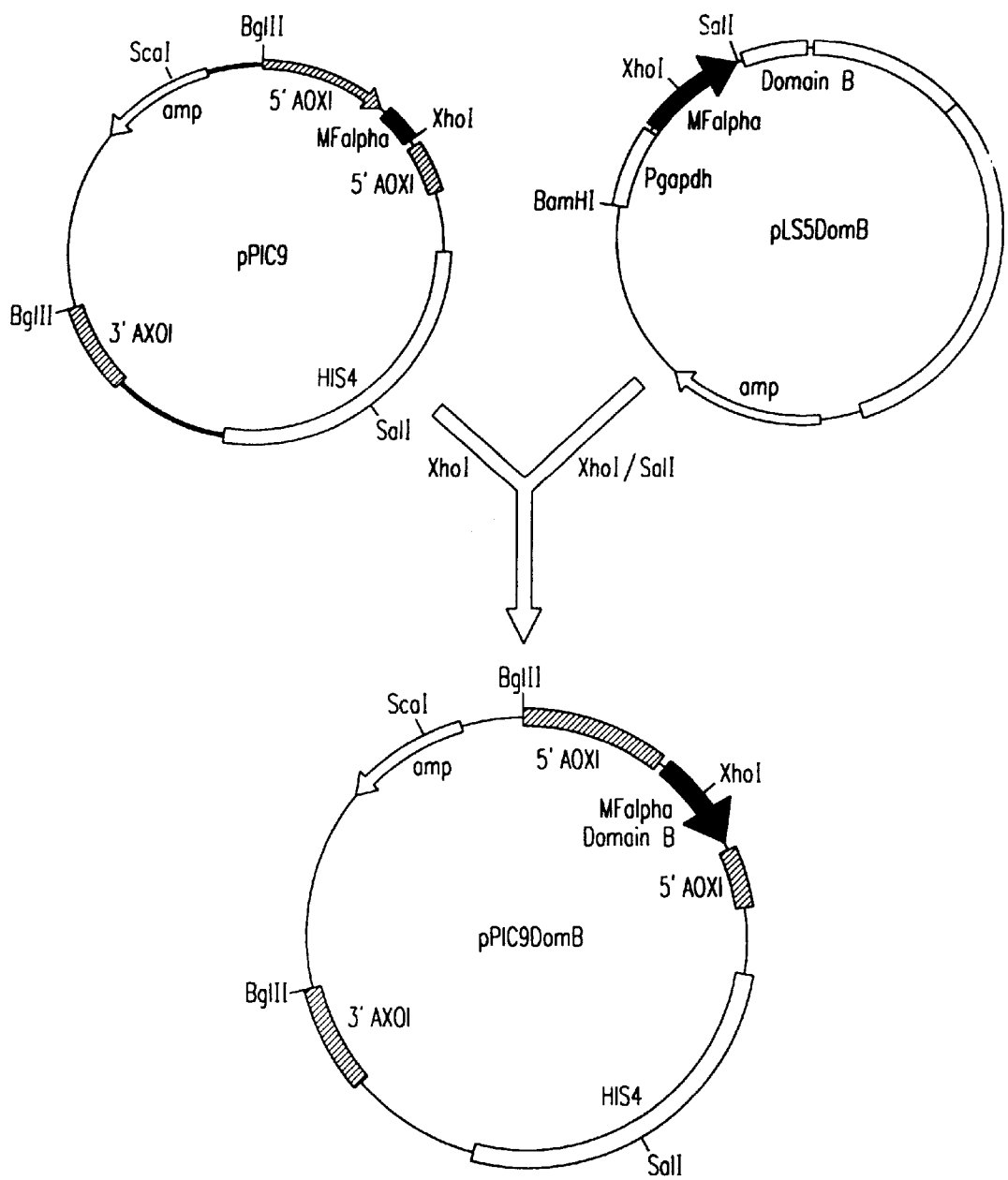
FIG. 8 shows the construction of an expression vector for domain B in Pichia.
Figure 9A:
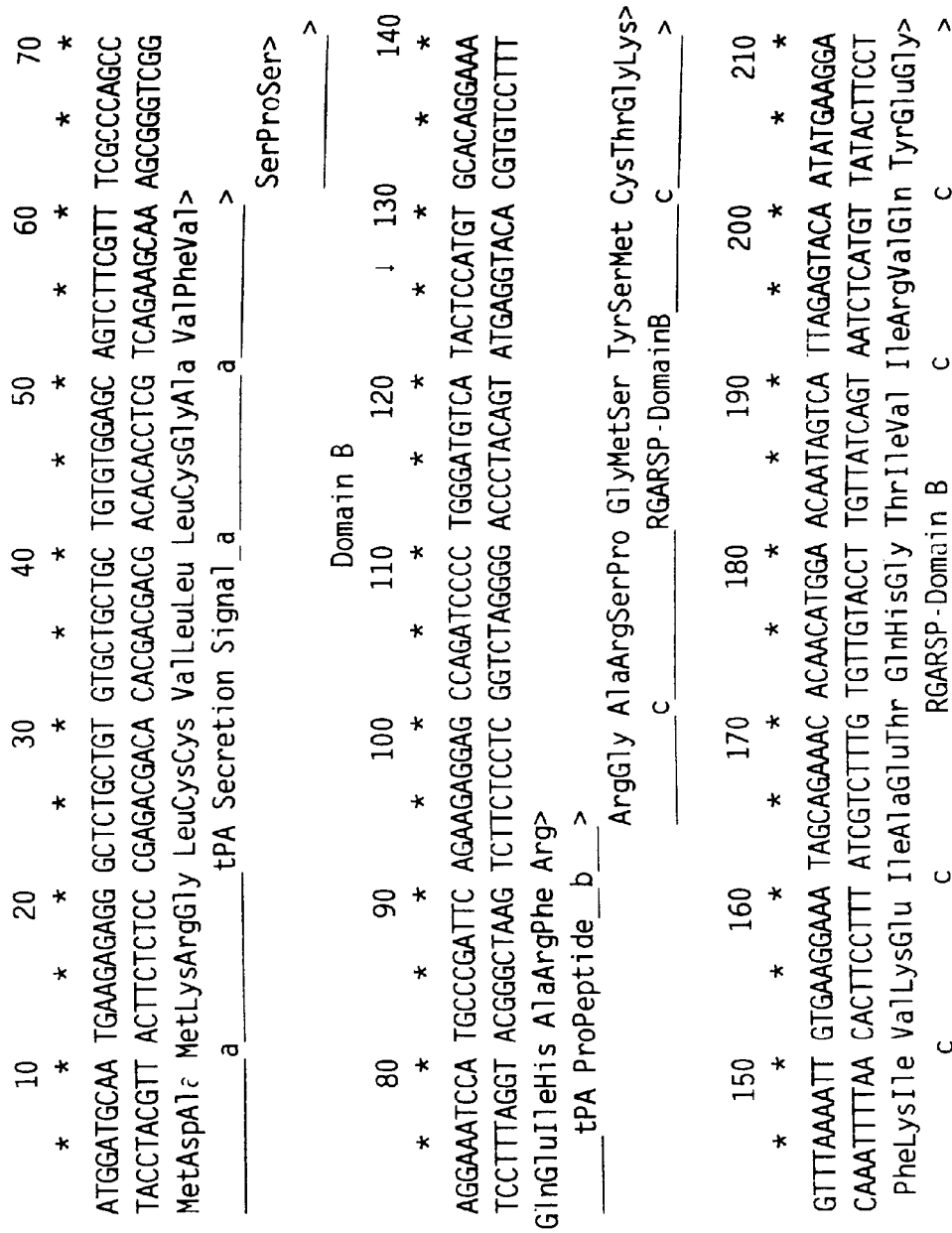
FIG. 9 (SEQ ID NO:10 through SEQ ID NO:12) shows the nucleotide and deduced amino acid sequence for the tPA$_L$-DomB fusion protein.
Figure 11:
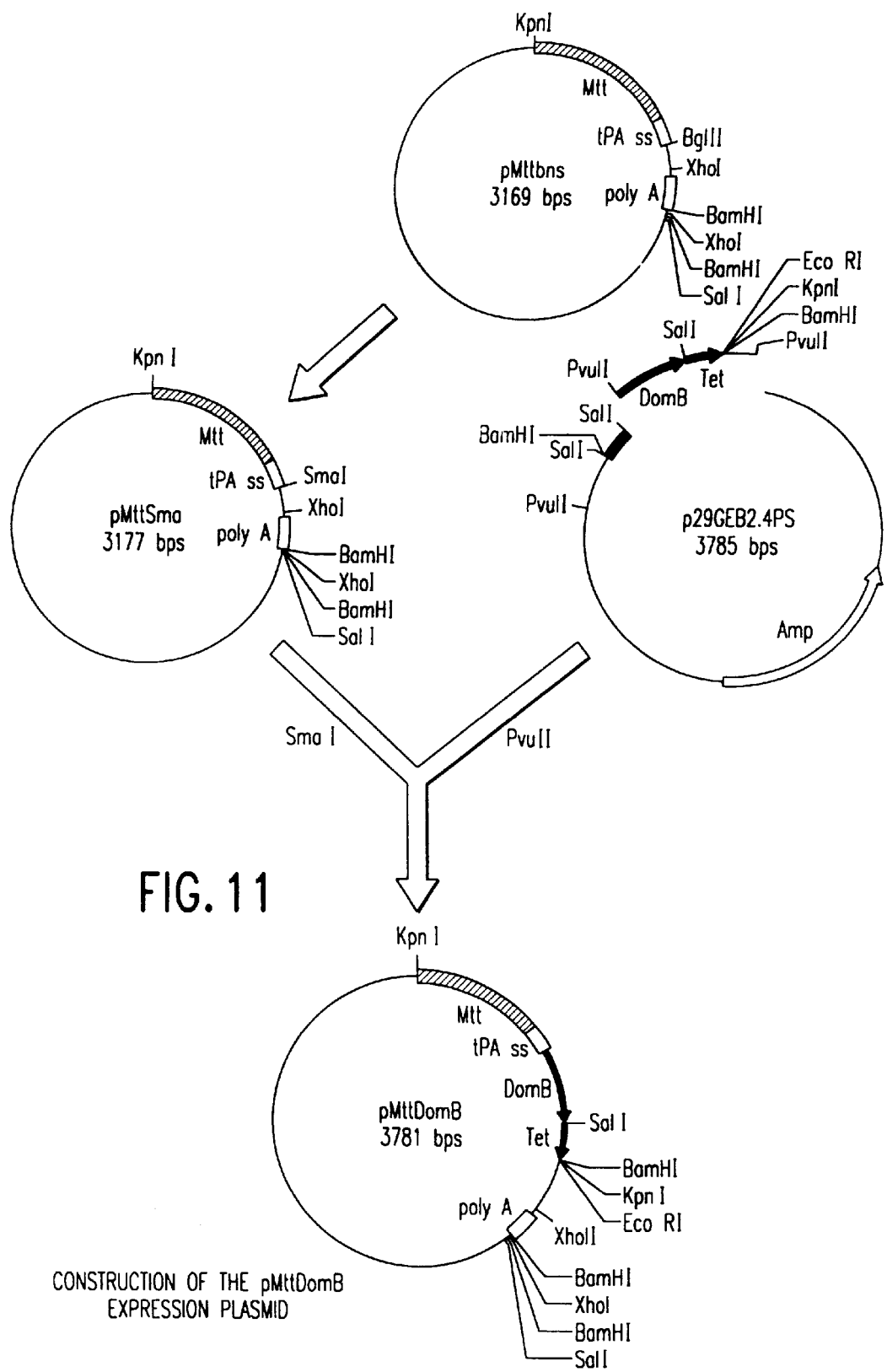
FIG. 11 shows the construction of an expression vector for production of domain B in *Drosophila melanogaster* tissue cultured Schneider cells.
Figure 12:
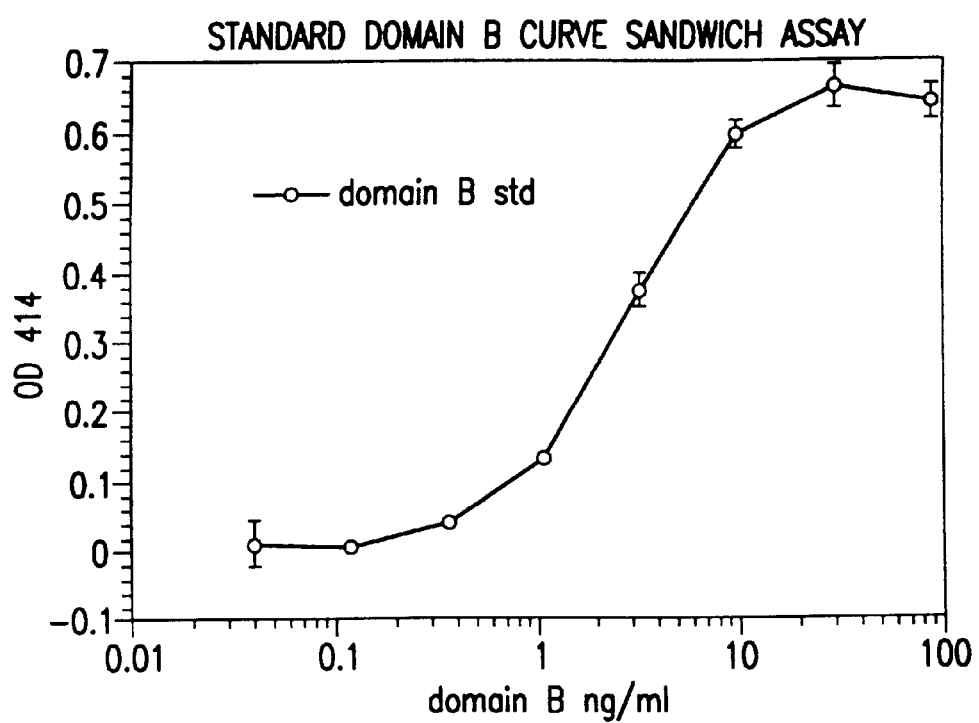
FIG. 12 shows the standard curve for a DomB sandwich assay.

The invention provides, for the first time, a subunit vaccine that can be efficiently produced recombinantly and secreted and that is effective in protecting subjects against infection with dengue virus. Although many attempts have been made to obtain such a subunit vaccine, either the subunit itself is resistant to recombinant production techniques which permit it to be secreted in a processed form so as to render it effective as an immunogen, or, if its recombinant production is facile, it fails to elicit neutralizing antibodies. The present applicants have found that certain portions of the envelope protein of dengue virus type 2, such as domain B representing approximately 100 amino acids of the envelope protein extending approximately from the Gly at position 296 to the Gly at position 395, and optionally including additional E sequence through position 413 of the protein, and other portions of E, i.e., 60% E and 80% E are effectively secreted by certain convenient eucaryotic recombinant hosts, in a form that permits processing to mimic the native conformation of the protein. The secretion of the protein into the culture medium facilitates purification. Furthermore, this form is able, when administered, especially in the presence of adjuvant, to raise neutralizing antibodies in animals. Thus, this subunit represents a useful component of a vaccine for protecting subjects against dengue infection.

As used herein, "B domain" refers to a peptide which spans from approximately Gly 296 to Gly 395 of the DEN-2 envelope protein, and optionally including additional E sequence through position 413 of the envelope protein. These positions are approximate; for example, Mandl (1989, supra) describes the generation of a tryptic fragment containing domain B which spans the amino acids of the TBE E protein from position 301 to 396. The sequences described in the present application represent the envelope protein from dengue Type 2 virus (DEN-2); three additional distinct dengue serotypes have been recognized. Therefore, "Domain B" also refers to the corresponding peptide region of the envelope protein of these serotypes, and to any naturally occurring variants. In addition, B domain includes extended forms of the about 100–120 amino acid peptides, wherein the extensions do not interfere with the immunogenic effectiveness or secretion of the B domain. In one embodiment, such extensions are minimal—i.e., not more than six additional amino acids—at either the N-terminus or the C-terminus, or distributed between these termini; preferably no more than four total additional amino acids, and most preferably no more than two.

The form of domain B which spans positions of about 296–395 is referred to herein as "classical" domain B. When the B domain includes at least portions of the region extending to amino acid 413, the additional region may confer additional functions, e.g., enhancing immunogenicity by providing a helper T cell epitope. The form of domain B which includes positions about 296–413 is referred to herein as DomB+T. The domain B of the invention includes these two specific embodiments, "classical" domain B and DomB+T, as well as those forms which span positions approximately 296 to a position between position 395 and 413.

Other portions of the E protein illustrated below are self-explanatory. 80% E is the N-terminal 80% of the protein from residue 1 to residue 395. 60% E represents the corresponding shorter sequence. These subunits are produced from vectors containing the DNA encoding the mature protein, or along with the prM fusion which results in secretion of the 80% or 60% E per se.

For practical large-scale production of the subunits used as active ingredients in the vaccines of the invention, recombinant techniques provide the most practical approach. However, to be useful as active ingredients, the subunits as produced must assume a conformation and undergo processing under conditions which render them similar to the native envelope portion as it exists in the envelope protein of the virus. In order to achieve this, the recombinant production must be conducted in eucaryotic cells, preferably yeast or Drosophila cells. In addition to the *S. cerevisiae* in *P. pastoris* yeasts illustrated below, other yeasts, such as Kluveromyces sp *Yarrowia lipolytica*, and *Schizosaccharomyces pombe* may be used. Other insect cells besides the *Drosophila melanogaster* Schneider cells illustrated below may also be employed. Additional appropriate eucaryotic cells include mammalian expression cells such as Chinese hamster ovary cells. Other insect cells may also be used in conjunction with baculovirus based vectors. The B domain or 60% E or 80% E must be produced as a correctly processed protein and secreted.

It has been found, as demonstrated hereinbelow, that particularly efficient secretion of biologically active mature protein can be achieved in several ways. First, this can be done by expressing the B domain in yeast in operable linkage with the α-mating factor signal sequence. Constructs which place the nucleotide sequence encoding the B domain disposed so as to encode a fusion protein with an upstream α-mating factor signal sequence are therefore included within the scope of the invention. An additional preferred embodiment employs Drosophila cells and the human tissue plasminogen activator leader sequence for secretion of 60% E or 80% E as well as domain B. Envelope protein subunits that represent N-terminal portions of truncated protein may also be secreted from the homologous prM fusion. Other secretion signal peptides or secretion leader pre/pro peptides, such as those associated with invertase or acid phosphatase of *S. cerevisiae* or with glucoamylase of *C. albicans* or of *A. niger* or the bovine chymosin prepropeptide secretion leader can also be used. Secretion leaders in general that occur at the amino terminus of secreted proteins and function to direct the protein into the cellular secretion pathway generically can be used. In general, the invention includes expression systems that are operable in eucaryotic cells and which result in the formation of envelope protein or a subunit secreted into the medium. Thus, useful in the invention are cells and cell cultures which contain expression systems resulting in the production and secretion of mature B domain.

The properly processed E protein or subunit is recovered from the cell culture medium, purified, and formulated into vaccines. Purification and vaccine formulation employ standard techniques and are matters of routine optimization. Suitable formulations are found, for example, in *Remington's Pharmaceutical Sciences*, latest edition, Mack Publishing Company, Easton, Pa. In particular, formulations will include an adjuvant, such as alum or other effective adjuvant. Alternatively, the active ingredient and the adjuvant may be coadministered in separate formulations.

The active vaccines of the invention can be used alone or in combination with other active vaccines such as those containing attenuated forms of the virus or those containing other active subunits to the extent that they become available. The vaccines may contain only one subunit as an active ingredient, or additional isolated active components may be added. Corresponding or different subunits from one or several serotypes may be included in a particular formulation.

To immunize subjects against dengue fever, the vaccines containing the subunit are administered to the subject in conventional immunization protocols involving, usually, multiple administrations of the vaccine. Administration is typically by injection, typically intramuscular or subcutaneous injection; however, other systemic modes of administration may also be employed. Although the technology is not as well developed, transmucosal and transdermal formulations are included within the scope of the invention as are effective means of oral administration. The efficacy of these formulations is a function of the development of formulation technology rather than the contribution of the present invention.

Since the subunit vaccines containing B domain have been shown to elicit the production of neutralizing antibodies, the antibodies thus raised can themselves be used as passive vaccines. For production of passive vaccine, a suitable mammalian subject is immunized with the E protein or subunit of the invention and antibodies are either recovered directly as a composition from the antisera or indirectly as monoclonal antibodies from immortalized B cells of the subject. For production of monoclonal antibodies, the conventional techniques of Kohler & Milstein, for example, or treatment with Epstein Barr virus, are used in immortalizing peripheral blood lymphocytes or spleen cells and screening for antibodies immunoreactive with the immunogen. These antibodies may further be screened for their ability to effect plaque reduction in infected sera or cultures.

The polyclonal antisera are generally subjected to purification techniques such as standard size separation and chromatographic techniques to obtain purified immunoglobulins. The recombinantly produced proteins of the invention are particularly useful affinity ligands for chromatographic purification. A multiplicity of techniques is available for the purification of immunoglobulins for use in passive vaccines. If monoclonal antibodies are to be purified from small volumes of a medium ascites fluid, a protein A affinity column is particularly useful. For larger volumes, additional standard chemical techniques, such as ammonium sulfate precipitation and DEAE chromatography can be used. These immunoglobulins or the monoclonal antibodies generated by the immortalized B cells are then used in vaccine formulations as is understood in the art.

As is the case with active vaccines, the passive vaccines of the invention may be used in combination with additional antibodies or tandem administration of the antibodies of the invention and additional antibodies may be employed.

In the event that the passive vaccine is intended for use in a species other than that of the subject in which the antibodies were prepared, it may be desirable to modify the antibodies to minimize any immunogenic response. For example, it may be possible to use only the variable regions of these antibodies, such as the $F_{ab}$, $Fab_{ab'}$, or $F_{(ab')_2}$ regions. These fragments can be prepared either from polyclonal antisera or from the supernatants of hybridoma cultures by treating with proteolytic enzymes and recovering the desired fragments. The fragments are readily separated by using the relevant protein of the invention as an affinity reagent.

Alternatively, chimeric antibodies can be produced wherein the constant region corresponding to the species to be protected is substituted for the constant region characteristic of the species of antibody origin. The availability of recombinant techniques makes the production of chimeric antibodies a relatively trivial exercise. Briefly, a hybridoma or cell line producing the antibody of interest is used as a source for the genes encoding the antibody. The genes are recovered from, for example, the hybridoma using standard cloning procedures. The genes are then manipulated in vitro to remove the constant region and replace it with a constant region of a different species origin. The modified genes are then ligated into expression systems and expressed in recombinant host cells, such as CHO cells, monkey cells, yeast cells, and the like.

Further modifications in the variable regions can also reduce immunogenicity. Again, since recovery of the genes encoding the antibody is within the skill of the art, the variable regions, too, can be manipulated to replace the framework regions with framework regions more representative of the desired species, leaving intact the complementarily determining regions responsible for antigen specificity. In still another embodiment, the variable heavy chain and variable light chain regions can be linked through a peptide linker and produced as a single chain $F_v$ molecule.

Thus, if the passive vaccines are intended for humans, the foregoing various techniques of humanizing antibodies can be employed to minimize any immunogenic response even though the original antibodies are raised in nonhuman species.

In addition to use in vaccines or in the generation of passive vaccines, the mature recombinant E protein and subunits of the invention may be used as analytical reagents in assessing the presence or absence of antidengue antibodies in samples. The interest in doing this may be diagnosis of infection with dengue, monitoring response to dengue infection or may simply reside in the use of immunoassays as part of standard laboratory procedures in the study of the progress of antibody formation or in epitope mapping and the like. The antigen is employed in standard immunoassay formats with standard detection systems such as enzyme-based, fluorescence-based, or isotope-based detection systems. Preferably, the antigen is used coupled to solid support or in sandwich assays, but a multiplicity of protocols is possible and standard in the art.

Thus, the secreted protein, such as 60% E, 80% E or B domain may be adsorbed onto solid support and the support then treated with a sample to be tested for the presence of antidengue antibodies. Unbound sample is removed, and any bound antibodies are detected using standard detection systems, for example, by treating the support with an antispecies antibody with respect to the species represented in the sample to be tested, the antispecies antibody coupled to a detection reagent, for example, horseradish peroxidase (HRP). The presence of the HRP conjugated antispecies antibody is then detected by supplying a suitable chromogenic substrate.

Alternatively, the anti-subunit or antidengue antibody may be adsorbed to the solid support and detected by treating the solid support with the recombinant domain B, either directly labeled, or labeled with an additional antibody in a sandwich-type assay.

In addition, both the mature peptides, such as domain B and 60% E or 80% E of the invention and the antibodies immunoreactive with it can be used in standard purification procedures as affinity reagents. Thus, purification of the subunits from recombinantly produced cultures can be effected by affinity columns using antibodies raised against these antigens. Conversely, immunoglobulins useful in passive vaccines can be readily purified from antisera using the peptides of the invention.

The mature domain B or other subunit of the invention may be used to detect the presence or absence of antibodies of various isotypes, including IgG and IgM isotypes. As set forth above, detection of IgM isotypes is significant since this is an index of primary infection.

In the examples below, particular subunits of the dengue Type 2 envelope protein, in particular 60% E, 80% E and domain B are illustrated as representative of effective subunits of the envelope protein. For the 60% E and 80% E constructs in general, secretion can be obtained from constructions designed to express the prME subunit fusion. The mature N-terminus of the envelope protein is then secreted into the culture medium. Whether the N-terminus of the envelope protein subunits were fused to a heterologous leader, such as the human tissue plasminogen activator leader sequence, or to the homologous prM sequence, the mature form of the truncated envelope protein is secreted. The secreted truncated Es are expressed at high levels in Drosophila, efficiently processed, and secreted into the medium. The products are glycosylated and processed to an endo-H resistant form. The secreted form of truncated E produced cotranslationally with prM generally represents about 20–30% of the total protein in the medium. Furthermore, based upon reactivity with conformationally sensitive monoclonal antibodies, using a ELISA and immunofluorescence formats, the secreted E products are shown to have a native conformation. Immunization of mice with crude medium from transformed cells expressing prM truncated E induces a potent virus-neutralizing response.

The following examples are intended to illustrate but not to limit the invention.

EXAMPLE 1

Preparation of Envelope Proteins in *Saccharomyces cerevisiae*

A cDNA clone derived from dengue serotype 2 (DEN-2) described by Hahn, Y. S. et al. *Virology* (1988, supra) was used as the starting material. This cDNA derives from strain PR159/S1. This strain has a small plaque, temperature-sensitive phenotype; the complete sequence of the cDNA derived from the genomic RNA for PR159/S1 is set forth in this publication.

FIG. 2 shows the sequence of the cDNA derived from genomic RNA of DEN-2 PR159/S1 for the Capsid, preMembrane, Envelope, and NS1 genes. Shown in bold at nucleotides 103, 1940, 1991, and 2025 are corrections to the Hahn published sequence. Differences in the S1 sequence from the wild-type sequence are noted above the wild-type sequence. There are no nucleotide differences in the Capsid and preMembrane protein-encoding portions and there are four in the E encoding portion.

FIG. 3 shows the cDNA sequence of DEN-2 PR159/S1 for the Capsid, preMembrane, Envelope, and NS1 genes and the inferred translation of those four genes, which is part of the larger dengue polyprotein. The four differences between wild-type DEN-2 PR159 and the S1 strain are shown above the S1 nucleotide sequence. Also shown is the context of the codons in which the nucleotide differences occur and the encoded amino acid.

In the E gene, three of the four mutations are silent; S1 has G instead of A at position 1314, T rather than G at position 1356, and C rather than T at position 2025. The mutation at position 1858, a G in S1 rather than A, results in a coding change from Ile in wild-type to Val in S1. There is, therefore, a one amino acid difference in the B domain in the S1 strain as compared to wild-type. Although the amino acid substitution conferred by the mutation at 1858 is conservative, mutagenesis studies of other viral structural proteins (Coller, B. G. et al. (1994) *Mutagenesis Studies on the Predicted VP2 E-F Loop of Coxsackievirus B3*, Abstract, 13th Annual Meeting of the American Society for Virology) have demonstrated that even relatively conservative single amino acid changes in surface loops can have profound effects on viral biology, including infectivity and viral stability. Thus, it is not without foundation that the conservative mutation in domain B of DEN-2 PR159/S1 may be involved in the attenuation of this small-plaque, temperature-sensitive variant.

Subsequent determinations on the S1 strain used herein (S1/HBG) showed that the A at position 103 in wild-type was retained in position 103 in S1/HBG and C was substituted for T at position 2025 (a silent mutation). A deduced amino acid sequence from DEN-2 PR159/S1 and differences occurring in the wild-type are shown in FIG. 3.

Various E gene subclones were obtained which represented the amino-terminal 90% of the envelope, 80% of the envelope, 60% of the envelope and classical domain B. Using the assignment of Mandl, C. W. et al. *J Virol* (1989) 63:564–571, classical domain B starts at Gly296 and ends at Gly395. Classical domain B contains only one disulfide bond and is encoded by the sequence following domains A and C. This classical domain B does not contain the potential T cell epitope described by Mandl et al. at its carboxy end which can be included in some forms of the domain B of the invention, e.g., DomB+T.

The portion of the genome that encodes 80% of the envelope protein (80% E) was amplified using the Polymerase Chain Reaction, primers D2E937p and D2E2121m, and plasmid pC8 (Hahn et al. (1988, supra) as template.

In this notation of the primers, the virus serotype is first indicated (D2 for DEN-2), then the corresponding dengue gene—i.e., in this case envelope, E, is noted. Then is noted the number in the dengue cloned sequences of FIGS. 2 or 3 for the first dengue nucleotide in the 5'–3' direction of the oligonucleotide, i.e., using the numbering of Hahn et al. (1988, supra), and finally the notation shows whether the oligonucleotide primes the plus (p) or the minus (m) strand synthesis. The sequence in the primers corresponding to dengue cDNA are written in uppercase letters; nondengue sequence is written in lowercase letters.

preproMF$\alpha_L$ processing would yield a precisely processed domain B. One of these proteases, Kex2p, the gene product of the Kex2 gene, cleaves following dibasic peptides, such as LysArg, LysLys, ArgArg, and ArgLys. A second protease involved, a dipeptidyl amino peptidase, removes GluAla and AspAla dipeptides from the amino terminus after Kex2p processing.

```
D2E937p2
          BglII
5'-cttctagatctcgagtacccgggacc ATG CGC TGC ATA GGA ATA TC-3' (SEQ ID NO:13)
      XbaI   XhoI    SmaI D2E2121m
            SalI
5'-gctctagagtcga cta tta TCC TTT CTT GAA CCA G-3'          (SEQ ID NO:14)
      XbaI        End End
```

The D2E2121m primer placed two stop codons after the 395th codon of E. The 80% E amplified cDNA fragment was digested at the XbaI sites in the cloning adapters and cloned into the NheI site of pBR322 to obtain p29D280E. Double-strand sequence for 80% E was determined, which identified a single silent PCR-introduced mutation at nucleotide 2001 (AAC/Asn to AAT/Asn).

A subclone representing domain B was obtained from the 80% E subclone by oligonucleotide-directed mutagenesis. In the mutagenesis, stop codons and restriction endonuclease sites were inserted between domain C- and domain B-encoding sequences. The stop codons were positioned to terminate domain A+C translation and SalI and PvuII restriction sites were added to facilitate subcloning of domains A+C and domain B fragments, respectively, into yeast expression vectors. As shown in FIG. 4, to avoid a high AT content in the mutagenic oligonucleotide, the stop codons defining the carboxy-terminus of 60% E containing domains A and C were positioned four codons upstream of the beginning of domain B, i.e., following Lys291. The original and altered nucleotide sequences of the mutagenized region and the corresponding amino acid translation are shown in FIG. 4.

To perform the mutagenesis, a 580 bp BamHI fragment spanning domain B from the pBR322-80% E clone p29D280E was subcloned into pGEM3Zf (Promega) to yield p29GEB2. (See FIG. 5.) This BamHI fragment encodes the 3' end of domains A and C and all of domain B. The plasmid obtained following mutagenesis, p29GEB24PS, was confirmed by DNA sequencing. As shown in FIG. 6, the introduced PvuII site permits direct subcloning of domain B cDNA into yeast expression vectors as a fusion with yeast secretion leader.

The cloned cDNA fragments encoding B domain and 80% E were inserted into expression vectors so as to maintain the translational frame of fusions to secretion leaders as described below. The sequence of the fusions were confirmed by DNA sequencing.

EXAMPLE 2

Secretion of Domain B from *Saccharomyces cerevisiae*

The expression vector constructed to secrete classical domain B from *Saccharomyces cerevisiae* to include envelope protein amino acids 296–395 was constructed so that processing by the proteases normally involved in The MF$\alpha$ prepropeptide (MF$\alpha_L$)-domain B fusion was operably linked to the constitutive promoter from the gene (TDH3) encoding glyceraldehyde phosphate dehydrogenase (GAPDH) contained in pLS5 and, alternatively, to the copper sulfate-inducible CUPI gene promoter contained in pLS6. These vectors were provided by SmithKline Beecham. Both contain the MF$\alpha_L$ sequence, and StuI, BglII, and SalI cloning sites, and use the TRP1 gene as a selectable marker. They contain sequences derived from pBR322 to provide an *E. coli* origin of replication, the ampicillin resistance gene, and sequences derived from the 2-micron plasmid of *S. cerevisiae* to enable replication in *S. cerevisiae*. The insertion of the classical domain B coding sequence into the appropriate reading frame in pLS5 was accomplished by digesting pLS5 with StuI and SalI and by digesting p29GEB24PS with PvuII and SalI and gel purifying the small PvuII-SalI domain B fragment and ligating it into the thus opened pLS5 as shown in FIG. 6. A domain B expression vector derived from pLS6 was constructed in a similar manner.

The nucleotide and amino acid sequence of the MF$\alpha_L$-domain B fusion is shown in FIG. 7.

The resulting expression vectors were transfected into spheroplasts of *Saccharomyces cerevisiae* strain GL43 (MATatrplΔl ura3-52 proA::URA3) and transformants were selected by their ability to grow on minimal medium without tryptophan supplementation. *S. cerevisiae* strain GL43 was supplied by SmithKline Beecham. Strain GL43 pLS5-DomB and pLS6-DomB transformants were grown in small (<5 ml) cultures i Casamino acid-supplemented minimal medium, and proteins secreted into the culture medium and cellular proteins were analyzed by Coomassie-stained SDS-PAGE and Western blot. A novel Coomassie-staining band of approximately 12 kD, which was weakly immunoreactive with DEN-2 HMAF, was observed in the culture media of domain B transformants. No novel Coomassie-staining bands and little or no immunoreactive protein not found in negative controls was observed in cellular protein extracts of domain B transformants. When cultured in Casamino acid supplemented minimal medium, comparable levels of domain B were secreted into the medium by pLS5-DomB and pLS6-DomB transformants. About 20% of the total secreted protein was domain B as estimated by the intensity of Coomassie brilliant blue staining of protein in an SDS-PAGE polyacrylamide gel.

The composition of the medium was optimized; when *S. cerevisiae* containing pLS5-DomB were grown in minimal medium (SD) or Casamino acids (Difco)-supplemented minimal medium, the yields of protein were less than when cultured in rich (YEPD) medium. The pLS5-domain B transformant was preferred since this transformant can be cultured in rich medium whereas pLS6-domain B transformants require the use of the less preferred supplemented minimal medium in order to induce with copper sulfate.

The secreted protein was confirmed as domain B having a Glu-Ala dipeptide appendage to the N-terminus, designated herein Glu-Ala-Domain B or Glu-Ala-DomB. For this demonstration, proteins secreted by a pLS5-DomB transformant were separated by SDS-PAGE and electroblotted to Immobilon P membrane (Millipore), and the amino terminal amino acid sequence was determined by microsequencing. That sequence is: $H_2$N-Glu Ala Gly Met Ser Tyr Ser Met Xxx Thr Gly Lys Phe Xxx Val Val (SEQ ID NO:15). The persistence of the GluAla dipeptide indicates that the dipeptidyl aminopeptidase incompletely processed the domain B N-terminus following proteolysis by Kex2p.

EXAMPLE 3

Purification of Domain B

A. Initial Purification Method

Pilot purifications of domain B from *S. cerevisiae* culture medium used size exclusion chromatography on acrylamide Biogel P100.

For these purifications, an *S. cerevisiae* GL43 pLS5-DomB transformant was cultured in minimal medium overnight and then transferred to either Casamino acid-supplemented minimal (SD) medium or rich (YEPD) medium for expression. After culturing at 30° C. for 2–3 days and feeding daily with buffered glucose to final concentrations of 0.4% glucose and 5 mM sodium phosphate (pH 6.7), the cells were pelleted by centrifugation and the medium was clarified by filtration through a 0.45 μm pore filter. The filtered medium was concentrated about 30-fold either by tangential flow or by centrifugal ultrafiltration using Minitan (Millipore) or Centricon (Amicon) devices, and the concentrate was exchanged into PBS azide buffer (2.7 mM KCl, 1.2 mM $KH_2PO_4$, 138 mM NaCl, 4.3 nM $Na_2HPO_4.17H_2O$, 0.02% azide) by diafiltration or dialysis.

In one example, the concentrated secreted proteins from approximately 500 ml of culture of GL43 pLS5-DomB grown in SD plus Casamino acids were loaded onto a 2.5×75 cm Biogel P100 column and domain B was eluted from the column at approximately 1 bed volume. Domain B was pooled based on SDS-PAGE analysis of column fractions. The pooled domain B fractions were brownish in color and could not be decolorized by dialysis. The brown colored preparation also was not immunoreactive in ELISAs. DEAE chromatography of this sample resulted in binding of the brown color and a mostly colorless flow-through containing domain B. For DEAE chromatography, the brown-colored pooled fractions were dialyzed against 0.1 M acetic acid, pH 5.1 and loaded onto a 1.4×15 cm DEAE (Biorad) column. Domain B was eluted using a 0.01 M acetic acid, pH 5.1, 0.1 M NaCl step gradient.

The purified domain B was of high purity as assessed by silver stain on SDS-PAGE. The resulting Glu-Ala-DomB also gained weak reactivity with antidengue mouse polyclonal HMAF and with antidengue MAbs 3H5 and 9D12 in an ELISA format. The reactivities of earlier colorless preparations from smaller cultures were greater than this initial large-scale preparation. For the ELISA, 96-well microtiter plates were coated with domain B by overnight incubation at 4° C. and then blocked with BSA in 50 mM tris-HCl, pH 7.0, 0.15 M NaCl, 0.05% Tween for 1 hour at room temperature. The plates were then treated with either DEN-2 HMAF or monoclonal antibody. Bound antibody was detected with alkaline phosphatase conjugated goat anti-mouse IgG and measured by the increase in optical density at 414 nm using the alkaline phosphatase substrate paranitrophenylphosphate.

The domain B frequently eluted from the Biogel P100 in two equal fractions, the first with the bulk of the secreted yeast proteins and the second as 70–90% pure domain B. Treatment with 1M NaCl, 1 and 2 M urea, and 1% DDAPS, a zwitterionic detergent, were ineffective in completely disaggregating domain B during size exclusion chromatography. Since the domain B of both fractions had the same electrophoretic mobility in the presence of detergent and absence of DTT, this polypeptide was neither covalently cross-linked to another protein nor self-polymerized via disulfide bonds.

B. Improved Purification Method

A standard culture and purification method was developed that has reproducibly yielded immunoreactive domain B expressed and secreted by *S. cerevisiae* GL43 pLS5-DomB. For that method, a primary culture is prepared by inoculating 60 ml of SD medium in a 250 ml baffled flask with a single colony of yeast strain GL43 pLS5-DomB grown on an SD plate. SD medium is prepared by autoclaving 0.67% Bacto yeast nitrogen base without amino acids, cooling and providing 2.0% w/v dextrose and 12 mM $K_2HPO_4$ using autoclave stock solutions. Solid SD medium is prepared by including Bacto agar at 1.8%. The culture is grown at 30° C. for 18–24 hours with shaking at 240 rpm.

Secondary cultures are then grown in 300 ml of SD medium supplemented with 0.2% casamino acids in 2 L baffled flasks. The secondary cultures are inoculated with 30 ml of the primary culture. The secondary cultures are incubated at 30° C. for 18–24 hours with shaking at 300 rpm.

Large-scale tertiary cultures are then prepared by inoculating 1 L of YEPD medium in a 4 L baffled flask with 100 ml of the secondary culture. YEPD is prepared by autoclaving 1% yeast extract plus 2% Bactopeptone, to which sterile dextrose is added to a final concentration of 2% after cooling. The large-scale cultures are incubated at 30° C. for 48 hours with shaking at 300 rpm. After 24 hours, the culture is supplemented with 0.01 vol of sterile 40% w/v glucose and 0.02 vol of sterile 1 M phosphate buffer, pH 6.7.

After growth in the 1 L culture, the cells are removed by centrifugation at 5,000 rpm at 4° C. for 5 min. in a Sorvall GS-3 rotor. EDTA and EGTA are added to final concentrations of 1 nM each to the cleared medium, and the resulting solution is filter sterilized using a 045 μm pore filter membrane (Millipack-20 or Opticap-50, Millipore). Glycerol is added to 10% v/v to the filtrate which is then concentrated 20–30 fold using tangential flow ultrafiltration (Millipore Minitan System) with two membrane cartridges (four regenerated cellulose membranes) of a 10 kD MW cutoff. The retentate is kept on ice during ultrafiltration in the coldroom at 4° C. for about 10–15 hours.

The concentrated medium is directly used or rapidly frozen on dry ice/ethanol in 10 ml aliquots in 15 ml polypropylene or polystyrene tubes with a screw cap and stored at −70° C.

Concentrated medium of the tertiary culture is dialyzed at 4° C. us9ing a membrane with a 6–8 kD cutoff (Spectra/Pore-1 Membrane) against 10 mM acetate, pH 4.5 (4×4 liters; 2–3 hours each; 1 overnight).

For purification, the concentrated, buffer-exchanged medium is loaded onto a 2.5×22 cm CM Biogel A (Biorad) column at 0.8 ml/min. at 4° C. The column is washed with 150–250 ml of 10 nM acetate, pH 4.5 until the optical density at 280 nm of the eluent drops to baseline. Domain B is then eluted with 10 mM acetate, 300 mM NaCl, pH 4.5 at 0.8 ml/min. Fractions of approximately 8 ml are collected and analyzed by SDS-PAGE (15%) and visualized by silver staining. Domain B migrates on the trailing edge of the main peak of eluted material as monitored by 280 nm.

The domain B-containing fractions are pooled and concentrated about 11-fold by centrifugal ultrafiltration using, for example, a Centriprep-10 (Amicon) and loaded onto a 5×60 cm Sephadex G-75 (Superfine, Pharmacia) column at 4° C. The column is eluted using phosphate-buffered saline (PBS: 8 g/l NaCl, 0.2 g/l KCl, 1.44 g/l $Na_2HPO_4$, 0.24 g/l $KH_2PO_4$) at a flow rate of 0.8 ml/min. Nine ml fractions are collected and analyzed by SDS-PAGE as above and by indirect ELISA as above using Mab 9D12.

The Sephadex G-75 fractions containing pure immunoreactive domain B from 2-4 purification runs are concentrated about 50-fold by centrifugal ultrafiltration using a Centriprep-10 (Amicon; final volume 2–5 ml). The pooled material is stored at 4° C.

Glu-Ala-DomB purified as above typically is immunoreactive with the virus-neutralizing monoclonal antibodies 3H5 and 9D12. The above-described culturing and purification protocol has been performed several times with reproducible results. The number of cultures of the above-indicated volumes can be increased, and we have grown simultaneously up to six 1 L tertiary cultures. The culture medium from the multiple cultures is pooled for clarification and concentration, and domain B from the concentrate is purified in batches and pooled following verification of immunoreactivity. The amount of protein in the purified domain B preparations may be quantitated by total amino acid analysis using HCl hydrolysis with on-line ninhydrin reaction and optical detection. Table X presents the yield of protein in purified domain B from four cultures.

TABLE A

Total Protein Yields in Purified Domain B Preparations

| Lot No. | Culture Volume | Final Yield* | Yield mg/l |
|---|---|---|---|
| 198.76 | 850 ml | 4 mg | 4.7 |
| 198.71 | 1500 ml | 35 mg | 23 |
| 244.68 | 5750 ml | 90 mg | 16 |
| 244.190 | 5000 ml | 25 mg | 5 |

*Based on amino acid composition of total protein.

EXAMPLE 4

Production of Domain B in *Pichia pastoris*

In addition to *Saccharomyces cerevisiae* as used in the previous examples, the methylotrophic budding yeast *P. pastoris* was used as a host. The domain B coding sequence was subcloned into the expression vector pPIC9 (Invitrogen, San Diego, Calif.) which contains the alcohol oxidase (AOX1) promoter sequence from *P. pastoris*, the MFα prepropeptide secretion leader from *S. cerevisiae*, the AOX1 transcriptional termination sequence, and the HIS4 gene from *S. cerevisiae* as a selectable marker. To construct pPIC9-DomB, the domain B-encoding XhoI-SalI fragment from pLS5DomB was inserted into XhoI-digested pPIC9 as shown in FIG. 8. XhoI cuts at identical positions within the $MF\alpha_L$-encoding DNA of both pLS5 and pPIC9, and SalI cuts immediately following the translational stop codons following domain B-encoding sequences. After verification by DNA sequence analysis, the expression cassette, consisting of the AOX1 promoter-$MF\alpha_L$-domain B-AOX1 terminator, plus HIS4 was released from pPIC9-DomB by BglII digestion and the linear DNA was transformed into competent *P. pastoris* cells according to the supplier's instructions (Invitrogen, San Diego, Calif.). Transformants were selected for the ability to grow on medium lacking histidine ($His^{\pm}$ phenotype), and specific integration of the transforming DNA at the AOX1 locus was indicated in some transformants by slow growth on medium containing methanol (Mut' phenotype) as the sole carbon source.

The expression and secretion of domain B from eleven *P. pastoris* pPIC9-DomB transformants in 3 ml cultures was surveyed by Coomassie-stained SDS-PAGE analysis. A protein of molecular weight equal to domain B secreted by *S. cerevisiae* was evident in the culture media of ten of the eleven *P. pastoris* transformants. Immunoblots of a comparable polyacrylamide gel demonstrated that the protein secreted by *P. pastoris* pPIC9-DomB transformants was immunoreactive with polyclonal antibodies made to domain B secreted by *S. cerevisiae* (see Example 6). The SDS-PAGE analysis indicated that *P. pastoris* secreted domain B at a level comparable to or higher than that achieved in *S. cerevisiae.*

For further comparison of the secreted expression levels of domain B by *S. cerevisiae* and *P. pastoris*, the *S. cerevisiae* transformant and the two best *P. pastoris* transformants, Nos. 5–8 ($Mut^{\pm}$) and 6–16 (Mut'), were cultured in 100 ml shake flask cultures. *S. cerevisiae* pLS5-DomB was cultured 48 hrs in YEPD medium, and 100 ml precultures of the *P. pastoris* pPIC9-DomB transformants were grown in BMGY medium (1.34% yeast nitrogen base without amino acids, 2% Bacto peptone, 0.4 μg/ml biotin, 1% glycerol, and 100 mM potassium phosphate, pH 6.8) for 24 hrs and then harvested and resuspended ni 25 ml of BMMY heterologous protein-inducing medium (the same as BMGY, except with 0.5% methanol replacing the glycerol) and cultured 48 hrs. Culture media with cells removed by sequential centrifugation and filtration through a 0.45 μm pore size membrane were buffer exchanged by diafiltration into TEEN (10 mM Tris, pH 8.0, 1 mM EDTA, 1 mM EGTA, and 150 mM NaCl). The relative levels of domain B secreted by the three cultures were estimated by size fractionating the proteins in 3, 6, 9, and 12 μl of each sample on a 15% SDS-PAGE gel and staining with Coomassie blue. As estimated by the intensity of Coomassie staining, P. pastoris secreted at least four-fold more domain B per volume of induction culture medium than *S. cerevisiae* in YEPD. Correcting for the four-fold concentration of culture volume of the P. pastoris when transferred into the induction medium, we conclude that *P. pastoris* secretes slightly more than *S. cerevisiae* in shake flask cultures on a per volume basis. However, on a per gram cell dry weight basis, P. pastoris (0.80 gm total cell dry weight) secreted approximately 1.6-fold more domain B than *S. cerevisiae* (1.33 gm total cell dry weight).

EXAMPLE 5

Effect of Extending Domain B

In a manner similar to that set forth in the preceding examples, two plasmid constructs for expression in *S. cerevisiae* were made that include additional domain B-carboxy terminal sequence downstream of amino acid 395 with the domain B coding sequence. One construct, designated DomB+stem, represents Gly296-Gly445 and was expressed as a fusion with the $MF\alpha_L$. This construct includes those sequences that lie between domain B and the transmembrane anchor of E. This region contains a potential T cell epitope (Mandl et al. *J Virol* (1989) 63:564–571) and additional hydrophobic sequences, a peptide from this region elicits virus-recognizing antibodies (Roehrig et al. 1922 in *Vaccines* 92, pp. 2777–2281), and this region may contribute to the proper folding and presentation of the domain B B-cell epitope to the immune system.

The domain B+stem cDNA fragment was constructed in *E. coli* cloning vectors by combining the domain B cDNA fragment and the 3' end of a 90% E clone. As introduced in Example 1, an E gene subclone representing the amino terminal 90% of E was constructed from DEN-2 PR159/S1 cDNA plasmid pC8 of Hahn et al. (1988, supra) using the PCR. The 90% E polypeptide contains all of E except for the C-terminal membrane anchor comprising two transmembrane domains. The 90% E cDNA clone was made as follows. The 90% E fragment was amplified by the PCR using pC8 as template and primers D2E937p and D2E2271m. The sequence of D2E937p is given in Example 1. The sequence of D2E2271m is:

```
D2E2271m
        SalI
5'-gctctagagtcga cta tta CCC GTA GAT TGC TCC G-3' (SEQ ID NO:16)
     XbaI        End End
```

Primer D2E2271m placed two stop codons after Gly445 of #, and the two primers positioned useful restriction enzyme sites at both ends of the fragment. The PCR-amplified 90% E cDNA fragment was made blunt at both ends and cloned into the SmaI site of a modified pUC13 cloning vector, yielding pVZ90E.

Combining domain B and the 90% E 3' end made use of a unique AflIII restriction enzyme site found in most pUC-like cloning vectors and a unique AflIII site in domain B sequences. This combining was accomplished by first subcloning the 90% E fragment from pVZ90E into pBluescript to reverse the orientation of 90% E relative to the vector sequences, yielding pBS90E. Then, p29GEB24PS, containing domain B sequences in PGEM (Example 1), and pBS90E were digested with AflIII, and the vector-domain-B5' fragment and the domain-B3'-stem-vector fragment from the two digestions, respectively, were purified, ligated, and recovered in *E. coli* yielding pBS-Bstem.

For expression in *S. cerevisiae*, the PvuII-SalI domain B+stem fragment from pBS-Bstem was subcloned into the pLS5 yeast expression vector at its StuI and SalI sites, putting the MF$\alpha_L$ and B+stem in translational frame. The sequence of the ligated junctions were verified by DNA sequence determination. The domain B+stem expression vector, pLS5-BStem, was transformed into *S. cerevisiae* strain GL43. The resulting transformants grew more slowly than did transformants with pLS5-DomB containing classical DomB and the plasmid appeared to be rapidly lost during growth under nonselective conditions. The DomB+stem product may be toxic to the cells, and the hydrophobicity of the stem may inhibit secretion.

However, a similar construct representing Gly296-Ala413 analogously inserted into pLS5 resulted in substantial amounts of secreted domain B protein. This form of domain B, designated herein DomB+T, contains the downstream T cell epitope. As stated above, the DomB proteins of the present invention include classical DomB and all or part of the amino acid sequence downstream from Gly395 to the Ala residue at position 413.

The DomB+T cDNA fragment was amplified by the PCR from pC8 plasmid DNA using oligonucleotide primers D2E1822p and D2E2175m. The primer sequences are:

D2E1822p KpnI XhoI

5'-cta gcg gta ccc tcg aga AAA GGG AGG CCG GGA TGT CAT ACT CCA TGT GC-3'(SEQ ID NO:17)

D2E2175m SalI NotI

5'-cgt gtg tcg acg cgg ccg cta tta GGC CAT TCT TTT CGC TCC-3'(SEQ ID NO:18)

The PCR product was cloned into pUC18 following KpnI and SalI digestion of the product. The DomB+T cDNA fragment was then released from pUC18-DomB+T by XhoI-SalI digestion and cloned into the XhoI site in pLS5 within the MF$\alpha_L$ and Gly395 of domain B+T. *S. cerevisiae* strain GL43 secrets approximately ten-fold more domain B than domain B+T.

EXAMPLE 6

Preparation of Antibodies to the Recombinant Domain B Protein

The Glu-Ala-DomB peptide which had been column-purified, denatured by heating in SDS, and reduced by treatment with DTT was used to immunize Swiss Webster mice following removal of the excess SDS. The mice yielded high-titre antibodies that were highly immunoreactive when used to probe Western blots displaying the same antigen or DEN-2 viral envelope protein.

EXAMPLE 7

Recombinantly Produced Glu-Ala-Domain B in ELISA Assays

The serological diagnosis for dengue infection is based on the detection of anti-dengue IgM and IgG in primary and secondary viral infection using standard Enzyme Linked Immunosorbent Assay (ELISA) techniques. Current assays are based on the ability of anti-dengue immunoglobulins to recognize semi-purified virus. Primary and secondary infections can be distinguished by the IgM:IgG ratios. (Innis et al., 1989; Kuno et al., 1991).

The recombinantly produced Glu-Ala-domain B purified as in paragraph B of Example 3 was tested as an antigen preparation in both IgM and IgG tests. In these ELISAs, the antigen was coated on plates, followed by sera positive for dengue antibodies and then detection by goat antihuman antibody.

Microtiter plates were coated overnight at 40° C. with 100 $\mu$l of a 5 $\mu$g/ml solution of domain B. After blocking with 3% normal goat serum, primary infected dengue 2 positive serum at a 1:100 dilution was added per well. The bound IgM was detected by the addition of goat anti-human IgM (Fc) conjugated to horseradish peroxidase. Under these conditions, the recombinant Glu-Ala-domain B did not provide positive results.

For IgG, high titer secondary dengue 2 infected sera were supplied at a 1:270 dilution and detected with goat anti-human IgG (Fc) conjugated to horseradish peroxidase. Two of the five sera gave positive reactions in this assay.

The recombinant Glu-Ala-domain B purified by the improved procedure of Example 3 is not recognized by murine polyclonal hyperimmune ascitic fluid (HMAF) to other dengue serotypes and to other flaviviruses, when assayed using a similar ELISA format. Flavivirus infected murine sera tested include, Japanese Encephalitis virus, Tick-Borne Encephalitis virus, Yellow Fever virus, Saint Louis Encephalitis virus, West Nile virus, three viral isolates of dengue serotype 1, two viral isolates of dengue serotype 3, and two viral isolates of dengue serotype 4.

Sandwich assay for the detection of any domain B-containing envelope antigen.

In an alternative enzyme immunoassay format, anti-domain B or anti-Dengue capture antibody, polyclonal or monoclonal, may be absorbed to the solid support, and sample containing an unknown quantity or serotype of dengue antigen may be added and then detected by reacting with a second anti-domain B or anti-Dengue antibody, either conjugated to a signal-generating enzyme or to be detected using a appropriate signal generating system, of which there are a multitude. This immunoassay is useful for the quantitation of recombinantly produced envelope protein or whole virus by comparing the immunoreactivity of a known concentration of domain B with that of the unknown antigen preparation. In addition, the conformational sensitivity or epitope binding site of the anti-domain B capture antibody can be varied to garner additional information regarding the conformation of dengue protein in the preparation.

To perform the sandwich enzyme immunoassay, 100 μl of anti-Dengue monoclonal antibody 9D12 or 3H5 (Henchal, E. A. et al., *Am J Trop Med Hyg* (1985) 34:162–169) was used to coat microtiter wells. The monoclonal antibodies were purified by Protein-A affinity chromatography and used at 10 μg/ml concentration (diluted in PBS: 50 mM sodium Phosphate, pH 7.0, 0.15 M NaCl). After a one hour incubation, the wells were washed three times with TBS-T (50 mM Tris-HC1 PH 7.0, 0.15 M NaCl, 0.05% Tween-20), and blocked with 200 μl/well of 1% BSA in PBS for 1 hour at room temperature. Following three washes with TBS-T, 100 μl per well of a standard purified solution of domain B or an unknown sample was added to each well and captured by the bound monoclonal antibody. The domain B solution was allowed to bind the antibody for one hour at room temperature, and after three washes with TBS-T, 100 μl of Protein A affinity purified polyclonal rabbit anti-domain B serum (25 μg/Ml) diluted in PBS-T (PBS, 0.25% BSA, 0.05% Tween-20) was added to each well and allowed to bind to the bound antigen. Following three washes with TBS-T, 100 μl of alkaline phosphatase-labeled goat anti-rabbit IgG+IgM (H and L) conjugate (Caltag) diluted 1:2500 in PBS-T (previously established by titration) was added to each well. After incubation for one hour at room temperature, the plates were washed four times with TBS-T and 200 μl/well of 1 mg/ml p-nitrophenylphosphate (pNPP) substrate in alkaline phosphatase substrate buffer (25 mM Trizma base, pH 9.5, 0.15 M NaCl, 5 mM $MgCl_2$; 0.02% $NaN_2$) was added. The plates were incubated for one hour at room temperature and the absorbance of each well was measured on a Dynatech MR5000 using a sample wavelength of 410 nm and a reference wavelength of 630 nm. A typical domain B standard curve is presented in FIG. 12.

EXAMPLE 8

Immunization of Mice to Raise Neutralizing Antibodies

A. Crude DomB Immunogenicity in Mice: Media from yeast cultures secreting DomB and a negative control yeast culture were buffer-exchanged with PBS, and total secreted proteins were concentrated for injection into mice. Six groups of five mice each (Outbred Swiss strain, Simonsen) were inoculated with the crude DomB preparation, negative control secreted protein, or saline, as listed below.

| Group | Immunogen | Adjuvant |
|---|---|---|
| I | Saline | Freung's |
| II | Saline | none |
| III | control medium | Freund's |
| IV | control medium | none |
| V | DomB medium | Freund's |
| VI | DomB medium | none |

Primary immunizations consisted of 50 μg of the immunogen diluted in phosphate buffered saline, with or without complete Freund's adjuvant as indicated above. Three boosts of 25 μg each were delivered at two-week intervals with no adjuvant (Groups II, IV, and VI) or Freund's incomplete adjuvant (Groups I, III, and V). Test bleeds were obtained one week after the first and second boosts, and the mice were bled out one week after the third boost.

Western blot and ELISA analysis of the first test bleeds confirmed a strong immune response to DomB among the Group VI (DomB, no adjuvant) mice. After the second bleed, this response was found to be titratable to greater than 1:6,400 by ELISA. Group VI was the only group that developed high titer DomB antibodies. The mice immunized with DomB in Freund's adjuvant (Group V) mounted a weak immune response; based on reactivity to the immunogen in Western blot format and DomB-ELISA antibody titers in the 100–400 range, Group V mice appeared to be immunosuppressed. The control mice (Groups I–IV) were all negative for antibody to DomB in both the Western and ELISA screens. In spite of high DomB antibody titers in Group VI mice, plaque reduction neutralization tests (PRNT) revealed that none of the mice immunized with the crude DomB produced neutralizing antibody (Table 1).

TABLE 1

Plaque Reduction Neutralization Tests of Sera from Mice Immunized with DomB in Concentrated, Total Secreted Yeast Proteins

| Group | Trial | Dilution<br>Plaque Counts | | | | | |
|---|---|---|---|---|---|---|---|
| PBS + | | 1:100 | 1:200 | 1:400 | 1:4 | 1:8 | 1:16 |
| Freund's | 1 | 109, 105 | ~100 | ~100 | | | |
| Aduvants | 2 | | | | 34, 33 | 38, 30 | 44, 44 |
| PBS | | 1:10 | 1:20 | 1:40 | 1:4 | 1:8 | 1:16 |
| | 1 | 100, 106 | ~100 | ~100 | | | |
| | 2 | | | | 29, 33 | 33, 40 | 39, 37 |

TABLE 1-continued

Plaque Reduction Neutralization Tests of Sera from Mice
Immunized with DomB in Concentrated, Total Secreted Yeast Proteins

| Group | Trial | Dilution | | | | | |
|---|---|---|---|---|---|---|---|
| | | Plaque Counts | | | | | |
| Negative | | 1:10 | 1:20 | 1:40 | 1:4 | 1:8 | 1:16 |
| secreted | 1 | 106, 95 | ~100 | ~100 | | | |
| proteins + | 2 | | | | 40, 35 | 37, 39 | 39, 47 |
| Freund's | | | | | | | |
| Negative | | 1:10 | 1:20 | 1:40 | 1:4 | 1:8 | 1:16 |
| secreted | 1 | 109, 94 | ~100 | ~100 | | | |
| proteins | 2 | | | | 38, 42 | 44, 40 | 45, 42 |
| Crude | | 1:10 | 1:20 | 1:40 | 1:4 | 1:8 | 1:16 |
| DomB + | 1 | 100, 92 | ~100 | ~100 | | | |
| Freund's | 2 | | | | 37 ± 5* | 35 ± 6* | 39 ± 3* |
| Crude | | 1:10 | 1:20 | 1:40 | 1:4 | 1:8 | 1:16 |
| DomB | 1 | 105, 91 | ~100 | ~100 | | | |
| | 2 | | | | 39 ± 3* | 41 ± 3* | 39 ± 3* |
| DEN-2 | | 1:100 | 1:200 | 1:400 | 1:800 | 1:1600 | 1:3200 |
| HMAF | 1 | 0, 0 | 0, 0 | 0, 0 | 11, 8 | 31, 19 | 81, 75 |
| | | | | | 1:250 | 1:1000 | 1:4000 |
| | 2 | | | | 3, 6 | 12, 15 | 21, 21 |

PRNT assays performed on VERO cells (Trial 1) or BHK-21 C15 cells (Trial 2) with DEN-2 NGC strain. All plaque counts indicate the number of plaques obtained with the sera from five animals were pooled and assayed in duplicate, except those indicated (*) where each serum sample was individually assayed in duplicate and the number of plaques averaged (mean ± SD).

B. Pure DomB Immunogenicity in Mice: In contrast to mice immunized with crude DomB, outbred ICR mice (Charles River) immunized with purified DomB demonstrated high titer DEN-2 virus neutralizing antibodies. Purified DomB, at a concentration of 3.5 mg/ml, was used to immunize mice (three per group) with 175 µg of purified DomB mixed 1:1 with Freund's adjuvant, with alum, or without adjuvant (PBS). Test bleeds taken after three inoculations were assayed by PRNT (Table 2).

purified DomB in combination with Freund's adjuvants had a high PRNT titer (80T PRNT >1:320).

Three groups of 3 mice each, 5–6 week-old outbred ICR strain (Charles River) were used. Inoculation was intramuscularly in the rump at one site using 10 µg of antigen in 0.1 ml administered solution. Three inoculations were given to each group on days 1, 20, and 43. In one group, inoculation on day 1 incorporated complete Freund's adjuvants, on day 20 incomplete Freund's adjuvant, and that at day 43, no

TABLE 2

Plaque Reduction Neutralization Tests of Sera
from Mice Immunized with Purified DomB

| Group | Trial | Dilution | | | | | | 80% PRNT Titer$^{-1}$ |
|---|---|---|---|---|---|---|---|---|
| | | Plaque Counts | | | | | | |
| Negative | | 1:10 | 1:20 | 1:40 | | | | |
| Ascites | 1 | 36, 40 | 35, 34 | 40, 38 | | | | |
| Fluid | 2 | 39, 38 | 47, 45 | 41, 44 | | | | |
| DEN-2 | | 1:100 | 1:200 | 1:400 | 1:800 | 1:1600 | 1:3200 | |
| HMAF | 1 | 0, 0 | 0, 0 | 1, 0 | 2, 1 | 8, 9 | 13, 14 | 1500 |
| | 2 | 0, 1 | 1, 0 | 1, 2 | 1, 1 | 7, 6 | 16, 17 | >1600 |
| DomB | | 1:10 | 1:20 | 1:40 | 1:80 | 1:160 | 1:320 | |
| no | 1 | 36, 29 | 28, 36 | 29, 27 | 36, 30 | 40, 25 | 28, 31 | >10 |
| adjuvant | 2 | 9, 17 | 20, 15 | 22, 26 | 33, 26 | 41, 36 | 42, 47 | ~10 |
| DomB | | 1:10 | 1:20 | 1:40 | 1:80 | 1:160 | 1:30 | |
| alum | 1 | 8, 6 | 10, 9 | 10, 12 | 21, 20 | 32, 26 | 30, 28 | 10 |
| | 2 | 1, 0 | 5, 4 | 8, 7 | 12, 15 | 20, 25 | 27, 35 | 40 |
| DomB | | 1:40 | 1:80 | 1:160 | 1:320 | 1:640 | 1:1200 | |
| Freund's | 1 | 0, 0 | 1, 0 | 1, 4 | 9, 2 | ND | ND | >320 |
| | 2 | 0, 0 | 3, 4 | 5, 5 | 5, 20 | 13, 9 | 23, 20 | ~640 |

PRNT assays performed on VERO cells with DEN-2 NGC strain. ND = Not Determined.

Mice immunized with purified DomB in the absence of adjuvant lacked neutralizing antibodies. DomB administered in combination with alum elicited low titer (80T PRNT~1:10) neutralizing antibodies, and mice receiving adjuvant. In a separate group, no adjuvant was supplied and in a third group, alum was supplied with all three inoculations. The sera were withdrawn on day 57 and the sera from each group were pooled, heat-inactivated at 56° C. for 30 minutes and tested for their ability to reduce plaques formed from VERO cells.

C. DomB Protection from Virus Challenge: Suckling mice were immunized with purified DomB in Freund's, Alum, Hunter's TiterMax (Vaxcel), or no adjuvant for protection against an intracerebral injection of DEN-2 New Guinea C (NGC) strain. DomB administered in all adjuvants conferred comparable moderate survival against dengue virus challenges although survival was statistically significant (P<0.5 G test) only for mice immunized with DomB and Hunter's TiterMax. The results are shown in FIG. 10.

D. KLH-DomB Immunogenicity in Mice: Two series of mouse immunizations were initiated to determine the 50% effective immunizing dose ($EID_{50}$) of unconjugated and KLH-conjugated DomB. Effects of alum and Freund's adjuvants to a no-adjuvant control are compared.

DomB was conjugated to KLH via EDC (1-ethyl-3-(3-dimethylaminopropyl) carbodiimide HCl) using the carbodiimide coupling method at a 1.5:1 DomB-to-KLH mass ratio. The amount of unconjugated and conjugated DomB used for these immunizations was normalized, relative to the amount of unconjugated DomB. This normalization was based upon the specific immunoreactivity of each preparation as assayed by indirect ELISA.

Mice were immunized with the priming does of 174, 52, or 5.2 μg (total protein) of the KLH-conjugated DomB in Freund's, alum, or no adjuvant. Additional mice were immunized with 87, 26, or 2.6 μg (total protein) of unconjugated DomB in Freund's adjuvant to allow direct comparison of conjugated and unconjugated material. Boosts consisting of one-half the priming dose are being given at two-week intervals. Test bleeds are assayed for the induction of anti-DomB antibodies by ELISA and Western blot. Final bleeds are tested for induction of a neutralizing immune response by PRNT assay as well as for the production of binding antibodies by ELISA and Western blot. The results are summarized in Table 3.

The response to unconjugated DomB with Freund's adjuvants was low compared to the results in Table 2, which had shown that unconjugated DomB induced a strong virus neutralizing response in outbred ICR mice when administered with Freund's adjuvants. This apparent difference may be grounded in testing pooled sera for the data in Table 2. Pooling sera may mask individual variability. The variability in Table 3 may be attributed to the limited epitopes in DomB and to differences in the MHC genes for the outbred Swiss mice used in Table 3.

TABLE 3

Mouse Immune Response to Unconjugated and KLH-Conjugated Purified Domain B

| mouse | antigen | Adjuvant | Final Titer Western[c] | Final Titer ELISA[c] | Final Titer $PRINT_{80}$[c] |
|---|---|---|---|---|---|
| 1 | saline | none | N/T[a] | <1:100 | N/T |
| 2 | | | N/T | <1:100 | <1:10 |
| 3 | | | N/T | <1:100 | <1:10 |
| 4 | 87 μg B | none | N/T | <1:100 | <1:10 |
| 5 | | | N/T | <1:100 | N/T |
| 6 | | | N/T | <1:100 | <1:10 |
| 7 | 87 μg B | Freund's | >1:100,000 Dblt[b] | >1:102,400 | 1:40 |
| 8 | | | N/T | <1:100 | <1:10 |
| 9 | | | 1:1,000,000 Dlbt | >1:409,600 | <1:10 |

TABLE 3-continued

Mouse Immune Response to Unconjugated and KLH-Conjugated Purified Domain B

| mouse | antigen | Adjuvant | Final Titer Western[c] | Final Titer ELISA[c] | Final Titer $PRINT_{80}$[c] |
|---|---|---|---|---|---|
| 10 | | | N/T | <1:100 | <1:10 |
| 11 | | | 1:100,000 Dblt | 1:25,600 | <1:10 |
| 12 | 26 μg B | Freund's | N/T | <100 | <1:10 |
| 13 | | | 1:100,000 Dblt | 1:102,400 | <1:10 |
| 14 | | | 1:10,000 Dblt | 1:102,400 | N/T |
| 15 | | | 1:10,000 Dblt | >1:25,600 | <1:20[c] |
| 16 | | | 1:10,000 Dblt | 1:409,600 | <1:10 |
| 17 | 2.6 μg B | Freund's | 1:1,000 Dblt | 1:25,600 | <1:10 |
| 18 | | | N/T | <1:100 | <1:46 |
| 19 | | | N/T | <1:100 | <1:48 |
| 20 | | | N/T | <1:100 | <1:24 |
| 21 | | | N/T | <1:100 | <1:10 |
| 22 | "87 μg" KLH-B | none | N/T | 1:100 | <1:10 |
| 23 | | | <1:100 | 1:400 | <1:24 |
| 24 | | | N/T | <1:100 | <1:24 |
| 25 | | | N/T | <1:100 | <1:24 |
| 26 | | | N/T | <1:100 | <1:20 |
| 27 | "26 μg" KLH-B | none | N/T | <1:100 | <1:34 |
| 28 | | | N/T | <1:100 | <1:70 |
| 29 | | | N/T | <1:100 | <1:34 |
| 30 | | | N/T | <1:100 | N/T |
| 31 | | | N/T | <1:100 | <1:10 |
| 32 | "2.6 μg" KLH-B | none | N/T | <1:100 | N/T |
| 33 | | | N/T | <1:100 | <1:10 |
| 34 | | | N/T | <1:100 | <1:10 |
| 35 | | | N/T | <1:100 | <1:10 |
| 36 | | | N/T | <1:100 | <1:10 |
| 37 | "87 μg" KLH-B | Freund's | N/T | >1:1,600 | 1:20 |
| 38 | | | N/T | >1:100 | <1:10 |
| 39 | | | N/T | <1:100 | <1:10 |
| 40 | | | 1:1,000 | >1:1,600 | 1:20 |
| 41 | | | N/T | <1:100 | <1:10 |
| 42 | "26 μg" KLH-B | Freund's | 1:10,000 Dblt | >1:25,600 | 1:10 |
| 43 | | | 1:10,000 Dblt | >1:25,600 | 1:2560 |
| 44 | | | 1:10,000 Dblt | >1:25,600 | 1:5120 |
| 45 | | | N/T | <1:100 | <1:10 |
| 46 | | | N/T | 1:100 | <1:10 |
| 47 | "2.6 μg" KLH-B | Freund's | N/T | <1:100 | <1:10 |
| 48 | | | N/T | <1:100 | <1:10 |
| 49 | | | <1:50 | 1:6,400 | <1:10 |
| 50 | | | N/T | <1:100 | <1:10 |
| 51 | | | <:50 | 1:25,600 | <1:10 |
| 52 | "87 μg" KLH-B | Alum | <1:100 | <1:400 | 1:60 |
| 53 | | | N/T | <1:100 | <1:10 |
| 54 | | | <1:100 | >1:1,600 | 1:320 |
| 55 | | | <1:100 | >1:1,600 | 1:80 |
| 56 | | | 1:1000 | >1:6,400 | 1:640 |
| 57 | "26 μg" KLH-B | Alum | N/T | >1:100 | <1:10 |
| 58 | | | N/T | <1:100 | <1:10 |
| 59 | | | N/T | <1:100 | <1:10 |
| 60 | | | N/T | <1:100 | <1:10 |
| 61 | | | N/T | <1:100 | <1:10 |
| 62 | "26 μg" KLH-B | Alum | <1:100 | 1:1,600 | 1:120 |
| 63 | | | 1:1000 | >1:1,600 | 1:120 |
| 64 | | | N/T | <1:100 | <1:10 |
| 65 | | | 1:100 | >1:1,600 | 1:80 |
| 66 | | | N/T | <1:100 | <1:10 |

[a]N/T - not tested
[b]Dblt - a doublet at approximately 12 kD
[c]If serum was insufficient for testing at 1:10 dilution then higher initial dilutions were used and are indicated.

E. DomB Immunizations for Hybridoma Generation: Six BALB/c mice were immunized with 87 μg of unconjugated DomB or 174 μg KLH-conjugated DomB in Freund's adjuvant. Upon demonstration of a strong anti-DomB response, the mice are sacrificed and their spleen cells fused to hybridoma cells for monoclonal antibody production.

EXAMPLE 9

Production of Domain B in Drosophila

The cloning vector p29GEB2.4PS, containing the domain B-encoding nucleotide sequence was digested with PvuII and the short fragment ligated into pMttSma, which is derived from pmttbns by digesting with BglII and inserting an adapter oligonucleotide containing an Sma site. The duplex linker adaptor inserted has the sequence pGATC-CCGG. pMttsma then contains a unique SmaI site at the 3' end of sequences encoding the tPA leader. The parent vector pMttbns SmithKline contains the Drosophila metalothionein gene (mtn), the human tissue plasminogen activator secretion signal ($tPA_L$) and the SV40 early polyadenylation signal. The resulting expression vector, pMttDomB is thus obtained as shown in FIG. 11. The sequence of the fusion is shown in FIG. 9.

The resulting pMttDomB vector was transfected into Schneider S2 cells which were maintained in Schneider medium (Life Technologies, Grand Island, N.Y.) supplemented with 10% heat-inactivated FBS at 25° C. The cells were plated the day prior to transfection at $5\times10^5$ cells in 60 mm tissue culture dishes in a total volume of 4 ml Schneider medium plus 10% FBS. The Schneider cells were then cotransfected with pMttDomB and pCOHygro (a hygromycin B phosphotransferase-based selection vector obtained from SmithKline Beecham) using standard calcium phosphate transfection. 48 hours after transfection, the medium was supplemented with hygromycin at 300 $\mu$g/ml; hygromycin-resistant cells grew in 2–3 weeks. Varying levels of the cotransformed plasmids were used in the transfection procedure ranging from expression plasmid: PCOHygro, 1:1 to 100:1.

EXAMPLE 11

Expression of 80% E in *Saccharomyces cerevisiae*

An expression vector (pLS6-80% E) was constructed for secretion of the N-terminal 80% (codons 1–395) of the DEN-2 PR-159 S1 envelope glycoprotein (80% E) from *S. cerevisiae*. The 80% E DNA sequences were obtained from plasmid p29D280E, described in example 1, by restriction endonuclease digestion with both BglII and SalI. The released fragment was isolated by agarose gel electrophoresis and subcloned between the BglII and SalI sites of pLS6, a yeast expression vector described in example 2. The resulting recombinant plasmid, pLS6-80% E, contains truncated E as a translationally in-frame fusion to the leader region of mating-factor α (MFα), a secreted yeast protein. The MFα leader ($MF\alpha_L$) contains a 19 amino acid secretion signal peptide followed by a 66 amino acid propeptide. Cleavage of the signal peptide is expected to occur concomitantly with translocation across the endoplasmic reticulum membrane. Maturation of MFα normally involves removal of the propeptide by Kex2p, a golgi protease, and subsequent trimming of N-terminal (Glu/Asp)Ala dipeptides by dipeptidyl aminopeptidase (DPAP). The herein described $MF\alpha_L$-80% E fusion was made such that processing of the $MF\alpha_L$ propeptide and trimming of a GluAla dipeptide results in 80% E with eight additional N-terminal amino acids derived from sequences present in the multiple cloning site of the pLS6 vector or in the PCR primer-adaptor used to synthesize the 80% E cDNA (see below).

```
                                                                   TR,1 (SEQ ID NO;19 and SEQ
                                                                   ID NO:20)
ATG.....GCT......GAG GCC TTT AGA TCT CGA GTA CCC GGG ACC ATG...GGA TAA TAG Met-18aa Ala-65aa Glu Ala Phe Arg Ser Arg Val Pro Gly Thr Met1...Gly395 End End

80%E

▲       ▲          ▲
    Signalase  Kex2p     DPAP
```

Cells cotransfected at ratios of 1:1, 5:1 and 20:1 were induced with 200 $\mu$M copper sulfate and the media and cells were harvested at days 1, 4 and 7. Western blots showed secretion of domain B into the medium.

EXAMPLE 10

Production of 60% E and 80% E in Drosophila

Using the adapted expression vector of Example 9, containing the Drosophila metalothionein gene, the human tissue plasminogen activator signal and the SV-40 early polyadenylation signal, the nucleotide sequences encoding 80% E, prM 80% E, 60% E and prM 60% E are inserted and the resulting vectors used to transform Schneider cells as described in Example 9. The mature truncated forms of the envelope protein are secreted into the medium, or properly processed, and are conformationally correct with respect to the corresponding native portions of the envelope protein.

Furthermore, crude media from these transformants employed in the protocol set forth in paragraphs A and B of Example 8 produce antibodies which are neutralizing against dengue virus.

Transcription of the gene fusion is driven by the *S. cerevisiae* copper-inducible copper metallothionein (CUPl) promoter.

After confirming the DNA sequence of the ligated junctions of expression vector pLS6-80% E, the recombinant DNA was transformed into S. cerevisiae strain GL43 (MATa trplΔl ura3–52 pep4::URA3; SmithKline Beecham) according to standard protocols (Gutherie & Fink, eds. 1991; Rose et al, 1990). Transformants were selected by their ability to grow on minimal medium (SD medium: Guthrie and Fink, 1991) without tryptophan supplementation.

In order to test for expression and secretion of 80% E, several transformants were grown as small-scale cultures (5 ml medium in 17×150 mm tubes). Single colonies were used to inoculate SD medium and the inoculated cultures were grown to saturation (overnight, 30° C., 220 rpm). $1\times10^8$ cells from the overnight culture were used to inoculate 5 ml of minimal SD medium supplemented with Casamino acids (2 g/l; Difco) and $CuSO_4$ (200 $\mu$M). This expression culture was fed with glucose (4 g/l, final concentration) and sodium phosphate (pH 6.7, 20 mM, final concentration) at 24 hours post inoculation and was harvested by centrifugation at 48 hours of growth (30° C., 220 rpm, in 17×150 mm tubes). Cell-free spent medium was buffer-exchanged with TEEN+

PIC (50 mM Tris, 10 mM EDTA, 10 mM EGTA, 150 mM NaCl, pH 8.0 with 1 μg/ml each of pepstatin and leupeptin and 1 mM phenylmethylsulfonylfluoride) and concentrated 250-fold using Centricon-30 (Amicon) ultrafiltration. An extract of cellular protein was prepared by lysing the yeast cells with vigorous agitation in the presence of glass beads (425–600 μm) and TEEN+PIC using a Mini Beadbeater apparatus (BioSpec Products, Bartlesville, Okla.). Samples were endoglycosidase H$_f$ digested according to the manufacturer's (New England Biolabs, Beverly, Mass.) protocol prior to SDS-PAGE analysis. Protein gels were Coomassie-stained directly as well as Western blotted and immunoprobed using mouse polyclonal serum raised against recombinant domain B (described in example 15). Negative control yeast carrying the expression vector without a Dengue gene insert secreted no proteins recognized by the anti-domain B serum, while the major immunoreactive band from pLS6-80% E medium had a relative mobility matching that of other recombinant 80% E proteins (see Example 17). The pLS6-80% E medium also contained a minor immunoreactive species with an apparent molecular weight 6–8 kD higher than 80% E; this is likely to be unprocessed MFα propeptide-80% E. The pLS6-80% E cellular protein extract contained many immunoreactive polypeptides not observed in negative control cells, two of which match the secreted products discussed above. A Coomassie-stained protein corresponding to recombinant 80% E could not be identified in either the pLS6-80% E secreted sample or the total cellular protein sample. This indicates the relatively low levels of recombinant protein expression in these preparations.

EXAMPLE 12

Construction of Expression Vector DPIC9-80% E and Secretion of 80% E by *P. pastoris* Expressing $MF\alpha_L$-80% E The expression vector constructed to secrete 80% E from *P. pastoris* was engineered to express amino acids 1–395 of the DEN-2 PR-159 S1 envelope glycoprotein as a fusion to the $MF\alpha_L$. The DNA sequences encoding 80% E were obtained from the clone p29D280E, described in example 1, by digestion with the restriction enzymes SmaI and SalI. The isolated fragment was treated with the Klenow DNA polymerase I fragment enzyme to make the SalI end blunt. This 80% E fragment was then cloned into the Pichia expression vector pPIC9 (Invitrogen, San Diego, Calif.) which contains the MFα secretion leader ($MF\alpha_L$) sequence, SnaBI, EcoRI, and NotI cloning sites, and uses the HIS4 gene as a selectable marker. The described 80% E fragment was ligated with pPIC9 plasmid DNA that was previously digested with the restriction enzyme SnaBI. The orientation and genetic integrity of the resulting gene fusion expression vector, pPIC9-80% E, was confirmed by restriction digestion and DNA sequence analysis. The organization, partial nucleotide and predicted amino acid sequences of the $MF\alpha_L$-80% E fusion gene are shown below:

The location of the signalase and Kex2 cleavage sites which remove the pre and pro portions of the MFα leader peptide, respectively, are indicated. The dengue sequences are indicated in bold type. The $Met_1$ residue is the N-terminal amino acid of the E glycoprotein and $Gly_{395}$ is residue 395 from the amino terminal end of the envelope glycoprotein. The expression of a recombinant product in Pichia from the pPIC9 vector is driven by the methanol inducible promoter derived from the Pichia AOX1 (alcohol oxidase 1) gene.

The pPIC9-80% E expression vector was transformed into spheroplasts of *P. pastoris* strain GS115 (his4) and transformants were selected for their ability to grow on minimal medium without histidine supplementation. Strain GS115 and the protocol used for transformation were obtained from Invitrogen (San Diego, Calif.). Transformants were tested for their ability to express and secrete 80% E by growing selected clones in small cultures (5 to 50 ml). The transformants were first grown to saturation (24 to 36 hrs.) in BMGY medium (1% yeast extract, 2% peptone, 100 mM potassium phosphate, pH 6.0, 1.34% yeast nitrogen base without amino acids, $4\times10^{-5}$% biotin, 1% glycerol). The cells were collected by centrifugation and suspended in one half the original culture volume with BMMY (identical to BMGY except the glycerol component of BMGY is replaced in BMMY with 0.5% methanol) medium and cultured for 48 hrs. Proteins secreted into the culture medium as well as cellular proteins were treated with endoglycosidase $H_f$, (EndoH$_f$, New England Biolabs, Beverly, Mass.) and separated by SDS-PAGE. Protein gels were analyzed by both Coomassie staining and immunoprobing of Western blots. When non-EndoH treated samples are compared to EndoH treated samples on Coomassie stained gels of proteins prepared from the culture medium, a unique staining band of approximately 50 kD is present in the EndoH treated lanes of all the pPIC9-80% E transformants. Immunoprobing with anti-domain B serum (see example 6) detected a smear ranging from 50 to 90 kD in the non-EndoH treated samples and a unique band of approximately 50 kD in the EndoH treated samples on Western blots of proteins prepared from the culture medium. No bands were detected by the anti-domain B serum in negative control lanes. Variable amounts of the corresponding immunoreactive band were detected in EndoH treated samples of cellular protein samples. The approximately 50 kD 80% E product produced by the $MF\alpha_L$-80% E construct is consistent with the approximate molecular weight as determined by SDS-PAGE of other recombinant 80% E proteins (see Example 17). The amount of secreted 80% E in the culture medium is about 1% of the total secreted protein as estimated by the intensity of the Coomassie staining band detected. In one liter cultures, the amount of 80% E secreted into the culture medium was determined to be 500 ng/ml by use of a sandwich ELISA method.

EXAMPLE 13

Construction of Expression Vector pMttbns-80% E and Secretion of 80% E by *Drosophila melanogaster* Schneider Cells Expressing $tPA_L$-80% E The expression vector constructed to secrete 80% E from *Drosophila melanogaster* tissue culture cells included the

```
ATG ......... GAG GCC TTTAGATCTCGAGTACCCGGGACC ATG...GGA TAA    (SEQ ID NO:21 and SEQ ID NO:22)
Met-18aa-65aa Glu Ala PheArgSerArgValProGlyThr Met1...Gly395 END

80%E

▲      ▲        ▲

Signalase Kex2p    DPAP
``` sequences encoding the DEN-2 PR159/S1 envelope glycoprotein amino acids 1–395. The DNA sequences for 80% E were obtained from the clone p29D280E (described in Example 1) by digestion with the restriction enzymes BglII and SalI. The released 80% E fragment was cloned into the BglII plus XhoI-digested *D. melanogaster* expression vector pMttΔXho. The expression vector pMttΔXho is a derivative of the vector pMttbns (SmithKline Beecham) that contains a *D. melanogaster* metallothionein gene promoter (Mtn), the human tissue plasminogen activator leader sequence ($tPA_L$), and the SV40 early polyadenylation signal. A 15 bp BamI DNA fragment containing a XhoI site was deleted from pMttbns to make pMttΔXho, in which the BglII and another XhoI restriction endonuclease sites are unique. This construction resulted in the 80% E fragment being fused to the $tPA_L$ sequence. During normal maturation of tissue plasminogen activator the 20 amino acid prepeptide region of the leader sequence is removed by signalase in the endoplasmic reticulum and the 11 amino acid propeptide region is enzymatically removed in the Golgi. The genetic integrity of the gene fusion expression vector, pMtt80% E, was confirmed by restriction digestion and DNA sequence analysis. The nucleotide and predicted amino acid sequences of the $tPA_L$-80 E fusion gene are shown below:

medium (JRH Biosciences) and induced with 200 μM $CUSO_4$. The medium and cells from induced cells were separately harvested after 6–7 days of induction. Proteins secreted into the culture medium were separated by SDS-PAGE, and proteins were analyzed by both Coomassie staining and immunoprobing of Western blots. The Coomassie blue-stained SDS-PAGE gels shows that the approximately 50 kD secreted 80% E product is one of the predominant proteins in the unconcentrated medium, comprising as much as 20% of the total protein. Immunoblots probed with anti-DEN2 hyperimmune mouse ascites fluid (HMAF; from Robert Putnak, Walter Reed Army Institute of Research) and polyclonal anti-domain B antisera (Example 6) revealed a single immunoreactive polypeptide of approximately 50 kD present in unconcentrated medium. In addition, immunoblots revealed that the 80% E produced by the $tPA_L$-80% E construct was slightly larger than that obtained upon expression of a $tPA_L$-prM80% E construct (described in detail in Example 17). This additional mass may owe to the nine adaptor amino acids at the amino terminus of 80% E (GARSRVPGT-(SEQ ID NO:25)80% E) when expressed from pMtt80% E versus 80% E expressed from pMttprM80% E (Example 17). The tPA propeptide, if not proteolytically removed, may also contribute to the additional molecular weight of 80% E expressed from pMtt80% E.

```
                                          (SEQ ID NO:23 and SEQ ID NO:24)
ATG ............... GGA GCC AGA TCT CGA GTA CCC GGG ACC ATG ... GGA      TAA
(SEQ ID NO:23 and SEQ ID NO:24)

Met- 20 aa - 11 aa -Gly Ala Arg Ser Arg Val Pro Gly Thr Met1 ... Gly395  END pre▲ pro-tPA▲                                         80%E
```

The tPA pre- and propeptide regions are delineated by pre▼ and pro-tPA▼, respectively, and the dengue sequences are indicated in bold type. The $Met_1$ residue is the N-terminal amino acid of the envelope glycoprotein and $Gly_{395}$ is residue 395 from the amino terminal end of the envelope glycoprotein.

The selection plasmid, pCOHygro (SmithKline Beecham), carries the *E. coli* hygromycin B phosphotransferase gene under the transcriptional control of a *D. melanogaster copia* transposable element long terminal repeat and confers resistance to hygromycin B. Others have demonstrated that Schneider cells that have been co-transfected with both the pMtt expression vector and the pCOHygro plasmid and are then selected for hygromycin B resistance produce stable cell populations that contain multiple copies of the co-transfected gene of interest. *Drosophila melanogaster* Schneider cells (ATCC, Rockville, Md.) were cotransfected with the pMtt80% E and pCOHygro plasmids at a ratio of 20:1 using the calcium phosphate coprecipitation method (Gibco BRL). Transformants were selected by outgrowth in Schneider medium (Gibco BRL) supplemented with 10% fetal bovine serum (Hyclone) and 300 μg/ml hygromycin (Boerhinger Mannheim). Transformants were split to a cell density of $2\times10^6$ cells/ml in serum free Excell

EXAMPLE 14

Subcloning of Dengue prM100% E and prM80% E cDNAs and Mutagenesis of E Secretion Signal-encoding Sequence (mutSS)

A cDNA clone of DEN-2 PR159/S1 designed to encode the preMembrane, Membrane, and Envelope genes (prM100% E) was constructed by PCR amplification essentially as described in Example 1 for the subcloning of 80% E. This cDNA clone includes nucleotides 439 to 2421 of the DEN-2 genome. The dengue cDNA fragment was generated using synthetic oligonucleotide primers D2pM439p and D2E2421m (see example 1 for nomenclature) and plasmid pC8 (Hahn et al, 1988, supra) as template. In addition to DEN-2 specific sequences, the primers contained the identical adaptor sequences described in Example 1, except that a methionine codon (ATG) was included immediately preceding the first codon of the preMembrane sequence (phenylalanine). The primers are:

```
D2prM439p
          BglII

5'-attctagatctcgagtacccgggacc atg TTT CAT CTG ACC ACA CGC-3'  (SEQ ID NO:26)

XbaI    XhoI     SmaI

D2E2421m
```

```
                           -continued
     SalI
5'-tctctagagtcga cta tta GGC CTG CAC CAT AAC TCC         (SEQ ID NO:27)

XbaI       END END
```

The PCR-generated prM100% E cDNA fragment was digested with the restriction endonuclease XbaI and ligated into the XbaI site of pBluescript SK⁺ (Stratagene, San Diego, Calif.) to obtain the plasmid p29prME13. DNA sequence analysis of the PCR-generated cDNA clone identified three PCR-introduced nucleotide differences between pC8 and p29prME13. A T→C transition at nucleotide 1255 resulted in a silent mutation, while the A→G transition at nucleotide 1117 resulted in the conservative amino acid substitution of a valine for an isoleucine. The final transition observed at nucleotide 1750 replaced a methionine, adjacent to a cysteine involved in a disulfide bond in domain A, with a valine. The effect of this substitution on the ability of the disulfide to form or its stability is not known.

To generate a cDNA subclone representing prM80% E, a 794 bp BamHI-SalI fragment from p29prME13 representing the envelope carboxy terminal-encoding fragment was removed. This fragment was replaced with a 431 basepair BamHI-SalI fragment from p29D280E (described in Example 1) that encodes a 20% carboxy end truncation of the envelope glycoprotein. The BamHI site is a naturally occurring site within the envelope cDNA, and the SalI site is an engineered site that immediately follows the stop codons encoded by the PCR primers. The resulting truncated cDNA clone, p48BSprM80E, was confirmed by restriction digestion and DNA sequence analysis to encode amino acids 1 through 395 of the envelope glycoprotein following prM.

Expression of the prM80% E cDNA in *S. cerevisiae* (Example 15) demonstrated absence of proteolytic processing between the prM and 80% E proteins in this yeast. To improve processing of E from prM, oligonucleotide-directed mutagenesis was performed to alter the naturally occurring signalase cleavage site between the prM and E proteins. Based on the algorithm of Von Heijne (1986, Nucl. Acids Res. 14:4683–4690), the natural DEN-2 E secretion signal peptide receives a poor predictive score for its function as a secretion signal. The algorithm of von Heijne is based on N-terminal amino acid sequences found in secreted and nonsecreted proteins. Scores for functional secretion signal peptides range from 3.5 to 17, with a mean of ~10. The score for the secretion signal peptide of E of DEN-2 PR159/S1 is 5.2, near the lower end of the range for signal peptides. In the mutagenesis, the sequence encoding the four amino acids immediately preceding and the amino acid immediately following the signalase cleavage site were altered to change these five amino acids. The modified signal sequence has a score of 12.4 based on von Heijne's algorithm. The original and altered nucleotide sequences of the mutagenized region and the encoded amino acid sequences relative to the signalase site are:

```
Original    ATC GCT CCT TCA ATG ACA ATG CGC TGC  (SEQ ID NO:30 and SEQ ID NO:31)
            Ile Ala Pro Ser Met Thr Met Arg Cys
Mutagenized ATC GCT GGC GCT CAA GCT CAA CGC TGC  (SEQ ID NO:32 and SEQ ID NO:33)
            Ile Ala Gly Ala Gln Ala Gln Arg Cys
                         Membrane | Envelope Signalase Cleavage
```

The mutagenized sequence and the resulting amino acid changes are indicated in bold.

To perform the mutagenesis, a 1,122 bp SmaI-HindIII fragment spanning the prM-E signalase cleavage site from the p29prME13 cDNA clone was subcloned into pAlterl (Promega, Madison, Wis.) to yield the plasmid pAltSmaH3prME. The 1,122 bp SmaI-HindIII fragment contains all of prM and 611 bp of the E sequence. The HindIII site is a naturally occurring site within the E sequence that is located at nucleotide 1547 of the genomic sequence. The mutagenized clone, pAltSmaH3prME (mutSS), was verified by DNA sequence analysis.

EXAMPLE 15

Construction of Expression Vectors pLS6-prM80% E and pLS6-prM(mutSS)80% E, Expression of MF$\alpha_L$-prM80% E and MF$\alpha_L$-prM(mutSS)80% E in *Saccharomyces cerevisiae*, and Secretion of 80% E by *Saccharomyces cerevisiae* Expressing MF$\alpha_L$-prM(mutSS) 80% E For expression of DEN-2 PR159/S1 preMembrane protein amino acids 1–166 and Envelope glycoprotein amino acids 1–395 as a single continuous open reading frame in *S. cerevisiae*, DNA sequences encoding these proteins were obtained by digestion of plasmid p48BSprM80E (see Example 14) with restriction endonucleases BglII and SalI. This fragment was cloned into the pLS6 yeast expression vector (see Example 2) that had been digested with BglII and SalI. The structure of the resulting gene fusion expression vector, pLS6-prM80% E, was confirmed by restriction digestion and DNA sequence analysis. The nucleotide and predicted amino acid sequences of the MF$\alpha_L$-prM80% E fusion gene are shown below:

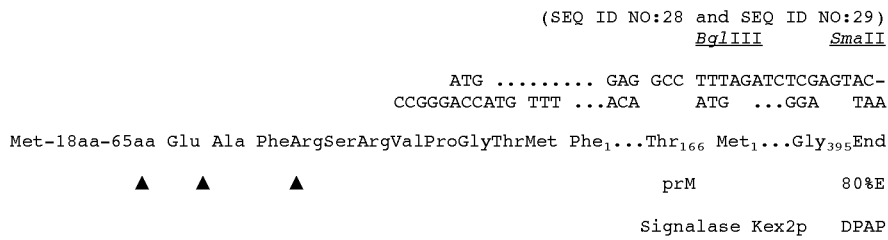

```
                                      (SEQ ID NO:28 and SEQ ID NO:29)
                                                    BglIII     SmaII ATG ......... GAG GCC TTTAGATCTCGAGTAC-
                         CCGGGACCATG TTT ...ACA     ATG  ...GGA   TAA Met-18aa-65aa Glu Ala PheArgSerArgValProGlyThrMet Phe1...Thr166 Met1...Gly395End ▲    ▲        ▲                              prM             80%E Signalase Kex2p   DPAP
```

The location of the signalase, Kex2p, and DPAP cleavage sites involved in the processing of the MFα leader peptide are indicated (See Example 1 of this application for a detailed explanation). The dengue sequences are indicated in bold. The $Phe_1$ and $Thr_{166}$ residues are the N-terminal and C-terminal amino acid residues of prM, respectively. The $Met_1$ residue is the N-terminal amino acid of the envelope glycoprotein and $Gly_{395}$ is residue 395 from the amino terminal end of the envelope glycoprotein.

The pLS6prM80% E plasmid was transformed into *Saccharomyces cerevisiae* strain GL43 (MATa ura3-52 trplΔl pep4:URA3) and screened for 80% E expression as described in Example 1. Proteins secreted into the culture medium as well as total cellular proteins were treated with Endoglycosidase $H_f$ (Endo$H_f$, New England Biolabs, Beverly, Mass.) prior to analysis by SDS-PAGE followed by Coomassie Blue staining or Western blot immunoprobing. A novel secreted protein could not be identified either on Coomassie Blue stained SDS-PAGE gels or Western blots probed with anti-DEN2 hyperimmune mouse ascitic fluid (HMAF; from R. Putnak, Walter Reed Army Institute for Research) or anti-DomB antiserum (see Example 6). Western blot analysis of total cellular protein revealed a HMAF immunoreactive band of approximately 90 kD suggesting that the recombinant product had not been processed to prM and E. Probing of companion Western blots with polyclonal antisera that recognized the MFα leader peptide (from J. Rothblatt, Dartmouth University) confirmed that the product recognized by the anti-DEN2 HMAF was identical to that recognized by anti-MFα serum, demonstrating that the $MFα_L$-prM80% E fusion protein was not processed into its individual components ($MFα_L$, prM, and 80% E).

The unsuccessful processing of E from prM in the $MFα_L$-prM80% E fusion protein may be an obstacle to the proper folding and secretion of E. To assess whether the optimized dengue signal sequence (see Example 16) facilitated the processing of the envelope protein at the prM-E junction, the altered E signal sequence from pLS6prM(mutSS)100E-TGA was introduced into pLS6prM80% E to create plasmid pLS6prM(mutSS)prM80% E. This procedure replaced the native E signal sequence (Pro-Ser-Met-$Thr_1$-$Met_{+1}$(SEQ ID NO:34)) with the optimized E signal sequence (Gly-Ala-Gln-$Ala_{-1}$-$Gln_{+1}$(SEQ ID NO:34)).

Plasmid pLS6prM(mutSS)100E-TGA was obtained by homologous replacement of a SmaI-SacI fragment between plasmids pAlterSmaH3prME(mutSS) (see Example 14) and pLS6prM100E. DNA sequencing of pLS6prM(mutSS) 100E-TGA identified an unintended TGA stop codon within E downstream of the mutated secretion signal. To transfer the altered secretion signal encoding sequence to pLS6prM80% E and to separate the cDNA fragment containing the altered secretion signal of E from the TGA stop codon, a BglII-EcoNI fragment from pLS6prM(mutSS) 100E-TGA, encompassing prM and the first 430 nucleotides of E and lacking the TGA stop codon, was transferred to plasmid pLS6prM80% E which had been similarly digested to yield the expression plasmid pLS6prM(mutSS)80% E. The sequence of the expression plasmid was confirmed by restriction digestion and DNA sequence analysis. The nucleotide and predicted amino acid sequences of the $MFα_L$-prM junction are identical to the sequences listed above.

As described for the non-mutagenized plasmid, the DNA was transformed into the *S. cerevisiae* GL43 strain and transformants were selected based upon their ability to grow on unsupplemented minimal medium (see Example 11). Transformants were cultured, induced, and evaluated as described above for the non-mutated $MFα_L$-prM80% E transformants. Proteins secreted into the culture medium as well as total cellular proteins were treated with Endo$H_f$ prior to separation by SDS-PAGE. Protein gels were analyzed by Coomassie staining and immunoprobing of Western blots. SDS-PAGE analysis of concentrated culture medium failed to identify a novel Coomassie staining band. Immunoprobing with anti-DEN2 HMAF and anti-DomB antiserum, however, revealed a small amount of processed immunoreactive E protein in the medium. The size of the immunoreactive protein (approximately 50 kD) was similar to the secreted protein from pLS6-80% E expression vector. Evaluation of intracellular expression of the fusion protein containing the optimized secretion signal by SDS-PAGE and Western blot demonstrated that the transformed cells produce immunoreactive product recognized by anti-DEN2 HMAF and anti-DomB antiserum. Unlike the immunoreactive product seen in pLS6prM80% E transformants, the immunoreactive band found in pLS6(mutSS)prM80% E transformants was not recognized by $MFα_L$ anti-serum suggesting that processing had occurred at the prM-E junction. Thus, the mutagenesis of the signalase cleavage site resulted in greatly enhanced processing of the $MFα_L$-prM80% E product at the prM-E junction.

EXAMPLE 16

Construction of Expression Vector pPIC9-prM (mutss)80% E and Secretion of 80% E by *P. pastoris* Expressing $MFα_L$-prM(mutss) 80% E The expression vector constructed to express preMembrane-mutated secretion signal- 80% Envelope (pPICprM(mutSS)80% E) in *P. pastoris* from a single continuous open reading frame utilized the DEN-2 PR159/S1 prM and E gene sequences described above (Example 14). The plasmid, pPIC9-prM(mutSS)80% E, was constructed by transferring a prM(mutSS)80% E fragment from the *S. cerevisiae* expression plasmid pLS6prM(mutSS)80% E into pPIC9. The *P. pastoris* expression vector pPIC9 (Example 4) and the *S. cerevisiae* expression vector pLS6 (Example 2) both use the MFα prepropeptide leader ($MFα_L$) sequence to direct the secretion of expressed proteins, and the two $MFα_L$ sequences share an XhoI restriction endonuclease site, encoding amino acids leucine and glutamic acid, just upstream of the Kex2 protease site. The transfer of the dengue cDNA fragment made use of this XhoI site.

Prior to transferring the prM(mutSS)80% E cDNA fragment, sequences encoding extraneous amino acids and an extraneous XhoI site at the MFα$_L$-prM fusion were first removed. This was accomplished by digesting pLS6-prM (mutSS)80% E with restriction endonuclease XhoI and XmaI into which was ligated a synthetic oligonucleotide duplex (5'-TCGAGAAGAGAGAAG-3' (SEQ ID NO:36) and 5'-CCGGCTTCTCTCTTC-3' (SEQ ID NO:37)). This manipulation deleted the extraneous XhoI site, the XmaI site, and six extraneous codons and preserved the MF$\alpha_L$ proteolytic processing sites and the XhoI site within MF$\alpha_L$ required for the cDNA fragment transfer from pLS6 to pPIC9. The nucleotide and predicted amino acid sequence at the MF$\alpha_L$-prM fusion junction from pLS6-prM(mutSS)80% E and pLS6Δ-prM(mutSS)80% E are:

polypeptides were detected by the anti-domain B serum in negative control samples. Various amounts of the corresponding immunoreactive protein were detected in EndoH treated samples of cellular proteins. We estimate that the amount of secreted 80% E in the culture medium is less than 1% of the total amount of secreted protein based on the observation that no polypeptide of the appropriate molecular weight was detected by Coomassie staining of EndoH$_f$ treated samples.

EXAMPLE 17

Construction of pMttbns-prM80% E and Secretion of 80% E by *Drosophila melanogaster* Schneider cells Expressing tPA$_L$-prM80% E For expression of DEN-2 PR159/S1 preMembrane protein amino acids 1–166 and Envelope glycoprotein amino <u>MFα$_L$-prM junction of pLS6-prM(mutSS)80%E</u>

```
        XhoI                             XhoI    XmaI
ATG ...CTC GAG AAA AGG GAG GCC TTTAGATCTCGAGTACCCGGGACCATG TTT..      (SEQ ID NO:38 and SEQ ID NO:39)
Met ...Leu Glu Lys Arg Glu Ala PheArgSerArgValProGlyThrMet Phe1..
                        ▲       ▲
                      Kex2p   DPAP
```

<u>MFα$_L$-prM junction of pLS6Δ-prM(mutSS)80%E</u>

```
        XhoI
ATG ...CTC GAG AAA AGG GAG GCC GGGACCATG TTT..                        (SEQ ID NO:40 and SEQ ID NO:41)
Met ...Leu Glu Lys Arg Glu Ala GlyThrMet Phe1..
                        ▲       ▲
                      Kex2p   DPAP
```

To construct the clone pPIC9-prM(mutSS)80% E, a XhoI-SalI fragment encoding prM(mutSS)80% E sequences was obtained from pLS6Δ-prM(mutSS)80% E and was inserted into the pPIC9 vector that had been digested with XhoI. The genetic integrity of the expression plasmid, pPIC9-prM (mutSS)80% E, was confirmed by restriction digestion.

The pPIC9-prM(mutSS)80% E expression vector was transformed into spheroplasts of *P. pastoris* strain GS115 (his4), and His$^+$ transformants were selected for their ability to grow on minimal medium without histidine supplementation. The transformants were screened for expression and secretion of 80% E as described in Example 12. No unique Coomassie staining bands were detected in the culture acids 1–395 as a single continuous open reading frame in *Drosophila melanogaster* Schneider 2 tissue culture cells, DNA sequences encoding these proteins were obtained by digestion of the p48BSprM80% E clone (described in Example 14) with the restriction enzymes BglII and SalI. This fragment was cloned into the unique BglII and XhoI restriction sites of plasmid pMttΔXho (described in Example 13). The cloning junctions of the resulting gene fusion expression vector, pMttprM80E, were confirmed by restriction endonuclease digestion and DNA sequence analysis. The partial nucleotide and predicted amino acid sequences of the tPA$_L$-prM80E fusion gene are:

```
                                                           (SEQ ID NO:42 and SEQ ID NO:43)
ATG ............ GGAGCCAGATCTCGAGTACCCGGGACCATG TTT ..ACA     ATG  ..GGA    TAA
Met-20 aa- -11 aa-GlyAlaArgSerArgValProGlyThrMet Phe1..Thr166 Met1..Gly395 END
       pre▲pro-tPA▲                                  prM              80%E
``` medium of either non-EndoH$_f$ or EndoH$_f$ treated samples (similar to that observed for culture medium from pPIC9-80% E transformants—see Example 12). Western immunoblots of proteins from the culture medium probed with anti-domain B serum detected multiple bands with a diffuse area of reactivity ranging from 50 to 90 kD in the non-EndoH treated samples and a unique band of approximately 50 kD in the EndoH treated samples. No immunoreactive The tPA pre- and propeptide regions are delineated by pre▼ and pro-tPA▼, respectively, and the dengue sequences are indicated in bold type. The Phe$_1$ and Thr$_{166}$ residues are the N-terminal and C-terminal amino acid residues of prM, respectively. The Met$_1$ residue is the N-terminal amino acid of envelope glycoprotein and Gly$_{395}$ is residue 395 from the amino terminal end of the envelope glycoprotein.

As described previously in Example 13, Schneider 2 cells were cotransfected with pMttprM80% E DNA at ratios of 1:1, 5:1, and 20:1 relative to pCOHygro DNA. Transformants were induced with 200 μM CuSO$_4$ and expression of prM80% E was examined at various times after induction. Proteins secreted into the culture medium as well as cellular proteins were separated by SDS-PAGE. Protein gels were analyzed by both Coomassie Blue staining and immunoprobing of corresponding Western blots. Analysis of Coomassie Blue-stained SDS-PAGE gels identified a novel band of approximately 50 kilodalton in all transfectants. This novel band was also recognized by anti-DEN-2 HMAF in Western blot analysis. This ~50 kD immunoreactive band is roughly the same size as the secreted EndoH-treated product from pLS6-80% E transformed yeast cells (Example 11) and slightly smaller than the secreted 80% E from pMttbns80% E-transformed D. melanogaster Schneider cells (Example 13), suggesting the Envelope protein had been processed away from the preMembrane protein. (The size discrepancy between 80% E secreted by pMtt80% E and pMttprM80% E Schneider cells is discussed in Example 13.) Polyclonal antisera to the pr portion of prM (from Peter Wright, Monash University, Australia) did not recognize the ~50 kD protein, confirming that the 80% E produced in the transfected cells was processed from prM. In fact, no evidence of a higher molecular weight band that might correspond to unprocessed prM80% E was detected in any sample, suggesting that the proteolytic processing of prM from E is extremely efficient in Schneider cells. The fate of the prM portion of the fusion remains unresolved as no distinct immunoreactive band was detected by probing with the anti-pr antisera.

The secreted 80% E glycoprotein was partially purified (judged by the presence of a single major band on a sliver stained SDS-PAGE gel) and its N-terminal amino acid sequence was determined. To purify the secreted glycoprotein, culture medium was concentrated and buffer exchanged against 20 mM succinate pH 5.7. The buffer exchanged material was loaded onto a CM-BioGel column and eluted in 150 mM NaCl. The 150 mM NaCl eluant was separated on an SDS-PAGE gel and electro-transferred to Immobilon-P membrane (Millipore). The 80% E band was excised, and the N-terminal amino acids were determined by Edman sequencing. Two amino acid sequences were obtained. One, Met-Xxx-Xxx-Ile-Gly-Ile (SEQ ID NO:44), had an individual residue yield of 7.9–10.0 picomoles, while the other, Val-Xxx-Val-Gly-Ala-Val, (SEQ ID NO:45) had a 3.2–4.2 picomole yield. Incomplete reduction of the Cys at position three may account for lack of its detection. the first sequence is consistent with the expected sequence, Met-Arg-Cys-Ile-Gly-Ile (SEQ ID NO:46), supporting the interpretation that the ~50 kD secreted immunoreactive glycoprotein is correctly processed 80% E of DEN-2.

Sensitivity of the secreted 80% E to endoglycosidases was evaluated by molecular weight shift of the protein in SDS-PAGE and Western immunoblots following endoglycosidase treatment. Resistance of the secreted 80% E to Endoglycosidase H$_f$ (Endo H$_f$; New England Biolabs) and sensitivity to N-glycosidase F (PNGase F; New England Biolabs) digestion indicated that the secreted product contains N-linked glycosylation, and that the glycosylation is probably complex and is neither high mannose nor hybrid in composition.

The secreted protein is one of the predominant proteins in the unconcentrated medium, comprising as much as 20% of the total secreted protein. Estimates of the concentration of the 80% E product in unconcentrated medium based upon sandwich ELISA assays (described in detail in Example 7) and Coomassie blue staining range from 3–16 μg/ml depending on the preparation. Immunoblots probed with polyclonal anti-dengue 2 hyperimmune mouse ascites fluid (DEN-2 HMAF; from R. Putnak, WRAIR) demonstrated that the amount of secreted 80% E produced by the transfectants increased over time from day 1 post induction to 7 days post induction. The amount of 80% E detected intracellularly in the transfectants correlated with the cotransfection ratio, but the increase in intracellular 80% E with time was not as dramatic as for secreted 80% E, suggesting efficient secretion of 80% E and accumulation in the medium.

EXAMPLE 18

Induction of Anti-Dengue 2 Antibodies in Mice by *Pichia pastoris*-secreted 80% E

*P. pastoris* cells transformed with pPIC-80% E (described in Example 12) were induced with 0.5% methanol and the medium was collected after 40 hours of induction (for additional details on culture conditions see Example 12). The medium was filtered through a 0.5 μm low protein binding filter (Opticap, Millipore), then buffer exchanged with phosphate buffered saline (10 mM sodium phosphate, 2 mM potassium phosphate, 0.15 M sodium chloride, and 27 mM potassium chloride, pH 7.5) and concentrated approximately 40 fold using a combination of tangential flow (Minitan; Millipore) and centrifugal ultrafiltration (Centriprep 30; Amicon). The concentrated medium was analyzed by Western blot and assayed by sandwich ELISA (described in detail in Example 7) prior to injection into mice. Five week-old Swiss Webster outbred mice (Simonsen) were immunized by intraperitoneal (I.P.) injection with 100 μg total protein of the crude concentrated 80% E medium with or without complete Freund's adjuvant. Controls for this experiment included a negative control medium prepared from a non-recombinant *P. pastoris* culture as described above for the 80% E medium. Protein precipitation was observed during the concentration of the negative control medium, consequently the final protein concentration of the concentrated medium was lower than that from the 80% E medium. (For this reason, 12.5 μg of total protein in Freund's complete adjuvant was used for immunization with the negative control medium.) Additional controls included saline and KLH-domain B, a recombinant dengue product previously shown to induce neutralizing antibodies (Example 8), both were administered with Freund's complete adjuvant. The mice received three I.P. boosts consisting of one half the priming dose with or without Freund's incomplete adjuvant, and consistent with the specific priming immunization. The boosts were administered at two week intervals.

Following the second boost, the animals were test bled (tail vein) and the immune response was monitored using an indirect ELISA. In the ELISA assay, plates were coated with a bovine serum albumin (BSA)-domain B conjugate, blocked with BSA, and serial dilutions of the mouse sera were then incubated with the coating antigen. Alkaline phosphatase-labeled goat anti-mouse IgG was used as the secondary detecting antibody, and the color development upon addition of an alkaline phosphatase chromogenic substrate was monitored. The ELISA titer is that which corresponded to the highest dilution of serum resulting in an optical density two-fold above background (reactivity of the serum against BSA only). Following the third boost, the animals were bled-out and the serum was tested for anti-DEN2 responsiveness by indirect ELISA and the plaque reduction neutralization assay (PRNT). In the PRNT assay, the mouse sera were serially diluted in Eagles minimal essential medium (EMEM; BioWhittaker) supplemented with 10% fetal bovine serum (FBS; Hyclone) and mixed with 100 plaque forming units (pfu) of DEN2 virus (New Guinea C strain, from Robert Putnak, WRAIR). After allowing one hour for binding and neutralization of the virus, the serum-virus mixtures were plated onto susceptible monkey kidney monolayers (Vero cells, from Robert Putnak, WRAIR) plated in EMEM (BioWhittaker) supplemented with 10% FBS (Hyclone) in 6 well tissue culture dishes (Corning). The cells were overlaid with 0.9% agarose (Seakem; FMC) in EMEM supplemented with 5% FBS and viral cytopathic effect was allowed to develop for 6–7 days. The resulting viral plaques were stained with 0.012% neutral red (Sigma) in 1% agarose (Seakem; FMC). The number of plaques in each cluster were counted and compared to a no-serum viral control. The PRNT$_{80}$ was the highest dilution of serum that resulted in an 80% reduction in the number of plaques from a given viral inoculum. Results from the ELISA and PRNT assays are summarized in Table 4. The *P. pastoris* expressed 80% E induces a potent anti-DEN2 response in mice, with ELISA titers of up to 1:102,400. The titers obtained in the presence of adjuvant exceeded those obtained without adjuvant. The lack of a strong virus neutralizing response (PRNT$_{80}$ titers, Table 4) may simply reflect the crude nature of the immunogen, as similar results were obtained when crude domain B was used as an immunogen (see Example 8).

TABLE 4

Induction of Anti-DEN2 Immune Response in Mice Immunized with *P. pastoris*-expressed 80% E

| mouse | antigen | adjuvant | 3° titer ELISA | 4° titer ELISA | 4° titer PRNT$_{80}$ |
|---|---|---|---|---|---|
| 30-1 | Saline | Freund's | <1:50 | <1:100 | |
| 30-2 | | | <1:50 | <1:100 | |
| 30-3 | | | <1:50 | <1:100 | |
| 30-4 | | | <1:50 | <1:100 | |
| 30-5 | | | <1:50 | <1:100 | |
| 32-1 | KLH-DomB | Freund's | >1:6400 | 1:25600 | |
| 32-2 | "26" µg | | >1:1600 | 1:102,400 | |
| 32-3 | | | <1:100 | 1:100 | |
| 32-4 | | | >1:6400 | 1:102,400 | |
| 32-5 | | | <1:100 | <1:100 | |
| 34-1 | 12.5 µg | Freund's | <1:100 | <1:100 | |
| 34-2 | Pichia | Freund's | <1:100 | 1:100 | |
| 34-3 | negative | | <1:100 | <1:100 | |
| 34-4 | control | | <1:100 | <1:100 | |
| 34-5 | medium | | <1:100 | 1:100 | |
| 36-1 | 100 µg | Freund's | >1:6400 | 1:25,600 | <1:10 |
| 36-2 | Pichia | | 1:6400 | 1:25,600 | <1:10 |
| 36-3 | 80% E | | >1:6400 | 1:25,600 | <1:10 |
| 36-4 | total | | 1:100 | 1:100 | <1:10 |
| 36-5 | medium | | 1:6400 | 1:102,400 | <1:10 |
| 37-1 | 100 µg | None | <1:100 | 1:100 | |
| 37-2 | Pichia | | 1:1600 | 1:6400 | |
| 37-3 | 80% E | | 1:100 | 1:400 | |
| 37-4 | total | | 1:400 | 1:6400 | |
| 37-5 | medium | | 1:100 | <1:100 | |

EXAMPLE 19

Induction of Dengue Virus-neutralizing Antibodies by Immunizing Mice with 80% E Secreted by *Drosophila melanogaster* Schneider Cells Expressing tPA$_L$-prM80% E and tPA$_L$-80% E Schneider cells, transformed with pMtt-prM80% E and pMtt-80% E expressing the tissue plasminogen activator leader fusion proteins tPA$_L$-prM80% E and tPA$_L$-80% E, respectively (Described in detail in Examples 17 and 13, respectively), were cultured in serum-free medium (Excell; JRH Biosciences) and induced by addition of CuSO$_4$ to a final concentration in the culture medium of 0.2 mM (see examples 13 and 17 for more detail on culture conditions). The cells were maintained in inducing medium for seven days prior to harvesting. The cells were removed by centrifugation at 1000 X G in a Beckman TJ-6 refrigerated centrifuge and the media were filtered through a 0.2 µm cellulose acetate filter (Nalgene). The media containing the recombinant 80% E were concentrated 20-fold using centrifugal concentrators (Centriprep 30; Amicon) and assayed by ELISA (described in detail in Example 7) and Western immunoblots prior to their use as an immunogen in mice. Negative control medium, derived from Schneider cells transformed with pCOHygro only (See Example 13), was produced as described above. In two series of immunizations, outbred Swiss Webster mice (Simonsen) were immunized intraperitoneally (I.P.) with 100 µg total protein in Freund's complete adjuvant. Control animals were immunized with 100 µg of total protein from the concentrated negative control medium, 80 µg of purified Saccharomyces-expressed domain B (see Example 8), or saline only, each in Freund's complete adjuvant. In the first series of immunizations, the mice received three I.P. boosts, consisting of one half the priming dose in Freund's incomplete adjuvant, at two week intervals. In the second series of I.P. immunizations, the mice received two boosts, each at one month intervals.

Following the first and second boosts, the animals were test bled (tail bleed) and the immune response was monitored using an indirect ELISA as described in example 18. Following the final boost, the animals were bled out and the sera were tested for anti-DEN2 responsiveness by indirect ELISA and PRNT as described in Example 18. Results for the ELISA and PRNT assays are summarized in Tables 5 and 6. In both series of immunizations, the mice immunized with the crude media containing 80% E, expressed cotranslationally with prM or independently without prM, developed high titer, virus-neutralizing antibodies. These titers are higher than any previously reported titers for any immunogen produced from any flavivirus, suggesting the utility of these immunogens as efficacious vaccine candidates.

TABLE 5

Immune Response of Mice Immunized with Crude Drosophila Media Containing Dengue 2 Virus 80% E Expressed as a prM 80% E Fusion

| mouse | antigen | adjuvant | 2° titer[a] ELISA | 3° titer[b] ELISA | titer[c] ELISA | PRNT$_{80}$ titer[c] |
|---|---|---|---|---|---|---|
| 20-1 | Saline | Freund's | <1:50 | <1:50 | <1:100 | <1:10 |
| 20-2 | | | <1:50 | <1:50 | <1:100 | <1:10 |
| 20-3 | | | <1:50 | <1:50 | <1:100 | <1:10 |
| 20-4 | | | <1:50 | <1:50 | <1:100 | <1:10 |
| 20-5 | | | <1:50 | <1:50 | <1:100 | <1:10 |
| 21-1 | pCoHygro | Freund's | <1:50 | <1:50 | <1:100 | <1:10 |
| 21-2 | secreted | | <1:50 | <1:50 | <1:100 | <1:10 |
| 21-3 | medium | | <1:50 | <1:50 | <1:100 | <1:10 |
| 21-4 | | | <1:50 | <1:50 | <1:100 | <1:10 |

TABLE 5-continued

Immune Response of Mice Immunized with Crude Drosophila Media Containing Dengue 2 Virus 80% E Expressed as a prM 80% E Fusion

| mouse | antigen | adjuvant | 2° titer[a] ELISA | 3° titer[b] ELISA | titer[c] ELISA | PRNT$_{80}$ titer[c] |
|---|---|---|---|---|---|---|
| 21-5 | | | <1:50 | <1:50 | <1:100 | <1:10 |
| 22-1 | prM 80% E | Freund's | 1:3200 | >1;25,600 | 1:102,400 | 1:2560 |
| 22-2 | secreted | | >1:800 | >1:6,400 | 1:25,600 | 1:2560 |
| 22-3 | medium | | >1:200 | >1:1,600 | 1:25,600 | 1:2560 |
| 22-4 | | | <1:50 | >1:102,400 | >1:102,400 | 1:2560 |
| 22-5 | | | 1:3200 | >1:25,600 | >1:25,600 | 1:640 |

[a]Determined following the 2nd injection.
[b]Determined following the 3rd injection.
[c]Determined following the 4th and final injection.

TABLE 6

Immune Response of Mice Immunized with Crude Drosophila Media Containing Dengue 2 Virus 80% E Expressed with or without prM

| mouse | antigen | adjuvant | 2° titer[a] ELISA | 3° titer[b] ELISA | Final titer[c] ELISA |
|---|---|---|---|---|---|
| 25-1 | Saline | Freund's | <1:50 | >1:50 | <1:10 |
| 25-2 | | | <1:50 | >1:50 | <1:10 |
| 25-3 | | | <1:50 | >1:50 | <1:10 |
| 25-4 | | | <1:50 | >1:50 | <1:10 |
| 25-5 | | | <1:50 | >1:50 | <1:10 |
| 27-1[d] | 80 µg | Freund's | 1:1600 | 1:102,400 | <1:100 |
| 27-2 | Purified | | 1:100 | 1:6400 | 1:10 |
| 27-3 | Sacchro | | >1:6400 | 1:102,400 | <1:100 |
| 27-4 | DomB | | >1:6400 | 1:409,600 | 1:40 |
| 27-5 | | | >1:6400 | 1:409,600 | <1:500 |
| 28-1 | 100 µg | Freund's | DEAD | NT | NT |
| 28-2 | Drosphila | | >1:6400 | 1:102,400 | 1:8000 |
| 28-3 | prM 80% E | | >1:6400 | 1:409,600 | 1:8000 |
| 28-4 | total | | >1:6400 | 1:102,400 | 1:4000 |
| 28-5 | medium | | >1:6400 | 1:102,400 | 1:1000 |
| 29-1 | 100 µg | Freund's | 1:6400 | 1:6400 | 1:500 |
| 29-2 | Drosophila | | 1:6400 | 1:102,400 | 1:4000 |
| 29-3 | 80% E | | <1:100 | 1:25,600 | 1:1000 |
| 29-4 | total | | >1:6400 | 1:25,600 | 1:8000 |
| 29-5 | medium | | >1:6400 | 1:102,400 | 1:4000 |

[a]Determined following the 2nd injection.
[b]Determined following the 3rd injection.
[c]Determined following the 4th and final injection.
[d]mouse 27-1 did not receive second boost.
NT - not tested.

EXAMPLE 20

Protection from Dengue Virus Challenge by Immunizing Mice with 80% E Secreted by *Drosophila melanogaster* Schneider Cells Expressing tPA$_L$-prM80% E or $tPA_L$-80% E Schneider cells, transformed with pMtt-prM80% E and pMtt-80% E expressing the tissue plasminogen activator leader fusion proteins $tPA_L$-prM80% E and $tPA_L$-80% E respectively (described in detail in Examples 17 and 13, respectively), were cultured in serum-free medium (Excell; JRH Biosciences) and induced by addition of $CuSO_4$ to the culture medium at final concentration of 0.2 mM (see examples 13 and 17 for additional details on culture conditions). The cells were maintained in inducing medium for seven days prior to collecting the medium. The cells were removed by centrifugation at 1000 X G in a Beckman TJ-6 refrigerated centrifuge and the media were filtered through a 0.2 μm cellulose acetate filter (Nalgene). The media were concentrated 20-fold using centrifugal ultrafiltration (Centriprep 30, Amicon) and assayed by ELISA and Western immunoblots prior to use as an immunogen in mice. Negative control medium, derived from Schneider cells transformed with pCOHygro only (see Example 13), was produced as described above. These immunogens were used to immunize 10–13 day old Balb/c mice (Jackson Labs). A total of 0.1 ml of each preparation (corresponding to 70 μg total protein from negative control medium, 230 μg total protein from $tPA_L$-80% E medium, and 150 μg total protein from $tPA_L$-prM80% E medium) were used to subcutaneously inoculate groups of 10 mice each, using Alum as adjuvant. An identical second dose was administered 14 days later as a booster. One week after the second dose the mice were challenged with an intracranial injection of 100 $LD_{50}$ units of DEN2 New Guinea C strain ($10^5$ pfu/injection).

The morbidity and mortality of the mice were monitored for 17 days post challenge. Six days after challenge the mice immunized with the negative control medium began exhibiting symptoms of infection including ruffled fur, hindlimb paralysis, wasting, and death. Eight of the 10 negative control mice were dead by day 12 post-challenge and the remaining two mice recovered by day 15 post-challenge. In contrast, of the 10 mice immunized with the $tPA_L$-80% E, only four exhibited any symptoms of infection, and eight of 10 survived the challenge. Similarly, nine of 10 mice immunized with $tPA_L$-prM80% E survived the challenge, although seven of these mice exhibited mild symptoms of infection during the monitoring period. These survival data are illustrated in FIG. 13, and show that both Drosophila-expressed 80% E antigens efficiently protected mice from viral challenge. These results emphasize the utility of the Drosophila cell expressed 80% E dengue immunogens as vaccine candidates.

EXAMPLE 21

Construction of DEN-2 N-terminal 60% E and prM60% E cDNA Fragments

A subclone encoding the N-terminal 60% of E was constructed using p29GEB24PS and p29D280E. Example 1 of the parent application—describes construction of p29GEB24PS. Plasmid p29GEB24PS holds a BamHI fragment insert containing, in part, DEN-2 E sequences (nucleotides 1696–2121) starting at a DEN-2 genomic BamHI site and ending with the Gly395 codon, followed immediately by two stop codons and a SalI site. Oligonucleotide mutagenesis had deleted codons for Leu292 through Lys295 (nucleotides 1810–1821) and had inserted two stop codons and a SalI site immediately following the Lys291 codon (see FIG. 4 and Example 1).

The N-terminal 80% E insert in p29D280E was then converted to a 60% E insert by replacing a restriction fragment encoding the 3' end of 80% E with a restriction fragment from p29GEB24PS encoding the 3' end of 60% E. To accomplish this, DNA of p29GEB24PS was digested with BamHI, the ~590 bp BamHI fragment was isolated by agarose gel electrophoresis and then digested with SalI, and finally the 119 bp BamHI-SalI fragment released from the ~590 bp BamHI fragment and containing dengue nucleotides 1696–1809 was isolated by agarose gel electrophoresis and ligated into p29D280E prepared as follows. Plasmid p29D280E was digested with BamHI, which cuts the BamHI site (dengue nucleotides 1696–1701) within 80% E, and with SalI, which cuts immediately 3' of 80% E and also within the vector, pBR322, 422 base pairs distal to the 3' end of the 80% E fragment. Following ligation, the desired product, a plasmid containing the cDNA encoding the N-terminal 60% of E in pBR322 (p29D260E), was recovered by transformation of *E. coli* with the ligation mixture and screening transformant colonies for plasmids of the appropriate size and restriction digestion pattern. Proper ligation of the BamHI-SalI fragment in p29D260E was confirmed by DNA sequence determination.

To construct a cDNA encoding prM and the amino terminal 60% of E (prM60% E), we used a strategy identical to that used to construct prM80% E (Example 14). The prM100% E plasmid, p29prME13, was digested with BamHI and SalI to release the 794 bp 3' end fragment of E, which was then replaced with the 119 bp BamHI-SalI fragment encoding a 40% carboxy-end truncation of E from p29D260E. The resulting truncated cDNA clone, p48BSprM60E, encodes a prM-60% E fusion ending with Lys291 of E and was confirmed by restriction digestion and DNA sequence analysis.

EXAMPLE 22

Construction of Expression Vector pLS6-60% E and Secretion of 60% E by *Saccharomyces cerevisiae* Expressing MFα-60% E An expression vector (pLS6-60% E) was constructed for secretion of the N-terminal 60% (codons 1–291, 60% E) of the DEN-2 PR-159 S1 envelope glycoprotein from *S. cerevisiae*. The 60% E DNA sequences were obtained from plasmid p29D260E, described in example 21, by restriction endonuclease digestion with both BglII and SalI. The released fragment was isolated by agarose gel electrophoresis and subcloned into the BglII and SalI sites of pLS6, a yeast expression vector described in example 2. The $MF\alpha_L$-60% E fusion was made such that processing of the MFα propeptide and trimming of a Glu-Ala dipeptide results in 60% E with eight additional N-terminal amino acids encoded by sequences present in the multiple cloning site of the pLS6 vector and the E gene PCR primer adaptor (see below). Transcription of the gene fusion is driven by the *S. cerevisiae* copper-inducible copper metallothionein (CUPl) promoter.

After confirming the DNA sequence of the ligated junctions of expression vector pLS6-60% E, the recombinant DNA was transformed into *S. cerevisiae* strain GL43 (MATa trplΔl ura3-52 pep4::URA3; SmithKline Beecham) according to standard protocols (Gutherie & Fink, eds. 1991; Rose et al, 1990). Transformants were selected by their ability to grow on minimal medium (SD medium: Guthrie and Fink, 1991) without tryptophan supplementation.

In order to test for expression and secretion of 60% E, several transformants were grown in small-scale cultures (5 ml medium in 17×150 mm tubes). Single colonies were used to inoculate SD medium and the inoculated cultures were grown to saturation (overnight, 30° C., 220 rpm). $1\times10^8$ cells from the overnight culture were used to inoculate 5 ml of minimal SD medium supplemented with Casamino acids (2 g/l; Difco) and $CuSO_4$ (200 μM). This expression culture was fed with glucose (4 g/l, final concentration) and sodium phosphate (pH 6.7, 20 mM, final concentration) at 24 hours post inoculation and, after 48 hours of growth (30° C., 220 rpm, in 17×150 mm tubes), was harvested by centrifugation. Cell-free spent medium was buffer-exchanged with TEEN (50 mM Tris, 10 mM EDTA, 10 mM EGTA, 150 mM NaCl, pH 8.0) and concentrated 200-fold using Centricon-30 (Amicon) ultrafiltration. An extract of cellular protein was prepared by lysing the yeast cells with vigorous agitation in the presence of glass beads (425–600 μm) and TEEN+PIC (TEEN with 1 μg/ml each of pepstatin and leupeptin and 1 mM phenylmethylsulfonylfluoride) using a Mini Beadbeater apparatus (BioSpec Products, Bartlesville, Okla.). Samples were endoglycosidase $H_f$ digested according to the manufacturer's (New England Biolabs, Beverly, Mass.) protocol prior to SDS-PAGE analysis. Protein gels were Coomassie-stained directly as well as Western blotted and immunoprobed using anti-DEN2 HMAF.

Negative control yeast carrying the expression vector without a Dengue gene insert secreted no proteins recognized by anti-DEN2 HMAF, while pLS6-60% E medium contained several immunoreactive species. The major band presumably represents full-length 60% E since its apparent molecular weight is approximately 10 kD less than that of recombinant 80% E. A protein band comigrating with this immunoreactive material was visible in Coomassie-stained gels of proteins secreted by pLS6-60% E transformants, but this band was absent in medium of negative control transformants. The immunoblot of proteins secreted by pLS6-60% E transformants evidenced a minor band of apparent molecular weight 6–8 kD larger than 60% E; this likely represents unprocessed MFα propeptide-60% E. The cellular protein extract of pLS6-60% E transformants contained many immunoreactive polypeptides not observed in negative control cells; two of these match the secreted products discussed above.

```
                                                 (SEQ ID NO;49 and SEQ ID NO:48)
ATG .....GCT......GAG GCC TTT AGA TCT CGA GTA CCC GGG ACC ATG ...AAA TAA TAG Met-18aa Ala-65aa Glu Ala Phe Arg Ser Arg Val Pro Gly Thr Met1...Lys291End End

▲        ▲      ▲                               60%E

Signalase  Kex2p  DPAP
```

EXAMPLE 23

Construction of Expression Vectors pLS6-prM60% E and pLS6-prM(mutSS)60% E, Expression of MF$\alpha_L$-prM60% E and MF$\alpha_L$-prM(mutSS)60% E in *Saccharomyces cerevisiae*, and Secretion of 60% by *Saccharomyces cerevisiae* Expressing MF$\alpha_L$-prM (mutSS)60% E For expression of DEN-2 PR159/S1 premembrane protein amino acids 1–166 and envelope glycoprotein amino acids 1–291 as a single contiguous open reading frame in *S. cerevisiae*, DNA sequences encoding these proteins were obtained by digestion of plasmid p48BSprM60E (see Example 21) with the restriction enzymes BglII and SalI. This fragment was cloned into the pLS6 *S. cerevisiae* expression vector (see Example 2) that had been digested with BglII and SalI. The structure of the resulting gene fusion expression vector, pLS6-prM60% E, was confirmed by restriction digestion and DNA sequence analysis. The N-terminal MF$\alpha_L$-prM fusion amino acid sequence of the MF$\alpha_L$-prM60% E fusion protein are identical to those described for MF$\alpha_L$-prM(mutSS)80% E fusions (Example 15), while the C-terminal amino acid of the fusion protein is $Lys_{291}$ of the dengue envelope glycoprotein.

The pLS6-prM60% E plasmid was transformed into *S. cerevisiae* strain GL43 (MATa ura3-52 trplΔl pep4::URA3) and screened for 60% E expression as described in Example 11. Proteins secreted into the culture medium as well as cellular proteins were treated with endoglycosidase $H_f$ (EndoH, New England Biolabs, Beverly, Mass.) and separated by SDS-PAGE. Proteins were analyzed by both Coomassie staining of polyacrylamide gels and immunoprobing of Western blots. Similar to the expression of secreted 80% E from pLS6-prM80% E (Example 15), secreted 60% E was not detected on Coomassie stained polyacrylamide gels nor Western blots. An immunoblot of intracellular protein confirmed that the construct (MF$\alpha_L$-prM60% E) was expressed, but the fusion product had not been processed to prM and E (evaluation was performed as described in Example 15).

Because the dengue E signal sequence itself may limit processing of the prME fusion proteins, expression of MF$\alpha_L$-prM(mutSS)60% E was evaluated. The BglII-EcoNI fragment from pLS6-prM(mutSS)100% E-TGA encoding the altered secretion signal peptidase cleavage site (see Example 15) was used to replace the homologous fragment from the pLS6-prM60% E to produce pLS6-prM(mutSS) 60% E. The sequence of the expression plasmid was confirmed by restriction digestion and DNA sequence analysis. Plasmid pLS6prM(mutSS)60% E was transformed into the *S. cerevisiae* GL43 strain and transformants were selected as described in Example 11.

Transformants were cultured, induced, and evaluated as described in Examples 11 and 15. In contrast to the expression of MF$\alpha_L$-prM60% E, Western blot analysis of total intracellular proteins from pLS6-prM(mutSS)60% E transformants demonstrated that the transformed cells produce an approximately 40 kilodalton product recognized by anti-DEN2 HMAF. For analysis of secreted proteins, media from induced cultures were concentrated, treated with endoglycosidase $H_f$, and analyzed on Western blots for E antigen. A small amount of processed 60% E could be identified in the culture medium upon immunoprobing with anti-DEN2 HMAF. Thus, the mutagenesis of the signalase cleavage site resulted in greatly enhanced processing of the MF$\alpha_L$-prM (mutSS)60% E product at the prM-E junction which produced secretion of a processed 60% E from the MF$\alpha_L$-prM (mutSS)60% E in *S. cerevisiae.*

Continuation in Part

EXAMPLE 24

Construction of Expression Vector pPIC9-60% E and Secretion of 60% E by *P. pastoris* Expressing MF$\alpha_L$-60% E The expression vector constructed to secrete 60% E from P. pastoris, pPIC9-60% E, included the DEN-2 PR-159 S1 envelope glycoprotein amino acids 1–291. As a precursor to this 60% E expression vector, a modified pLS6-60% E plasmid (pLS6-alt60% E), encoding a fusion between MF$\alpha_L$ and the amino terminal 60% of the dengue envelope, was constructed that encodes fewer non-dengue amino acids between the MF$\alpha_L$ and E segments. The 60% E cDNA fragment from pLS6-alt60% E was then transferred to pPIC9.

The sequences in pLS6-alt60% E encoding the dengue E protein amino terminus were derived from pLS6-2×80E, which encodes a tandemly arrayed dimer of 80% E that are linked by a synthetic linker peptide. To convert pLS6-2×80E to pLS6-alt60% E, pLS6-2×80E was digested with EcoNI, which cuts within the first member of the 80% E dimer, and SalI, which cuts immediately downstream of the dimer, thereby removing the 3' portion of the first member of the 80E dimer and the second member of the 80E dimer entirely. In its place was ligated an EcoNI-SalI fragment from pLS6-prM(mutSS)60E (see Example 23), encoding the 3' portion of 60% E, to complete construction of pLS6-alt60% E.

The minimizing of non-dengue codons between MF$\alpha_L$ and E, found in pLS6-2×80E, were preserved in pLS6-alt60% E, and, subsequently, in pPIC9-60% E. The codons between MF$\alpha_L$ and E were minimized, owing to use of the XmaI site in p29D280E (XmaI is the first adaptor restriction enzyme site upstream of E; see Example 1) and the StuI site in pLS6. To ligate the XmaI 5' end of E to the StuI site in the MF$\alpha_L$, the XmaI site was treated with Klenow polymerase to make the end blunt during the construction of pLS6-2× 80E.

To transfer 60% E from pLS6-alt60% E to pPIC9, pLS6-alt60E was digested by XhoI plus SalI, which released a fragment that includes a portion of the MFα leader and the entire 60% E coding region. This fragment was ligated with the Pichia expression vector pPIC9 (Invitrogen, San Diego, Calif.; described in Example 12) that was previously digested with the restriction enzyme XhoI. This ligation restored the complete MFα leader sequence including the Kex2 cleavage site. The genetic integrity of the resulting gene fusion expression vector, pPIC9-60% E, was confirmed by restriction digestion and DNA sequence analysis. The partial nucleotide and predicted amino acid sequences of the MF$\alpha_L$-60% E fusion gene are shown below:

```
                                        (SEQ ID NO: 49 and SEQ ID NO:50)
ATG ......... GAG GCC GGG ACC ATG ... AAA      TAA
Met-18aa-65aa Glu Ala Gly Thr Met1 ... Lys291 END
         ▲     ▲       ▲
  Signalase  Kex2p    DPAP
```

The location of the signalase and Kex2 cleavage sites which remove the pre and pro portions of the MFα leader peptide, respectively, are indicated. The dengue sequences are indicated in bold type. The $Met_1$ residue is the N-terminal amino acid of the E glycoprotein and $Lys_{291}$ is residue 291 from the amino terminal end of the envelope glycoprotein. The expression of a recombinant product in Pichia from the pPIC9 vector is driven by the methanol inducible promoter derived from the *Pichia pastoris* aoxl (alcohol oxidase 1) gene.

The pPIC9-60% E expression vector was transformed into spheroplasts of *P. pastoris* strain GS115 (his4) and transformants were selected for their ability to grow on minimal medium without histidine supplementation. Strain GS115 and the protocol used for transformation were obtained from Invitrogen (San Diego, Calif.). Transformants were tested for their ability to express and secrete 60% E by growing selected clones in small cultures (5 ml). The transformants were grown to saturation (24 to 36 hrs.) in BMGY medium (1% yeast extract, 2% peptone, 100 mM potassium phosphate, pH 6.0, 1.34% yeast nitrogen base without amino acids, $4\times10^{-5}$% biotin, 1% glycerol). The cells were collected by centrifugation and suspended in one half the original culture volume with BMMY (identical to BMGY except the glycerol component of BMGY is replaced in BMMY with 0.5% methanol) medium and cultured for 48 hrs. Proteins secreted into the culture medium, as well as cellular proteins, were treated with endoglycosidase $H_f$ (EndoH, New England Biolabs, Beverly, Mass.) and separated by SDS-PAGE. Western immunoblots probed with DEN-2 HMAF indicated that the recombinants expressed significant levels of 60% E. Protein gels analyzed by Coomassie staining also showed strong levels of 60% E expression and secretion.

EXAMPLE 25

Construction of Expression Vector pPIC9-prM (mutSS)60% E and Secretion of 60% E by *P. pastoris* Expressing $MF\alpha_L$-prM(mutSS)60% E To construct clone pPIC9-prM(mutSS)60% E, a strategy identical to that describe in Example 16 was used. Clone pLS6-prM(mutSS)60% E (described in Example 23) was digested with restriction endonuclease XhoI and XmaI and sequences within the $MF\alpha_L$ and dengue cloning adaptor were replaced by oligonucleotides to remove an extraneous XhoI site, to preserve a critical XhoI site, and to regenerate the Kex2 protease process site. The XhoI-SalI prM(mutSS) 60% E fragment from pLS6Δ-prM(mutSS)60% E was ligated into the unique XhoI site of pPIC9. The nucleotide and amino acid sequences at the N-terminus of the fusion protein are identical to that shown in Example 16 for pLS6Δ-prM(mutSS)80% E. The structure of the Pichia expression vector pPIC9-prM(mutSS)60% E was confirmed by restriction digestion and DNA sequence analysis.

The pPIC9-prM(mutSS)60% E expression vector was transformed into spheroplasts of *P. pastoris* strain GS115 (his4), and transformants were selected and evaluated as described in Example 12. After EndoH$_f$ treatment of secreted proteins, a novel Coomassie Blue-staining band could be detected by SDS-PAGE. Immunoprobing with anti-domain B serum of Western blots of proteins prepared from the culture medium detected a diffuse area of reactivity ranging from 40 to 90 kD in the non-EndoH treated samples and a unique band of approximately 40 kD in the EndoH$_f$ treated samples that corresponds to the band observed following Coomassie Blue staining.

EXAMPLE 26

Construction of pMttbns-prM100% E, Expression of tPa-prM100% E by *Drosophila melanogaster* Schneider Cells, and Induction of a Virus Neutralizing Response by Immunizing Mice with tPa-prM100% E Membrane Preparations For expression of DEN-2 PR159/S1 preMembrane protein amino acids 1–166 and Envelope glycoprotein amino acids 1–495 as a single continuous open reading frame in *Drosophila melanogaster* Schneider 2 tissue culture cells, DNA sequences encoding these proteins were obtained by digestion of the p48BSprME13 clone (described in Example 14) with the restriction enzymes BglII and SalI. This fragment was cloned into the unique BglII and XhoI restriction sites of plasmid pMttΔXho (described in Example 13).

The cloning junctions of the resulting gene fusion expression vector, pMttprM100E, were confirmed by restriction endonuclease digestion and DNA sequence analysis. The partial nucleotide and predicted amino acid sequences of the $tPA_1$-prM100E fusion gene are:

```
                                                        (SEQ ID NO:51 and SEQ ID NO:52)
ATG .............. GGAGCCAGATCTCGAGTACCCGGGACCATG TTT ..ACA    ATG ..GCC   TAA
Met-20 aa- -11 aa-GlyAlaArgSerArgValProGlyThrMet Phe1..Thr166 Met1..Ala495END
      pre▲pro-tPA▲                                  prM          100%E
```

The TPA pre- and propeptide regions are delineated by pre▼ and pro-tpA▼, respectively, and the dengue sequences are indicated in bold type. The $Phe_1$ and $Thr_{166}$ residues are the N-terminal and C-terminal amino acid residues of prM, respectively. The $Met_1$ residue is the N-terminal amino acid of envelope glycoprotein and $Ala_{495}$ is residue 495 from the amino terminal end of the envelope glycoprotein (the carboxy-terminal residue).

As described previously in Example 13, Schneider 2 cells were cotransfected with pMttprM100% E DNA at ratios of 1:1, and 5:1, relative to pCOHygro DNA and selected for growth in medium containing 300 μg/ml hygromycin. Transfectants were induced with 200 μM $CUSO_4$ and expression of prM100% E was examined at various times after induction. Proteins secreted into the culture medium as well as cellular proteins were separated by SDS-PAGE. Protein gels were analyzed by both Coomassie Blue staining and immunoprobing of corresponding Western blots. Analysis of Coomassie Blue-stained SDS-PAGE gels failed to reveal a unique protein band either intracellularly or in the culture medium. However, a novel band was recognized intracellularly by polyclonal anti-dengue 2 hyperimmune mouse ascites fluid (anti-DEN-2 HMAF, gift of R. Putnak, WRAIR) in Western blot analysis. This ~60 kD immunoreactive band comigrated with viral Envelope derived from dengue-2 infected mosquito C6/36 cells suggesting the recombinant 100% E protein had been processed away from the premembrane protein. Polyclonal antisera to the pr portion of prM (from Peter Wright, Monash University, Australia) recognized a ~20 kD protein, which comigrated with viral prM, confirming that the 100% E produced in the transfected cells was processed from prM. In fact, no evidence of a higher molecular weight band that might correspond to unprocessed prM100% E was detected in any sample, suggesting that the proteolytic processing of prM from E is extremely efficient in Schneider cells. No 100% E was detected in the culture medium indicating that 100% E remains anchored in cell-associated membranes.

Immunoblots probed with anti-DEN-2 HMAF demonstrated that the amount of intracellular 100% E produced by the transfectants increased over time from day 1 post induction to 7 days post induction. The amount of 100% E detected intracellularly in the transfectants correlated with the cotransfection ratio. Sensitivity of the intracellular 100% E to endoglycosidases was evaluated by molecular weight shift of the protein in SDS-PAGE and Western immunoblots following endoglycosidase treatment. Partial resistance of the recombinant 100% E to Endoglycosidase $H_f$ (Endo $H_f$; New England Biolabs) digestion indicated that the product contains N-linked glycosylation, and that the composition of the recombinant products probably represents a mixture of complex, high mannose, and/or hybrid glycosylation.

Schneider cells, transformed with pMtt-prM100% E expressing the tissue plasminogen activator leader fusion protein $tPA_L$-prM100% E were cultured in serum-free medium (Excell; JRH Biosciences) and induced by addition of $CuSO_4$ to a final concentration in the culture medium of 0.2 nM (see Examples 13 and 17 for more detail on culture conditions). The cells were maintained in inducing medium for seven days prior to harvesting. The cells were harvested by centrifugation at 1000 X G in a Beckman TJ-6 refrigerated centrifuge. The cells were washed one time with phosphate buffer saline (PBS), resuspended in PBS and disrupted with a tissue homogenizer. Undisrupted cells were removed by centrifugation at 1000 X G in an Eppendorf microcentrifuge. Cellular membranes were pelleted at 10,000 X G in an Eppendorf microcentrifuge and 100,000 X G in a Beckman L8-80M Ultracentrifuge. The 10,000 X G and 100,000 X G pellets were resuspended in PBS and pooled for mouse immunization. Negative control cells transformed with pCOHygro only (see Example 13) were cultured, induced, and harvested as described for the prM100% E-expressing cells. The immunogens were assayed by Western blot prior to immunization of mice.

Outbred Swiss Webster mice (Simonsen) were immunized intraperitoneally (I.P.) with 75 μg total protein of the prM100% E membrane preparation in Freund's complete adjuvant. Control animals were immunized with either 75 μg of total protein from the negative control membrane preparation or with saline only, each in Freund's complete adjuvant. The mice received three I.P. boosts, consisting of one half the priming dose in Freund's incomplete adjuvant, at two week intervals.

Following the first and second boosts, the animals were test bled (tail bleed) and the immune response was monitored using an indirect ELISA as described in Example 18. One week after the final boost, the animals were bled out and the sera were tested for anti-DEN2 responsiveness by indirect ELISA and PRNT as described in Example 18. Results for the ELISA and PRNT assays are summarized in Table 7. The mice immunized with the membrane preparation containing 100% E developed virus-neutralizing antibodies despite the crude nature of the immunogen, suggesting the utility of these immunogens as efficacious vaccine candidates.

TABLE 7

Immune Response of Mice Immunized with Recombinant Dengue prM100% E Membrane Preparation

| mouse | antigen | adjuvant | 2° titer[a] ELISA | 3° titer[b] ELISA | final titer ELISA | $PRNT_{80}$ titer[b] |
|---|---|---|---|---|---|---|
| 20-1 | Saline | Freund's | <1:50 | <1:50 | <1:100 | <1:10 |
| 20-2 | | | <1:50 | <1:50 | <1:100 | <1:10 |
| 20-3 | | | <1:50 | <1:50 | <1:100 | <1:10 |
| 20-4 | | | <1:50 | <1:50 | <1:100 | <1:10 |
| 20-5 | | | <1:50 | <1:50 | <1:100 | <1:10 |
| 23-1 | pCoHygro | Freund's | <1:50 | <1:50 | <1:100 | <1:10 |
| 23-2 | membrane | | <1:50 | <1:50 | <1:100 | <1:10 |
| 23-3 | | | <1:50 | <1:50 | <1:100 | <1:10 |
| 23-4 | | | <1:50 | <1:50 | <1:100 | <1:10 |
| 23-5 | | | <1:50 | <1:50 | <1:100 | <1:10 |
| 24-1 | prM 100% E | Freund's | 1:200 | 1:1,600 | >1:25600 | 1:320 |
| 24-2 | membrane | | <1:50 | >1:1600 | >1:1600 | 1:320 |
| 24-3 | | | <1:50 | >1:6000 | >1:1600 | 1:80 |
| 24-4 | | | <1:50 | >1:6000 | >1:25600 | 1:640 |
| 24-5 | | | <1:50 | <1:50 | 1:400 | 1:20 |

[a]Indirect ELISA titer using recombinant domain B as coating antigen.
[b]80% reduction of plaque titer of DEN-2 NGC virus on Vero cells.

What is claimed is:

1. An immunogenic composition which generates protective, neutralizing antibody responses to a Flavivirus in a murine host which responses confer protection against intracerebral challenge by the homologous Flavivirus, said strain of Flavivirus selected from the group consisting of a strain of dengue, a strain of Japanese encephalitis virus (JEV), a strain of yellow fever virus (YF), and a strain of tick-borne encephalitis virus (TBE)

which composition contains an adjuvant; and a portion of the envelope protein (E) of the Flavivirus strain against which said responses are sought, which portion is 80% E, wherein said 80% E represents that portion of the envelope protein that constitutes 80% of its length starting from amino acid 1 at its N-terminus and which portion has been secreted as a recombinantly produced protein from Drosophila cells.

2. The immunogenic composition of claim 1 wherein said Drosophila cells are *D. melanogaster* Schneider cells.

3. The immunogenic composition of claim 1 wherein said adjuvant is an alum adjuvant.

4. An immunogenic composition which generates a neutralizing antibody response to a Flavivirus in a murine host against the homologous Flavivirus, said strain of Flavivirus selected from the group consisting of a strain of dengue, a strain of Japanese encephalitis virus (JEV), a strain of yellow fever virus (YF), and a strain of tick-borne encephalitis virus (TBE)

which composition contains an adjuvant; and a portion of the envelope protein (E) of the Flavivirus strain against which generation of said response is sought, which portion is 80% E, wherein said 80% E represents that portion of the envelope protein that constitutes 80% of its length starting from amino acid 1 at its N-terminus, and which portion has been secreted as a recombinantly produced protein from Drosophila cells.

5. The immunogenic composition of claim 4 wherein said Drosophila cells are Schneider cells.

6. The immunogenic composition of claim 4 wherein said Flavivirus is a dengue virus.

7. The immunogenic composition of claim 4 wherein the 80% E is encoded in a DNA construct operably linked downstream from human tissue plasminogen activator prepropeptide secretion leader ($tPA_L$).

8. The immunogenic composition of claim 4 wherein the adjuvant is an alum adjuvant.

9. A method to generate a neutralizing antibody response in a non-human subject against a Flavivirus strain, said strain selected from the group consisting of a strain of dengue, a strain of YF, a strain of JEV, and a strain of TBE, which method comprises administering to a non-human subject in need of generating said response an effective amount of the immunogenic composition of claim 4.

10. The method of claim 9 wherein said Flavivirus is a dengue virus.

11. The immunogenic composition of claim 1 wherein the 80% E is encoded in a DNA construct operably linked downstream from a human tissue plasminogen activator prepropeptide secretion leader ($tPA_L$) sequence.

12. The immunogenic composition of claim 1 wherein said Flavivirus is a dengue virus.

13. The immunogenic composition of claim 2 wherein the Flavirirus is a dengue virus.

* * * * *

SEQUENCE LISTING

```
(1) GENERAL INFORMATION:

(iii) NUMBER OF SEQUENCES: 52

(2) INFORMATION FOR SEQ ID NO:1:

(i) SEQUENCE CHARACTERISTICS:
          (A) LENGTH: 3381 base pairs
          (B) TYPE: nucleic acid
          (C) STRANDEDNESS: single
          (D) TOPOLOGY: linear
```

-continued (ii) MOLECULE TYPE: cDNA (vi) ORIGINAL SOURCE:
(A) ORGANISM: Dengue virus
(B) STRAIN: Serotype 2 (Den-2)

(vii) IMMEDIATE SOURCE:
(B) CLONE: Den-2 PR159/S1

(ix) FEATURE:
(A) NAME/KEY: misc_feature
(B) LOCATION: group(103, 1940, 1991, 2025)
(D) OTHER INFORMATION: /note= "Positions in the S1 strain representing corrections to the wild type DEN-2 PR159 strain reported by Hahn(Citation #1)"
/citation= ([1])

(ix) FEATURE:
(A) NAME/KEY: misc_feature
(B) LOCATION: 1218
(D) OTHER INFORMATION: /note= "G is replaced by A for Wild-Type sequence"

(ix) FEATURE:
(A) NAME/KEY: misc_feature
(B) LOCATION: 1260
(D) OTHER INFORMATION: /note= "T is replaced by G for Wild-Type sequence"

(ix) FEATURE:
(A) NAME/KEY: misc_feature
(B) LOCATION: 1762
(D) OTHER INFORMATION: /note= "G is replaced by A for Wild-Type sequence"

(ix) FEATURE:
(A) NAME/KEY: misc_feature
(B) LOCATION: 1929
(D) OTHER INFORMATION: /note= "C is replaced by T for Wild-Type sequence"

(ix) FEATURE:
(A) NAME/KEY: misc_feature
(B) LOCATION: 2310
(D) OTHER INFORMATION: /note= "A is replaced by N for Wild-Type sequence"

(ix) FEATURE:
(A) NAME/KEY: misc_feature
(B) LOCATION: 1
(D) OTHER INFORMATION: /note= "Start of coding strand sequence for Capsid."

(ix) FEATURE:
(A) NAME/KEY: misc_feature
(B) LOCATION: 343
(D) OTHER INFORMATION: /note= "Start of coding strand sequence for preMembrane"

(ix) FEATURE:
(A) NAME/KEY: misc_feature
(B) LOCATION: 616
(D) OTHER INFORMATION: /note= "Start of coding strand sequence for Membrane"

(ix) FEATURE:
(A) NAME/KEY: misc_feature
(B) LOCATION: 841
(D) OTHER INFORMATION: /note= "Start of coding strand sequence for Envelope"

(ix) FEATURE:
(A) NAME/KEY: misc_feature
(B) LOCATION: 2326
(D) OTHER INFORMATION: /note= "Start of coding strand sequence for NS1"

(x) PUBLICATION INFORMATION:
    (A) AUTHORS: Hahn, Y.S.
    (C) JOURNAL: Virology
    (D) VOLUME: 162
    (F) PAGES: 167-180
    (G) DATE: 1988

(xi) SEQUENCE DESCRIPTION: SEQ ID NO:1:

| | | | | | | |
|---|---|---|---|---|---|---|
| ATGAATAACC | AACGGAAAAA | GGCGAGAAAC | ACGCCTTTCA | ATATGCTGAA | ACGCGAGAGA | 60 |
| AACCGCGTGT | CAACTGTACA | ACAGTTGACA | AAGAGATTCT | CACTTGGAAT | GCTGCAGGGA | 120 |
| CGAGGACCAC | TAAAATTGTT | CATGGCCCTG | GTGGCATTCC | TTCGTTTCCT | AACAATCCCA | 180 |
| CCAACAGCAG | GGATATTAAA | AAGATGGGGA | ACAATTAAAA | AATCAAAGGC | TATTAATGTT | 240 |
| CTGAGAGGCT | TCAGGAAAGA | GATTGGAAGG | ATGCTGAATA | TCTTAAACAG | AGACGTAGA | 300 |
| ACTGCAGGCA | TGATCATCAT | GCTGATTCCA | ACAGTGATGG | CGTTTCATCT | GACCACACGC | 360 |
| AACGGAGAAC | CACACATGAT | CGTCAGTAGA | CAAGAAAAAG | GGAAAAGCCT | TCTGTTTAAG | 420 |
| ACAAAGGACG | GCACGAACAT | GTGTACCCTC | ATGGCCATGG | ACCTTGGTGA | GTTGTGTGAA | 480 |
| GACACAATCA | CGTATAAATG | TCCCTTTCTC | AAGCAGAACG | AACCAGAAGA | CATAGATTGT | 540 |
| TGGTGCAACT | CCACGTCCAC | ATGGGTAACT | TATGGGACAT | GTACCACCAC | AGGAGAGCAC | 600 |
| AGAAGAGAAA | AAAGATCAGT | GGCGCTTGTT | CCACACGTGG | GAATGGGATT | GGAGACACGA | 660 |
| ACTGAAACAT | GGATGTCATC | AGAAGGGGCC | TGGAAACATG | CCCAGAGAAT | TGAAACTTGG | 720 |
| ATTCTGAGAC | ATCCAGGCTT | TACCATAATG | GCCGCAATCC | TGGCATACAC | CATAGGAACG | 780 |
| ACGCATTTCC | AAAGAGTCCT | GATATTCATC | CTACTGACAG | CCATCGCTCC | TTCAATGACA | 840 |
| ATGCGCTGCA | TAGGAATATC | AAATAGGGAC | TTTGTGGAAG | GAGTGTCAGG | AGGGAGTTGG | 900 |
| GTTGACATAG | TTTTAGAACA | TGGAAGTTGT | GTGACGACGA | TGGCAAAAAA | TAAACCAACA | 960 |
| CTGGACTTTG | AACTGATAAA | AACAGAAGCC | AAACAACCCG | CCACCTTAAG | GAAGTACTGT | 1020 |
| ATAGAGGCTA | AACTGACCAA | CACGACAACA | GACTCGCGCT | GCCCAACACA | AGGGGAACCC | 1080 |
| ACCCTGAATG | AAGAGCAGGA | CAAAAGGTTT | GTCTGCAAAC | ATTCCATGGT | AGACAGAGGA | 1140 |
| TGGGGAAATG | GATGTGGATT | ATTTGGAAAA | GGAGGCATCG | TGACCTGTGC | CATGTTCACA | 1200 |
| TGCAAAAAGA | ACATGGAGGG | AAAAATTGTG | CAGCCAGAAA | ACCTGGAATA | CACTGTCGTT | 1260 |
| ATAACACCTC | ATTCAGGGGA | AGAACATGCA | GTCGGAAATG | ACACAGGAAA | ACATGGTAAA | 1320 |
| GAAGTCAAGA | TAACACCACA | GAGCTCCATC | ACAGAGGCGG | AACTGACAGG | CTATGGCACT | 1380 |
| GTTACGATGG | AGTGCTCTCC | AAGAACGGGC | CTCGACTTCA | ATGAGATGGT | GTTGCTGCAA | 1440 |
| ATGAAAGACA | AAGCTTGGCT | GGTGCACAGA | CAATGGTTCC | TAGACCTACC | GTTGCCATGG | 1500 |
| CTGCCCGGAG | CAGACACACA | AGGATCAAAT | TGGATACAGA | AAGAGACACT | GGTCACCTTC | 1560 |
| AAAAATCCCC | ATGCGAAAAA | ACAGGATGTT | GTTGTCTTAG | GATCCCAAGA | GGGGGCCATG | 1620 |
| CATACAGCAC | TCACAGGGGC | TACGGAAATC | CAGATGTCAT | CAGGAAACCT | GCTGTTCACA | 1680 |
| GGACATCTTA | AGTGCAGGCT | GAGAATGGAC | AAATTACAAC | TTAAAGGGAT | GTCATACTCC | 1740 |
| ATGTGCACAG | GAAAGTTTAA | AGTTGTGAAG | GAAATAGCAG | AAACACAACA | TGGAACAATA | 1800 |
| GTCATTAGAG | TACAATATGA | AGGAGACGGC | TCTCCATGCA | AGATCCCTTT | TGAGATAATG | 1860 |
| GATCTGGAAA | AAAGACATGT | TTTGGGCCGC | CTGATCACAG | TCAACCCAAT | TGTAACAGAA | 1920 |
| AAGGACAGCC | CAGTCAACAT | AGAAGCAGAA | CCTCCATTCG | GAGACAGCTA | CATCATCATA | 1980 |
| GGAGTGGAAC | CAGGACAATT | GAAGCTGGAC | TGGTTCAAGA | AAGGAAGTTC | CATCGGCCAA | 2040 |
| ATGTTTGAGA | CAACAATGAG | GGGAGCGAAA | AGAATGGCCA | TTTTGGGCGA | CACAGCCTGG | 2100 |

```
GATTTTGGAT CTCTGGGAGG AGTGTTCACA TCAATAGGAA AGGCTCTCCA CCAGGTTTTT      2160

GGAGCAATCT ACGGGGCTGC TTTCAGTGGG GTCTCATGGA CTATGAAGAT CCTCATAGGA      2220

GTTATCATCA CATGGATAGG AATGAACTCA CGTAGCACAT CACTGTCTGT GTCACTGGTA      2280

TTAGTGGGAA TCGTGACACT GTACTTGGGA GTTATGGTGC AGGCCGATAG TGGTTGCGTT      2340

GTGAGCTGGA AGAACAAAGA ACTAAAATGT GGCAGTGGAA TATTCGTCAC AGATAACGTG      2400

CATACATGGA CAGAACAATA CAAGTTCCAA CCAGAATCCC CTTCAAAACT GGCTTCAGCC      2460

ATCCAGAAAG CTCATGAAGA GGGCATCTGT GGAATCCGCT CAGTAACAAG ACTGGAAAAT      2520

CTTATGTGGA AACAAATAAC ATCAGAATTG AATCATATTC TATCAGAAAA TGAAGTGAAA      2580

CTGACCATCA TGACAGGAGA CATCAAAGGA ATCATGCAGG TAGGAAAACG ATCTCTGCGG      2640

CCTCAACCCA CTGAGTTGAG GTATTCATGG AAAACATGGG GTAAAGCGAA AATGCTCTCC      2700

ACAGAACTCC ATAATCAGAC CTTCCTCATT GATGGTCCCG AAACAGCAGA ATGCCCCAAC      2760

ACAAACAGAG CTTGGAATTC ACTAGAAGTT GAGGACTACG GCTTTGGAGT ATTCACTACC      2820

AATATATGGC TAAGATTGAG AGAAAAGCAG GATGCATTTT GTGACTCAAA ACTCATGTCA      2880

GCGGCCATAA AGGACAACAG AGCCGTCCAT GCTGATATGG GTTATTGGAT AGAAAGCGCA      2940

CTCAATGATA CATGGAAGAT AGAGAAAGCT TCTTTCATTG AAGTCAAAAG TTGCCACTGG      3000

CCAAAGTCAC ACACTCTATG GAGTAATGGA GTGCTAGAAA GCGAGATGGT AATTCCAAAG      3060

AATTTCGCTG GACCAGTGTC ACAACATAAT AACAGACCAG CTATCACAC ACAAACAGCA       3120

GGACCTTGGC ATCTAGGCAA GCTTGAGATG GACTTTGATT TCTGCGAAGG GACTACAGTG      3180

GTGGTAACCG AGGACTGTGG AAACAGAGGG CCCTCTTTAA GAACAACCAC TGCCTCAGGA      3240

AAACTCATAA CGGAATGGTG TTGTCGATCT TGCACACTAC CACCACTAAG ATACAGAGGT      3300

GAGGATGGAT GCTGGTACGG GATGGAAATC AGACCATTGA AAGAGAAAGA AGAAAATCTG      3360

GTCAGTTCTC TGGTCACAGC C                                                3381
```

(2) INFORMATION FOR SEQ ID NO:2:

(i) SEQUENCE CHARACTERISTICS:
        (A) LENGTH: 3381 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Dengue virus
        (B) STRAIN: Serotype 2(DEN-2)

(vii) IMMEDIATE SOURCE:
        (B) CLONE: Den-2 PR159/S1

(ix) FEATURE:
        (A) NAME/KEY: CDS
        (B) LOCATION: 1..3381

(ix) FEATURE:
        (A) NAME/KEY: misc_feature
        (B) LOCATION: 1216..1218
        (D) OTHER INFORMATION: /note= "GAG(coding for Glu) is
            replaced by GAA(coding for Glu) for the wild-type
            DEN-2 PR159 strain(Citation #1)"
            /citation= ([1])

&

DEN-2 PR159 Strain(Citation #1)"
            /citation= ([1])

(ix) FEATURE:
        (A) NAME/KEY: misc_feature
        (B) LOCATION: 1762..1764
        (D) OTHER INFORMATION: /note= "ATT(coding for Ile) is
            replaced by GTT(coding for Val) for the wild-type
            DEN-2 PR159 strain(citation #1)"
            /citation= ([1])

(ix) FEATURE:
        (A) NAME/KEY: misc_feature
        (B) LOCATION: 1927..1929
        (D) OTHER INFORMATION: /note= "AGT(Coding for Ser) is
            replaced by AGC(coding for Ser) for the wild-type
            DEN-2 PR159 strain(citation #1)"
            /citation= ([1])

(ix) FEATURE:
        (A) NAME/KEY: misc_feature
        (B) LOCATION: 1
        (D) OTHER INFORMATION: /note= "Start of coding strand
            sequence for Capsid"

(ix) FEATURE:
        (A) NAME/KEY: misc_feature
        (B) LOCATION: 343
        (D) OTHER INFORMATION: /note= "Start of coding strand
            sequence for preMembrane"

(ix) FEATURE:
        (A) NAME/KEY: misc_feature
        (B) LOCATION: 616
        (D) OTHER INFORMATION: /note= "Start of coding strand
            sequence of Membrane"

(ix) FEATURE:
        (A) NAME/KEY: misc_feature
        (B) LOCATION: 841
        (D) OTHER INFORMATION: /note= "Start of coding strand
            sequence of Envelope"

(ix) FEATURE:
        (A) NAME/KEY: misc_feature
        (B) LOCATION: 2326
        (D) OTHER INFORMATION: /note= "Start of coding strand
            sequence for NS1"

(x) PUBLICATION INFORMATION:
        (A) AUTHORS: Hahn, Y.S.
        (C) JOURNAL: Virology
        (D) VOLUME: 162
        (F) PAGES: 167-180
        (G) DATE: 1988

(xi) SEQUENCE DESCRIPTION: SEQ ID NO:2:

ATG AAT AAC CAA CGG AAA AAG GCG AGA AAC ACG CCT TTC AAT ATG CTG        48
Met Asn Asn Gln Arg Lys Lys Ala Arg Asn Thr Pro Phe Asn Met Leu
 1               5                  10                  15

AAA CGC GAG AGA AAC CGC GTG TCA ACT GTA CAA CAG TTG ACA AAG AGA        96
Lys Arg Glu Arg Asn Arg Val Ser Thr Val Gln Gln Leu Thr Lys Arg
             20                  25                  30

TTC TCA CTT GGA ATG CTG CAG GGA CGA GGA CCA CTA AAA TTG TTC ATG       144
Phe Ser Leu Gly Met Leu Gln Gly Arg Gly Pro Leu Lys Leu Phe Met
         35                  40                  45

GCC CTG GTG GCA TTC CTT CGT TTC CTA ACA ATC CCA CCA ACA GCA GGG       192
Ala Leu Val Ala Phe Leu Arg Phe Leu Thr Ile Pro Pro Thr Ala Gly
     50                  55                  60

ATA TTA AAA AGA TGG GGA ACA ATT AAA AAA TCA AAG GCT ATT AAT GTT       240
Ile Leu Lys Arg Trp Gly Thr Ile Lys Lys Ser Lys Ala Ile Asn Val
 65                  70                  75                  80

```
CTG AGA GGC TTC AGG AAA GAG ATT GGA AGG ATG CTG AAT ATC TTA AAC      288
Leu Arg Gly Phe Arg Lys Glu Ile Gly Arg Met Leu Asn Ile Leu Asn
                85                  90                  95

AGG AGA CGT AGA ACT GCA GGC ATG ATC ATC ATG CTG ATT CCA ACA GTG      336
Arg Arg Arg Arg Thr Ala Gly Met Ile Ile Met Leu Ile Pro Thr Val
            100                 105                 110

ATG GCG TTT CAT CTG ACC ACA CGC AAC GGA GAA CCA CAC ATG ATC GTC      384
Met Ala Phe His Leu Thr Thr Arg Asn Gly Glu Pro His Met Ile Val
        115                 120                 125

AGT AGA CAA GAA AAA GGG AAA AGC CTT CTG TTT AAG ACA AAG GAC GGC      432
Ser Arg Gln Glu Lys Gly Lys Ser Leu Leu Phe Lys Thr Lys Asp Gly
    130                 135                 140

ACG AAC ATG TGT ACC CTC ATG GCC ATG GAC CTT GGT GAG TTG TGT GAA      480
Thr Asn Met Cys Thr Leu Met Ala Met Asp Leu Gly Glu Leu Cys Glu
145                 150                 155                 160

GAC ACA ATC ACG TAT AAA TGT CCC TTT CTC AAG CAG AAC GAA CCA GAA      528
Asp Thr Ile Thr Tyr Lys Cys Pro Phe Leu Lys Gln Asn Glu Pro Glu
                165                 170                 175

GAC ATA GAT TGT TGG TGC AAC TCC ACG TCC ACA TGG GTA ACT TAT GGG      576
Asp Ile Asp Cys Trp Cys Asn Ser Thr Ser Thr Trp Val Thr Tyr Gly
            180                 185                 190

ACA TGT ACC ACC ACA GGA GAG CAC AGA AGA GAA AAA AGA TCA GTG GCG      624
Thr Cys Thr Thr Thr Gly Glu His Arg Arg Glu Lys Arg Ser Val Ala
        195                 200                 205

CTT GTT CCA CAC GTG GGA ATG GGA TTG GAG ACA CGA ACT GAA ACA TGG      672
Leu Val Pro His Val Gly Met Gly Leu Glu Thr Arg Thr Glu Thr Trp
    210                 215                 220

ATG TCA TCA GAA GGG GCC TGG AAA CAT GCC CAG AGA ATT GAA ACT TGG      720
Met Ser Ser Glu Gly Ala Trp Lys His Ala Gln Arg Ile Glu Thr Trp
225                 230                 235                 240

ATT CTG AGA CAT CCA GGC TTT ACC ATA ATG GCC GCA ATC CTG GCA TAC      768
Ile Leu Arg His Pro Gly Phe Thr Ile Met Ala Ala Ile Leu Ala Tyr
                245                 250                 255

ACC ATA GGA ACG ACG CAT TTC CAA AGA GTC CTG ATA TTC ATC CTA CTG      816
Thr Ile Gly Thr Thr His Phe Gln Arg Val Leu Ile Phe Ile Leu Leu
            260                 265                 270

ACA GCC ATC GCT CCT TCA ATG ACA ATG CGC TGC ATA GGA ATA TCA AAT      864
Thr Ala Ile Ala Pro Ser Met Thr Met Arg Cys Ile Gly Ile Ser Asn
        275                 280                 285

AGG GAC TTT GTG GAA GGA GTG TCA GGA GGG AGT TGG GTT GAC ATA GTT      912
Arg Asp Phe Val Glu Gly Val Ser Gly Gly Ser Trp Val Asp Ile Val
    290                 295                 300

TTA GAA CAT GGA AGT TGT GTG ACG ACG ATG GCA AAA AAT AAA CCA ACA      960
Leu Glu His Gly Ser Cys Val Thr Thr Met Ala Lys Asn Lys Pro Thr
305                 310                 315                 320

CTG GAC TTT GAA CTG ATA AAA ACA GAA GCC AAA CAA CCC GCC ACC TTA     1008
Leu Asp Phe Glu Leu Ile Lys Thr Glu Ala Lys Gln Pro Ala Thr Leu
                325                 330                 335

AGG AAG TAC TGT ATA GAG GCT AAA CTG ACC AAC ACG ACA ACA GAC TCG     1056
Arg Lys Tyr Cys Ile Glu Ala Lys Leu Thr Asn Thr Thr Thr Asp Ser
            340                 345                 350

CGC TGC CCA ACA CAA GGG GAA CCC ACC CTG AAT GAA GAG CAG GAC AAA     1104
Arg Cys Pro Thr Gln Gly Glu Pro Thr Leu Asn Glu Glu Gln Asp Lys
        355                 360                 365

AGG TTT GTC TGC AAA CAT TCC ATG GTA GAC AGA GGA TGG GGA AAT GGA     1152
Arg Phe Val Cys Lys His Ser Met Val Asp Arg Gly Trp Gly Asn Gly
    370                 375                 380

TGT GGA TTA TTT GGA AAA GGA GGC ATC GTG ACC TGT GCC ATG TTC ACA     1200
Cys Gly Leu Phe Gly Lys Gly Gly Ile Val Thr Cys Ala Met Phe Thr
385                 390                 395                 400
```

```
TGC AAA AAG AAC ATG GAG GGA AAA ATT GTG CAG CCA GAA AAC CTG GAA          1248
Cys Lys Lys Asn Met Glu Gly Lys Ile Val Gln Pro Glu Asn Leu Glu
                405                 410                 415

TAC ACT GTC GTT ATA ACA CCT CAT TCA GGG GAA GAA CAT GCA GTC GGA          1296
Tyr Thr Val Val Ile Thr Pro His Ser Gly Glu Glu His Ala Val Gly
            420                 425                 430

AAT GAC ACA GGA AAA CAT GGT AAA GAA GTC AAG ATA ACA CCA CAG AGC          1344
Asn Asp Thr Gly Lys His Gly Lys Glu Val Lys Ile Thr Pro Gln Ser
        435                 440                 445

TCC ATC ACA GAG GCG GAA CTG ACA GGC TAT GGC ACT GTT ACG ATG GAG          1392
Ser Ile Thr Glu Ala Glu Leu Thr Gly Tyr Gly Thr Val Thr Met Glu
    450                 455                 460

TGC TCT CCA AGA ACG GGC CTC GAC TTC AAT GAG ATG GTG TTG CTG CAA          1440
Cys Ser Pro Arg Thr Gly Leu Asp Phe Asn Glu Met Val Leu Leu Gln
465                 470                 475                 480

ATG AAA GAC AAA GCT TGG CTG GTG CAC AGA CAA TGG TTC CTA GAC CTA          1488
Met Lys Asp Lys Ala Trp Leu Val His Arg Gln Trp Phe Leu Asp Leu
                485                 490                 495

CCG TTG CCA TGG CTG CCC GGA GCA GAC ACA CAA GGA TCA AAT TGG ATA          1536
Pro Leu Pro Trp Leu Pro Gly Ala Asp Thr Gln Gly Ser Asn Trp Ile
            500                 505                 510

CAG AAA GAG ACA CTG GTC ACC TTC AAA AAT CCC CAT GCG AAA AAA CAG          1584
Gln Lys Glu Thr Leu Val Thr Phe Lys Asn Pro His Ala Lys Lys Gln
        515                 520                 525

GAT GTT GTT GTC TTA GGA TCC CAA GAG GGG GCC ATG CAT ACA GCA CTC          1632
Asp Val Val Val Leu Gly Ser Gln Glu Gly Ala Met His Thr Ala Leu
    530                 535                 540

ACA GGG GCT ACG GAA ATC CAG ATG TCA TCA GGA AAC CTG CTG TTC ACA          1680
Thr Gly Ala Thr Glu Ile Gln Met Ser Ser Gly Asn Leu Leu Phe Thr
545                 550                 555                 560

GGA CAT CTT AAG TGC AGG CTG AGA ATG GAC AAA TTA CAA CTT AAA GGG          1728
Gly His Leu Lys Cys Arg Leu Arg Met Asp Lys Leu Gln Leu Lys Gly
                565                 570                 575

ATG TCA TAC TCC ATG TGC ACA GGA AAG TTT AAA GTT GTG AAG GAA ATA          1776
Met Ser Tyr Ser Met Cys Thr Gly Lys Phe Lys Val Val Lys Glu Ile
            580                 585                 590

GCA GAA ACA CAA CAT GGA ACA ATA GTC ATT AGA GTA CAA TAT GAA GGA          1824
Ala Glu Thr Gln His Gly Thr Ile Val Ile Arg Val Gln Tyr Glu Gly
        595                 600                 605

GAC GGC TCT CCA TGC AAG ATC CCT TTT GAG ATA ATG GAT CTG GAA AAA          1872
Asp Gly Ser Pro Cys Lys Ile Pro Phe Glu Ile Met Asp Leu Glu Lys
    610                 615                 620

AGA CAT GTT TTG GGC CGC CTG ATC ACA GTC AAC CCA ATT GTA ACA GAA          1920
Arg His Val Leu Gly Arg Leu Ile Thr Val Asn Pro Ile Val Thr Glu
625                 630                 635                 640

AAG GAC AGC CCA GTC AAC ATA GAA GCA GAA CCT CCA TTC GGA GAC AGC          1968
Lys Asp Ser Pro Val Asn Ile Glu Ala Glu Pro Pro Phe Gly Asp Ser
                645                 650                 655

TAC ATC ATC ATA GGA GTG GAA CCA GGA CAA TTG AAG CTG GAC TGG TTC          2016
Tyr Ile Ile Ile Gly Val Glu Pro Gly Gln Leu Lys Leu Asp Trp Phe
            660                 665                 670

AAG AAA GGA AGT TCC ATC GGC CAA ATG TTT GAG ACA ACA ATG AGG GGA          2064
Lys Lys Gly Ser Ser Ile Gly Gln Met Phe Glu Thr Thr Met Arg Gly
        675                 680                 685

GCG AAA AGA ATG GCC ATT TTG GGC GAC ACA GCC TGG GAT TTT GGA TCT          2112
Ala Lys Arg Met Ala Ile Leu Gly Asp Thr Ala Trp Asp Phe Gly Ser
    690                 695                 700

CTG GGA GGA GTG TTC ACA TCA ATA GGA AAG GCT CTC CAC CAG GTT TTT          2160
Leu Gly Gly Val Phe Thr Ser Ile Gly Lys Ala Leu His Gln Val Phe
705                 710                 715                 720
```

```
GGA GCA ATC TAC GGG GCT GCT TTC AGT GGG GTC TCA TGG ACT ATG AAG      2208
Gly Ala Ile Tyr Gly Ala Ala Phe Ser Gly Val Ser Trp Thr Met Lys
                725                 730                 735

ATC CTC ATA GGA GTT ATC ATC ACA TGG ATA GGA ATG AAC TCA CGT AGC      2256
Ile Leu Ile Gly Val Ile Ile Thr Trp Ile Gly Met Asn Ser Arg Ser
        740                 745                 750

ACA TCA CTG TCT GTG TCA CTG GTA TTA GTG GGA ATC GTG ACA CTG TAC      2304
Thr Ser Leu Ser Val Ser Leu Val Leu Val Gly Ile Val Thr Leu Tyr
            755                 760                 765

TTG GGA GTT ATG GTG CAG GCC GAT AGT GGT TGC GTT GTG AGC TGG AAG      2352
Leu Gly Val Met Val Gln Ala Asp Ser Gly Cys Val Val Ser Trp Lys
        770                 775                 780

AAC AAA GAA CTA AAA TGT GGC AGT GGA ATA TTC GTC ACA GAT AAC GTG      2400
Asn Lys Glu Leu Lys Cys Gly Ser Gly Ile Phe Val Thr Asp Asn Val
785                 790                 795                 800

CAT ACA TGG ACA GAA CAA TAC AAG TTC CAA CCA GAA TCC CCT TCA AAA      2448
His Thr Trp Thr Glu Gln Tyr Lys Phe Gln Pro Glu Ser Pro Ser Lys
                805                 810                 815

CTG GCT TCA GCC ATC CAG AAA GCT CAT GAA GAG GGC ATC TGT GGA ATC      2496
Leu Ala Ser Ala Ile Gln Lys Ala His Glu Glu Gly Ile Cys Gly Ile
            820                 825                 830

CGC TCA GTA ACA AGA CTG GAA AAT CTT ATG TGG AAA CAA ATA ACA TCA      2544
Arg Ser Val Thr Arg Leu Glu Asn Leu Met Trp Lys Gln Ile Thr Ser
        835                 840                 845

GAA TTG AAT CAT ATT CTA TCA GAA AAT GAA GTG AAA CTG ACC ATC ATG      2592
Glu Leu Asn His Ile Leu Ser Glu Asn Glu Val Lys Leu Thr Ile Met
850                 855                 860

ACA GGA GAC ATC AAA GGA ATC ATG CAG GTA GGA AAA CGA TCT CTG CGG      2640
Thr Gly Asp Ile Lys Gly Ile Met Gln Val Gly Lys Arg Ser Leu Arg
865                 870                 875                 880

CCT CAA CCC ACT GAG TTG AGG TAT TCA TGG AAA ACA TGG GGT AAA GCG      2688
Pro Gln Pro Thr Glu Leu Arg Tyr Ser Trp Lys Thr Trp Gly Lys Ala
                885                 890                 895

AAA ATG CTC TCC ACA GAA CTC CAT AAT CAG ACC TTC CTC ATT GAT GGT      2736
Lys Met Leu Ser Thr Glu Leu His Asn Gln Thr Phe Leu Ile Asp Gly
            900                 905                 910

CCC GAA ACA GCA GAA TGC CCC AAC ACA AAC AGA GCT TGG AAT TCA CTA      2784
Pro Glu Thr Ala Glu Cys Pro Asn Thr Asn Arg Ala Trp Asn Ser Leu
        915                 920                 925

GAA GTT GAG GAC TAC GGC TTT GGA GTA TTC ACT ACC AAT ATA TGG CTA      2832
Glu Val Glu Asp Tyr Gly Phe Gly Val Phe Thr Thr Asn Ile Trp Leu
930                 935                 940

AGA TTG AGA GAA AAG CAG GAT GCA TTT TGT GAC TCA AAA CTC ATG TCA      2880
Arg Leu Arg Glu Lys Gln Asp Ala Phe Cys Asp Ser Lys Leu Met Ser
945                 950                 955                 960

GCG GCC ATA AAG GAC AAC AGA GCC GTC CAT GCT GAT ATG GGT TAT TGG      2928
Ala Ala Ile Lys Asp Asn Arg Ala Val His Ala Asp Met Gly Tyr Trp
                965                 970                 975

ATA GAA AGC GCA CTC AAT GAT ACA TGG AAG ATA GAG AAA GCT TCT TTC      2976
Ile Glu Ser Ala Leu Asn Asp Thr Trp Lys Ile Glu Lys Ala Ser Phe
            980                 985                 990

ATT GAA GTC AAA AGT TGC CAC TGG CCA AAG TCA CAC ACT CTA TGG AGT      3024
Ile Glu Val Lys Ser Cys His Trp Pro Lys Ser His Thr Leu Trp Ser
        995                 1000                1005

AAT GGA GTG CTA GAA AGC GAG ATG GTA ATT CCA AAG AAT TTC GCT GGA      3072
Asn Gly Val Leu Glu Ser Glu Met Val Ile Pro Lys Asn Phe Ala Gly
    1010                1015                1020

CCA GTG TCA CAA CAT AAT AAC AGA CCA GGC TAT CAC ACA CAA ACA GCA      3120
Pro Val Ser Gln His Asn Asn Arg Pro Gly Tyr His Thr Gln Thr Ala
1025                1030                1035                1040
```

```
GGA CCT TGG CAT CTA GGC AAG CTT GAG ATG GAC TTT GAT TTC TGC GAA      3168
Gly Pro Trp His Leu Gly Lys Leu Glu Met Asp Phe Asp Phe Cys Glu
                1045                1050                1055

GGG ACT ACA GTG GTG GTA ACC GAG GAC TGT GGA AAC AGA GGG CCC TCT      3216
Gly Thr Thr Val Val Val Thr Glu Asp Cys Gly Asn Arg Gly Pro Ser
                1060                1065                1070

TTA AGA ACA ACC ACT GCC TCA GGA AAA CTC ATA ACG GAA TGG TGT TGT      3264
Leu Arg Thr Thr Thr Ala Ser Gly Lys Leu Ile Thr Glu Trp Cys Cys
                1075                1080                1085

CGA TCT TGC ACA CTA CCA CCA CTA AGA TAC AGA GGT GAG GAT GGA TGC      3312
Arg Ser Cys Thr Leu Pro Pro Leu Arg Tyr Arg Gly Glu Asp Gly Cys
                1090                1095                1100

TGG TAC GGG ATG GAA ATC AGA CCA TTG AAA GAG AAA GAA GAA AAT CTG      3360
Trp Tyr Gly Met Glu Ile Arg Pro Leu Lys Glu Lys Glu Glu Asn Leu
1105                1110                1115                1120

GTC AGT TCT CTG GTC ACA GCC                                           3381
Val Ser Ser Leu Val Thr Ala
                1125
```

(2) INFORMATION FOR SEQ ID NO:3:

(i) SEQUENCE CHARACTERISTICS:
        (A) LENGTH: 1127 amino acids
        (B) TYPE: amino acid
        (D) TOPOLOGY: linear (ii) MOLECULE TYPE: protein (xi) SEQUENCE DESCRIPTION: SEQ ID NO:3:

```
Met Asn Asn Gln Arg Lys Lys Ala Arg Asn Thr Pro Phe Asn Met Leu
1               5                   10                  15

Lys Arg Glu Arg Asn Arg Val Ser Thr Val Gln Gln Leu Thr Lys Arg
                20                  25                  30

Phe Ser Leu Gly Met Leu Gln Gly Arg Gly Pro Leu Lys Leu Phe Met
            35                  40                  45

Ala Leu Val Ala Phe Leu Arg Phe Leu Thr Ile Pro Pro Thr Ala Gly
        50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Thr Ala Gly Met Ile Ile Met Leu Ile Pro Thr Val
                100                 105                 110

Met Ala Phe His Leu Thr Thr Arg Asn Gly Glu Pro His Met Ile Val
            115                 120                 125

Ser Arg Gln Glu Lys Gly Lys Ser Leu Leu Phe Lys Thr Lys Asp Gly
        130                 135                 140

Thr Asn Met Cys Thr Leu Met Ala Met Asp Leu Gly Glu Leu Cys Glu
145                 150                 155                 160

Asp Thr Ile Thr Tyr Lys Cys Pro Phe Leu Lys Gln Asn Glu Pro Glu
                165                 170                 175

Asp Ile Asp Cys Trp Cys Asn Ser Thr Ser Thr Trp Val Thr Tyr Gly
                180                 185                 190

Thr Cys Thr Thr Thr Gly Glu His Arg Arg Glu Lys Arg Ser Val Ala
            195                 200                 205

Leu Val Pro His Val Gly Met Gly Leu Glu Thr Arg Thr Glu Thr Trp
        210                 215                 220
```

-continued

```
Met Ser Ser Glu Gly Ala Trp Lys His Ala Gln Arg Ile Glu Thr Trp
225                 230                 235                 240

Ile Leu Arg His Pro Gly Phe Thr Ile Met Ala Ala Ile Leu Ala Tyr
                245                 250                 255

Thr Ile Gly Thr Thr His Phe Gln Arg Val Leu Ile Phe Ile Leu Leu
            260                 265                 270

Thr Ala Ile Ala Pro Ser Met Thr Met Arg Cys Ile Gly Ile Ser Asn
        275                 280                 285

Arg Asp Phe Val Glu Gly Val Ser Gly Ser Trp Val Asp Ile Val
    290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Asp Ser
            340                 345                 350

Arg Cys Pro Thr Gln Gly Glu Pro Thr Leu Asn Glu Glu Gln Asp Lys
        355                 360                 365

Arg Phe Val Cys Lys His Ser Met Val Asp Arg Gly Trp Gly Asn Gly
    370                 375                 380

Cys Gly Leu Phe Gly Lys Gly Ile Val Thr Cys Ala Met Phe Thr
385                 390                 395                 400

Cys Lys Lys Asn Met Glu Gly Lys Ile Val Gln Pro Glu Asn Leu Glu
                405                 410                 415

Tyr Thr Val Val Ile Thr Pro His Ser Gly Glu Glu His Ala Val Gly
            420                 425                 430

Asn Asp Thr Gly Lys His Gly Lys Glu Val Lys Ile Thr Pro Gln Ser
        435                 440                 445

Ser Ile Thr Glu Ala Glu Leu Thr Gly Tyr Gly Thr Val Thr Met Glu
    450                 455                 460

Cys Ser Pro Arg Thr Gly Leu Asp Phe Asn Glu Met Val Leu Leu Gln
465                 470                 475                 480

Met Lys Asp Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
            500                 505                 510

Gln Lys Glu Thr Leu Val Thr Phe Lys Asn Pro His Ala Lys Lys Gln
        515                 520                 525

Asp Val Val Leu Gly Ser Gln Glu Gly Ala Met His Thr Ala Leu
    530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Val Val Lys Glu Ile
            580                 585                 590

Ala Glu Thr Gln His Gly Thr Ile Val Ile Arg Val Gln Tyr Glu Gly
        595                 600                 605

Asp Gly Ser Pro Cys Lys Ile Pro Phe Glu Ile Met Asp Leu Glu Lys
    610                 615                 620

Arg His Val Leu Gly Arg Leu Ile Thr Val Asn Pro Ile Val Thr Glu
625                 630                 635                 640
```

-continued

```
Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Asp Trp Phe
                660                 665                 670

Lys Lys Gly Ser Ser Ile Gly Gln Met Phe Glu Thr Thr Met Arg Gly
                675                 680                 685

Ala Lys Arg Met Ala Ile Leu Gly Asp Thr Ala Trp Asp Phe Gly Ser
690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser
                740                 745                 750

Thr Ser Leu Ser Val Ser Leu Val Leu Val Gly Ile Val Thr Leu Tyr
                755                 760                 765

Leu Gly Val Met Val Gln Ala Asp Ser Gly Cys Val Val Ser Trp Lys
770                 775                 780

Asn Lys Glu Leu Lys Cys Gly Ser Gly Ile Phe Val Thr Asp Asn Val
785                 790                 795                 800

His Thr Trp Thr Glu Gln Tyr Lys Phe Gln Pro Glu Ser Pro Ser Lys
                805                 810                 815

Leu Ala Ser Ala Ile Gln Lys Ala His Glu Glu Gly Ile Cys Gly Ile
                820                 825                 830

Arg Ser Val Thr Arg Leu Glu Asn Leu Met Trp Lys Gln Ile Thr Ser
                835                 840                 845

Glu Leu Asn His Ile Leu Ser Glu Asn Glu Val Lys Leu Thr Ile Met
850                 855                 860

Thr Gly Asp Ile Lys Gly Ile Met Gln Val Gly Lys Arg Ser Leu Arg
865                 870                 875                 880

Pro Gln Pro Thr Glu Leu Arg Tyr Ser Trp Lys Thr Trp Gly Lys Ala
                885                 890                 895

Lys Met Leu Ser Thr Glu Leu His Asn Gln Thr Phe Leu Ile Asp Gly
                900                 905                 910

Pro Glu Thr Ala Glu Cys Pro Asn Thr Asn Arg Ala Trp Asn Ser Leu
                915                 920                 925

Glu Val Glu Asp Tyr Gly Phe Gly Val Phe Thr Thr Asn Ile Trp Leu
930                 935                 940

Arg Leu Arg Glu Lys Gln Asp Ala Phe Cys Asp Ser Lys Leu Met Ser
945                 950                 955                 960

Ala Ala Ile Lys Asp Asn Arg Ala Val His Ala Asp Met Gly Tyr Trp
                965                 970                 975

Ile Glu Ser Ala Leu Asn Asp Thr Trp Lys Ile Glu Lys Ala Ser Phe
                980                 985                 990

Ile Glu Val Lys Ser Cys His Trp Pro Lys Ser His Thr Leu Trp Ser
                995                1000                1005

Asn Gly Val Leu Glu Ser Glu Met Val Ile Pro Lys Asn Phe Ala Gly
           1010                1015                1020

Pro Val Ser Gln His Asn Asn Arg Pro Gly Tyr His Thr Gln Thr Ala
1025                1030                1035                1040

Gly Pro Trp His Leu Gly Lys Leu Glu Met Asp Phe Asp Phe Cys Glu
                1045                1050                1055
```

```
Gly Thr Thr Val Val Thr Glu Asp Cys Gly Asn Arg Gly Pro Ser
        1060            1065            1070

Leu Arg Thr Thr Thr Ala Ser Gly Lys Leu Ile Thr Glu Trp Cys Cys
        1075            1080            1085

Arg Ser Cys Thr Leu Pro Pro Leu Arg Tyr Arg Gly Glu Asp Gly Cys
        1090            1095            1100

Trp Tyr Gly Met Glu Ile Arg Pro Leu Lys Glu Lys Glu Glu Asn Leu
1105            1110            1115            1120

Val Ser Ser Leu Val Thr Ala
            1125
```

(2) INFORMATION FOR SEQ ID NO:4:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:4:

```
GGAGTATGAC ATCCCAGCTG TCGACTATCA TTTGTCCATT CTCAGCC                47
```

(2) INFORMATION FOR SEQ ID NO:5:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..27

(ix) FEATURE:
        (A) NAME/KEY: CDS
        (B) LOCATION: 37..63

(ix) FEATURE:
        (A) NAME/KEY: misc_feature
        (B) LOCATION: 1..22
        (D) OTHER INFORMATION: /note= "Residues 1693 to 1714 of
            SEQ ID NO:1"

(ix) FEATURE:
        (A) NAME/KEY: misc_feature
        (B) LOCATION: 37..63
        (D) OTHER INFORMATION: /note= "Residues 1726 to 1848 of
            SEQ ID NO:1"

(xi) SEQUENCE DESCRIPTION: SEQ ID NO:5:

```
TGC AGG CTG AGA ATG GAC AAA TGA TAG TCGACAGCT GGG ATG TCA TAC     48
Cys Arg Leu Arg Met Asp Lys  *   *            Gly Met Ser Tyr
        1130            1135                    1

TCC ATG TGC ACA GGA                                               63
Ser Met Cys Thr Gly
  5
```

(2) INFORMATION FOR SEQ ID NO:6:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:6:

Cys Arg Leu Arg Met Asp Lys
 1               5

(2) INFORMATION FOR SEQ ID NO:7:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:7:

Gly Met Ser Tyr Ser Met Cys Thr Gly
 1               5

(2) INFORMATION FOR SEQ ID NO:8:

(i) SEQUENCE CHARACTERISTICS:
        (A) LENGTH: 564 base pairs
        (B) TYPE: nucleic acid
        (C) STRANDEDNESS: single
        (D) TOPOLOGY: linear (vi) ORIGINAL SOURCE:
        (A) ORGANISM: Saccharomyces cerevisiae (ix) FEATURE:
        (A) NAME/KEY: CDS
        (B) LOCATION: 1..564

(xi) SEQUENCE DESCRIPTION: SEQ ID NO:8:

```
ATGAGATTTC CTTCAATTTT TACTGCAGTT TTATTCGCAG CATCCTCCGC ATTAGCTGCT      60

CCAGTCAACA CTACAACAGA AGATGAAACG GCACAAATTC CGGCTGAAGC TGTCATCGGT     120

TACTCAGATT TAGAAGGGGA TTTCGATGTT GCTGTTTTGC CATTTTCCAA CAGCACAAAT     180

AACGGGTTAT TGTTTATAAA TACTACTATT GCCAGCATTG CTGCTAAAGA AGAAGGGGTA     240

TCTCTCGAGA AAAGGGAGGC TGGGATGTCA TACTCCATGT GCACAGGAAA GTTTAAAGTT     300

GTGAAGGAAA TAGCAGAAAC ACAACATGGA ACAATAGTCA TTAGAGTACA ATATGAAGGA     360

GACGGCTCTC CATGCAAGAT CCCTTTTGAG ATAATGGATC TGGAAAAAAG ACATGTTTTG     420

GGCCGCCTGA TCACAGTCAA TCCAATTGTA ACAGAAAAGG ACAGCCCAGT CAACATAGAA     480

GCAGAACCTC CATTCGGAGA CAGCTACATC ATCATAGGAG TGGAACCAGG ACAATTGAAG     540

CTGGACTGGT TCAAGAAAGG ATAA                                           564
```

(2) INFORMATION FOR SEQ ID NO:9:

(i) SEQUENCE CHARACTERISTICS:
        (A) LENGTH: 187 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Cleavage-site
        (B) LOCATION: (19^20)
        (D) OTHER INFORMATION: /note= "Signalase cleavage"

(ix) FEATURE:
        (A) NAME/KEY: Cleavage-site
        (B) LOCATION: (85^86)
        (D) OTHER INFORMATION: /note= "Kex2p cleavage"

```
            (ix) FEATURE:
                (A) NAME/KEY: Peptide
                (B) LOCATION: 1..19
                (D) OTHER INFORMATION: /note= "MF-alpha secretion signal
                    peptide"

(ix) FEATURE:
                (A) NAME/KEY: Peptide
                (B) LOCATION: 20..85
                (D) OTHER INFORMATION: /note= "MF-alpha propeptide"

(ix) FEATURE:
                (A) NAME/KEY: Domain
                (B) LOCATION: 86..187
                (D) OTHER INFORMATION: /note= "Domain B"

(xi) SEQUENCE DESCRIPTION: SEQ ID NO:9:

Met Arg Phe Pro Ser Ile Phe Thr Ala Val Leu Phe Ala Ala Ser Ser
1               5                  10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
50                  55                  60

Phe Ile Asn Thr Thr Ile Ala Ser Ile Ala Ala Lys Glu Glu Gly Val
65                  70                  75                  80

Ser Leu Glu Lys Arg Glu Ala Gly Met Ser Tyr Ser Met Cys Thr Gly
                85                  90                  95

Lys Phe Lys Val Val Lys Glu Ile Ala Glu Thr Gln His Gly Thr Ile
                100                 105                 110

Val Ile Arg Val Gln Tyr Glu Gly Asp Gly Ser Pro Cys Lys Ile Pro
            115                 120                 125

Phe Glu Ile Met Asp Leu Glu Lys Arg His Val Leu Gly Arg Leu Ile
130                 135                 140

Thr Val Asn Pro Ile Val Thr Glu Lys Asp Ser Pro Val Asn Ile Glu
145                 150                 155                 160

Ala Glu Pro Pro Phe Gly Asp Ser Tyr Ile Ile Ile Gly Val Glu Pro
                165                 170                 175

Gly Gln Leu Lys Leu Asp Trp Phe Lys Lys Gly
                180                 185

(2) INFORMATION FOR SEQ ID NO:10:

(i) SEQUENCE CHARACTERISTICS:
            (A) LENGTH: 417 base pairs
            (B) TYPE: nucleic acid
            (C) STRANDEDNESS: double
            (D) TOPOLOGY: linear (ii) MOLECULE TYPE: DNA (genomic)

(vi) ORIGINAL SOURCE:
            (A) ORGANISM: Drosophila (vii) IMMEDIATE SOURCE:
            (B) CLONE: p29GEB2.4PS (ix) FEATURE:
            (A) NAME/KEY: sig_peptide
            (B) LOCATION: 1..60
            (D) OTHER INFORMATION: /note= "1 tPA Secretion Signal"
```

-continued

```
    (ix) FEATURE:
         (A) NAME/KEY: mat_peptide
         (B) LOCATION: 94..417
         (D) OTHER INFORMATION: /note= "1 RGARSP-domB"

(ix) FEATURE:
         (A) NAME/KEY: misc_feature
         (B) LOCATION: 112
         (D) OTHER INFORMATION: /note= "Beginning of Domain B
             region"

(ix) FEATURE:
         (A) NAME/KEY: misc_feature
         (B) LOCATION: 61..93
         (D) OTHER INFORMATION: /note= "1 tPA Propeptide"

(ix) FEATURE:
         (A) NAME/KEY: CDS
         (B) LOCATION: 1..417

(xi) SEQUENCE DESCRIPTION: SEQ ID NO:10:

ATG GAT GCA ATG AAG AGA GGG CTC TGC TGT GTG CTG CTG TGT GGA         48
Met Asp Ala Met Lys Arg Gly Leu Cys Cys Val Leu Leu Leu Cys Gly
-31 -30              -25                 -20

GCA GTC TTC GTT TCG CCC AGC CAG GAA ATC CAT GCC CGA TTC AGA AGA    96
Ala Val Phe Val Ser Pro Ser Gln Glu Ile His Ala Arg Phe Arg Arg
-15              -10                 -5                         1

GGA GCC AGA TCC CCT GGG ATG TCA TAC TCC ATG TGC ACA GGA AAG TTT   144
Gly Ala Arg Ser Pro Gly Met Ser Tyr Ser Met Cys Thr Gly Lys Phe
                 5                  10                  15

AAA ATT GTG AAG GAA ATA GCA GAA ACA CAA CAT GGA ACA ATA GTC ATT   192
Lys Ile Val Lys Glu Ile Ala Glu Thr Gln His Gly Thr Ile Val Ile
             20                  25                  30

AGA GTA CAA TAT GAA GGA GAC GGC TCT CCA TGC AAG ATC CCT TTT GAG   240
Arg Val Gln Tyr Glu Gly Asp Gly Ser Pro Cys Lys Ile Pro Phe Glu
         35                  40                  45

ATA ATG GAT CTG GAA AAA AGA CAT GTT TTG GGC CGC CTG ATC ACA GTC   288
Ile Met Asp Leu Glu Lys Arg His Val Leu Gly Arg Leu Ile Thr Val
     50                  55                  60                  65

AAC CCA ATT GTA ACA GAA AAG GAC AGT CCA GTC AAC ATA GAA GCA GAA   336
Asn Pro Ile Val Thr Glu Lys Asp Ser Pro Val Asn Ile Glu Ala Glu
                 70                  75                  80

CCT CCA TTC GGA GAC AGC TAC ATC ATC ATA GGA GTG GAA CCA GGA CAA   384
Pro Pro Phe Gly Asp Ser Tyr Ile Ile Ile Gly Val Glu Pro Gly Gln
             85                  90                  95

TTG AAG CTG GAC TGG TTC AAG AAA GGA TAA TAG                       417
Leu Lys Leu Asp Trp Phe Lys Lys Gly *   *
         100                 105

(2) INFORMATION FOR SEQ ID NO:11:

(i) SEQUENCE CHARACTERISTICS:
         (A) LENGTH: 137 amino acids
         (B) TYPE: amino acid
         (D) TOPOLOGY: linear (ii) MOLECULE TYPE: protein (xi) SEQUENCE DESCRIPTION: SEQ ID NO:11:

Met Asp Ala Met Lys Arg Gly Leu Cys Cys Val Leu Leu Leu Cys Gly
-31 -30              -25                 -20

Ala Val Phe Val Ser Pro Ser Gln Glu Ile His Ala Arg Phe Arg Arg
-15              -10                 -5                         1

Gly Ala Arg Ser Pro Gly Met Ser Tyr Ser Met Cys Thr Gly Lys Phe
                 5                  10                  15
```

```
Lys Ile Val Lys Glu Ile Ala Glu Thr Gln His Gly Thr Ile Val Ile
            20                  25                  30

Arg Val Gln Tyr Glu Gly Asp Gly Ser Pro Cys Lys Ile Pro Phe Glu
        35                  40                  45

Ile Met Asp Leu Glu Lys Arg His Val Leu Gly Arg Leu Ile Thr Val
 50                  55                  60                  65

Asn Pro Ile Val Thr Glu Lys Asp Ser Pro Val Asn Ile Glu Ala Glu
                70                  75                  80

Pro Pro Phe Gly Asp Ser Tyr Ile Ile Ile Gly Val Glu Pro Gly Gln
            85                  90                  95

Leu Lys Leu Asp Trp Phe Lys Lys Gly
        100                 105
```

(2) INFORMATION FOR SEQ ID NO:12:

(i) SEQUENCE CHARACTERISTICS:
        (A) LENGTH: 417 base pairs
        (B) TYPE: nucleic acid
        (C) STRANDEDNESS: double
        (D) TOPOLOGY: linear (vi) ORIGINAL SOURCE:
        (A) ORGANISM: Drosophila (xi) SEQUENCE DESCRIPTION: SEQ ID NO:12:

```
CTATTATCCT TTCTTGAACC AGTCCAGCTT CAATTGTCCT GGTTCCACTC CTATGATGAT      60

GTAGCTGTCT CCGAATGGAG GTTCTGCTTC TATGTTGACT GGACTGTCCT TTTCTGTTAC     120

AATTGGGTTG ACTGTGATCA GGCGGCCCAA AACATGTCTT TTTTCCAGAT CCATTATCTC     180

AAAAGGGATC TTGCATGGAG AGCCGTCTCC TTCATATTGT ACTCTAATGA CTATTGTTCC     240

ATGTTGTGTT TCTGCTATTT CCTTCACAAT TTTAAACTTT CCTGTGCACA TGGAGTATGA     300

CATCCCAGGG GATCTGGCTC CTCTTCTGAA TCGGGCATGG ATTTCCTGGC TGGGCGAAAC     360

GAAGACTGCT CCACACAGCA GCAGCACACA GCAGAGCCCT CTCTTCATTG CATCCAT       417
```

(2) INFORMATION FOR SEQ ID NO:13:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (vi) ORIGINAL SOURCE:
        (A) ORGANISM: Dengue virus (ix) FEATURE:
        (A) NAME/KEY: misc_feature
        (B) LOCATION: 27..46
        (D) OTHER INFORMATION: /note= "Residues 841 to 860 of SEQ
            ID NO:1"

(xi) SEQUENCE DESCRIPTION: SEQ ID NO:13:

```
CTTCTAGATC TCGAGTACCC GGGACCATGC GCTGCATAGG AATATC                   46
```

(2) INFORMATION FOR SEQ ID NO:14:

(i) SEQUENCE CHARACTERISTICS:
        (A) LENGTH: 35 base pairs
        (B) TYPE: nucleic acid
        (C) STRANDEDNESS: single
        (D) TOPOLOGY: linear

```
    (ix) FEATURE:
         (A) NAME/KEY: misc_feature
         (B) LOCATION: 20..35
         (D) OTHER INFORMATION: /note= "Complementary DNA to
             nucleotides 2010-2025 of SEQ ID NO:1."

(xi) SEQUENCE DESCRIPTION: SEQ ID NO:14:

GCTCTAGAGT CGACTATTAT CCTTTCTTGA ACCAG                                       35

(2) INFORMATION FOR SEQ ID NO:15:

(i) SEQUENCE CHARACTERISTICS:
         (A) LENGTH: 16 amino acids
         (B) TYPE: amino acid
         (C) STRANDEDNESS: single
         (D) TOPOLOGY: linear (xi) SEQUENCE DESCRIPTION: SEQ ID NO:15:

Glu Ala Gly Met Ser Tyr Ser Met Xaa Thr Gly Lys Phe Xaa Val Val
1               5                   10                  15

(2) INFORMATION FOR SEQ ID NO:16:

(i) SEQUENCE CHARACTERISTICS:
         (A) LENGTH: 35 base pairs
         (B) TYPE: nucleic acid
         (C) STRANDEDNESS: single
         (D) TOPOLOGY: linear (ix) FEATURE:
         (A) NAME/KEY: misc_feature
         (B) LOCATION: 20..35
         (D) OTHER INFORMATION: /note= "Complementary DNA to
             nucleotides 2160-2175 of SEQ ID NO:1."

(xi) SEQUENCE DESCRIPTION: SEQ ID NO:16:

GCTCTAGAGT CGACTATTAC CCGTAGATTG CTCCG                                       35

(2) INFORMATION FOR SEQ ID NO:17:

(i) SEQUENCE CHARACTERISTICS:
         (A) LENGTH: 50 base pairs
         (B) TYPE: nucleic acid
         (C) STRANDEDNESS: single
         (D) TOPOLOGY: linear (xi) SEQUENCE DESCRIPTION: SEQ ID NO:17:

CTAGCGGTAC CCTCGAGAAA AGGGAGGCCG GGATGTCATA CTCCATGTGC                       50

(2) INFORMATION FOR SEQ ID NO:18:

(i) SEQUENCE CHARACTERISTICS:
         (A) LENGTH: 42 base pairs
         (B) TYPE: nucleic acid
         (C) STRANDEDNESS: single
         (D) TOPOLOGY: linear (ix) FEATURE:
         (A) NAME/KEY: misc_feature
         (B) LOCATION: 25..42
         (D) OTHER INFORMATION: /note= "Corresponding DNA to
             nucleotides 2062-2079 of SEQ ID NO:1."

(xi) SEQUENCE DESCRIPTION: SEQ ID NO:18:

CGTGTGTCGA CGCGGCCGCT ATTAGGCCAT TCTTTTCGCT CC                               42
```

(2) INFORMATION FOR SEQ ID NO:19:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..48

(ix) FEATURE:
        (A) NAME/KEY: -
        (B) LOCATION: (3^4)
        (D) OTHER INFORMATION: /note= "Representing Nucleotides 4
            through 57 of SEQ ID NO:8 and corresponding codons
            amino Acids 2 through 19 of SEQ ID NO:9."

(ix) FEATURE:
        (A) NAME/KEY: -
        (B) LOCATION: (6^7)
        (D) OTHER INFORMATION: /note= "Representing nucleotides 61
            through 255 of SEQ ID NO:8 and corresponding codons
            amino acids 21-85 of SEQ ID NO:9."

(ix) FEATURE:
        (A) NAME/KEY: -
        (B) LOCATION: (39^40)
        (D) OTHER INFORMATION: /note= "Represents nucleotides 844
            through 2022 of SEQ ID NO:2, including corresponding
            amino acids."

(xi) SEQUENCE DESCRIPTION: SEQ ID NO:19:

```
ATG GCT GAG GCC TTT AGA TCT CGA GTA CCC GGG ACC ATG GGA TAA TAG        48
Met Ala Glu Ala Phe Arg Ser Arg Val Pro Gly Thr Met Gly  *   *
    110             115             120
```

(2) INFORMATION FOR SEQ ID NO:20:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:20:

```
Met Ala Glu Ala Phe Arg Ser Arg Val Pro Gly Thr Met Gly
 1               5                  10
```

(2) INFORMATION FOR SEQ ID NO:21:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..42

(ix) FEATURE:
        (A) NAME/KEY: -
        (B) LOCATION: (3^4)
        (D) OTHER INFORMATION: /note= "Represents nucleotides 4
            through 255 of SEQ ID NO:8 and corresponding codons,
            amino acids 2 through 85 of SEQ ID NO:9."

(ix) FEATURE:
            (A) NAME/KEY: -
            (B) LOCATION: (36^37)
            (D) OTHER INFORMATION: /note= "Represents nucleotides 844
                through 2022 of SEQ ID NO:2, including corresponding
                amino acids."

(xi) SEQUENCE DESCRIPTION: SEQ ID NO:21:

ATG GAG GCC TTT AGA TCT CGA GTA CCC GGG ACC ATG GGA TAA                    42
Met Glu Ala Phe Arg Ser Arg Val Pro Gly Thr Met Gly  *
            20                  25                  30

(2) INFORMATION FOR SEQ ID NO:22:

(i) SEQUENCE CHARACTERISTICS:
            (A) LENGTH: 13 amino acids
            (B) TYPE: amino acid
            (D) TOPOLOGY: linear (ii) MOLECULE TYPE: protein (xi) SEQUENCE DESCRIPTION: SEQ ID NO:22:

Met Glu Ala Phe Arg Ser Arg Val Pro Gly Thr Met Gly
 1               5                  10

(2) INFORMATION FOR SEQ ID NO:23:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ix) FEATURE:
            (A) NAME/KEY: CDS
            (B) LOCATION: 1..39

(ix) FEATURE:
            (A) NAME/KEY: -
            (B) LOCATION: (3^4)
            (D) OTHER INFORMATION: /note= "Represents nucleotides 3
                through 96 of SEQ ID NO:10, including corresponding
                amino acids."

(ix) FEATURE:
            (A) NAME/KEY: -
            (B) LOCATION: (33^34)
            (D) OTHER INFORMATION: /note= "Represents nucleotides 841
                through 2022 of SEQ ID NO:2, including corresponding
                amino acids."

(xi) SEQUENCE DESCRIPTION: SEQ ID NO:23:

ATG GGA GCC AGA TCT CGA GTA CCC GGG ACC ATG GGA TAA                        39
Met Gly Ala Arg Ser Arg Val Pro Gly Thr Met Gly  *
 15              20                  25

(2) INFORMATION FOR SEQ ID NO:24:

(i) SEQUENCE CHARACTERISTICS:
            (A) LENGTH: 12 amino acids
            (B) TYPE: amino acid
            (D) TOPOLOGY: linear (ii) MOLECULE TYPE: protein (xi) SEQUENCE DESCRIPTION: SEQ ID NO:24:

Met Gly Ala Arg Ser Arg Val Pro Gly Thr Met Gly
 1               5                  10

(2) INFORMATION FOR SEQ ID NO:25:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:25:

```
Gly Ala Arg Ser Arg Val Pro Gly Thr
1               5
```

(2) INFORMATION FOR SEQ ID NO:26:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 30..47
        (D) OTHER INFORMATION: /note= "Nucleotides 343 through 360
            of SEQ ID NO:1."

(xi) SEQUENCE DESCRIPTION: SEQ ID NO:26:

ATTCTAGATC TCGAGTACCC GGGACCATGT TTCATCTGAC CACACGC            47

(2) INFORMATION FOR SEQ ID NO:27:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 20..37
        (D) OTHER INFORMATION: /note= "Complementary DNA to
            Nucleotides 2308 through 2325 of SEQ ID NO:1."

(xi) SEQUENCE DESCRIPTION: SEQ ID NO:27:

TCTCTAGAGT CGACTATTAG GCCTGCACCA TAACTCC                      37

(2) INFORMATION FOR SEQ ID NO:28:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..51

(ix) FEATURE:
        (A) NAME/KEY: -
        (B) LOCATION: (3^4)
        (D) OTHER INFORMATION: /note= "Represents nucleotides 4
            through 255 of SEQ ID NO:8 and corresponding codons,
            amino acids 2 through 85 of SEQ ID NO:9."

(ix) FEATURE:
        (A) NAME/KEY: -
        (B) LOCATION: (39^40)
        (D) OTHER INFORMATION: /note= "Represents nucleotides 346
            through 837 of SEQ ID NO:2, including corresponding
            amino acids."

```
    (ix) FEATURE:
         (A) NAME/KEY: -
         (B) LOCATION: (45^46)
         (D) OTHER INFORMATION: /note= "Represents nucleotides 844
             through 2022 of SEQ ID NO:2, including corresponding
             amino acids."

(xi) SEQUENCE DESCRIPTION: SEQ ID NO:28:

ATG GAG GCC TTT AGA TCT CGA GTA CCC GGG ACC ATG TTT ACA ATG GGA         48
Met Glu Ala Phe Arg Ser Arg Val Pro Gly Thr Met Phe Thr Met Gly
    15                  20                  25

TAA                                                                     51
 *
 30

(2) INFORMATION FOR SEQ ID NO:29:

(i) SEQUENCE CHARACTERISTICS:
         (A) LENGTH: 16 amino acids
         (B) TYPE: amino acid
         (D) TOPOLOGY: linear (ii) MOLECULE TYPE: protein (xi) SEQUENCE DESCRIPTION: SEQ ID NO:29:

Met Glu Ala Phe Arg Ser Arg Val Pro Gly Thr Met Phe Thr Met Gly
 1               5                  10                  15

(2) INFORMATION FOR SEQ ID NO:30:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ix) FEATURE:
         (A) NAME/KEY: CDS
         (B) LOCATION: 1..27

(xi) SEQUENCE DESCRIPTION: SEQ ID NO:30:

ATC GCT CCT TCA ATG ACA ATG CGC TGC                                     27
Ile Ala Pro Ser Met Thr Met Arg Cys
        20                  25

(2) INFORMATION FOR SEQ ID NO:31:

(i) SEQUENCE CHARACTERISTICS:
         (A) LENGTH: 9 amino acids
         (B) TYPE: amino acid
         (D) TOPOLOGY: linear (ii) MOLECULE TYPE: protein (xi) SEQUENCE DESCRIPTION: SEQ ID NO:31:

Ile Ala Pro Ser Met Thr Met Arg Cys
 1               5

(2) INFORMATION FOR SEQ ID NO:32:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ix) FEATURE:
         (A) NAME/KEY: CDS
         (B) LOCATION: 1..27
```

```
        (ix) FEATURE:
              (A) NAME/KEY: misc_feature
              (B) LOCATION: 7..21
              (D) OTHER INFORMATION: /note= "Mutagenized region of
                  sequence."

(xi) SEQUENCE DESCRIPTION: SEQ ID NO:32:

ATC GCT GGC GCT CAA GCT CAA CGC TGC                               27
Ile Ala Gly Ala Gln Ala Gln Arg Cys
 10                  15

(2) INFORMATION FOR SEQ ID NO:33:

(i) SEQUENCE CHARACTERISTICS:
              (A) LENGTH: 9 amino acids
              (B) TYPE: amino acid
              (D) TOPOLOGY: linear (ii) MOLECULE TYPE: protein (xi) SEQUENCE DESCRIPTION: SEQ ID NO:33:

Ile Ala Gly Ala Gln Ala Gln Arg Cys
 1                   5

(2) INFORMATION FOR SEQ ID NO:34:

(i) SEQUENCE CHARACTERISTICS:
              (A) LENGTH: 5 amino acids
              (B) TYPE: amino acid
              (C) STRANDEDNESS: single
              (D) TOPOLOGY: linear (xi) SEQUENCE DESCRIPTION: SEQ ID NO:34:

Pro Ser Met Thr Met
 1           5

(2) INFORMATION FOR SEQ ID NO:35:

(i) SEQUENCE CHARACTERISTICS:
              (A) LENGTH: 5 amino acids
              (B) TYPE: amino acid
              (C) STRANDEDNESS: single
              (D) TOPOLOGY: linear (xi) SEQUENCE DESCRIPTION: SEQ ID NO:35:

Gly Ala Gln Ala Gln
 1           5

(2) INFORMATION FOR SEQ ID NO:36:

(i) SEQUENCE CHARACTERISTICS:
              (A) LENGTH: 15 base pairs
              (B) TYPE: nucleic acid
              (C) STRANDEDNESS: single
              (D) TOPOLOGY: linear (xi) SEQUENCE DESCRIPTION: SEQ ID NO:36:

TCGAGAAGAG AGAAG                                                  15

(2) INFORMATION FOR SEQ ID NO:37:

(i) SEQUENCE CHARACTERISTICS:
              (A) LENGTH: 15 base pairs
              (B) TYPE: nucleic acid
              (C) STRANDEDNESS: single
              (D) TOPOLOGY: linear
```

```
       (xi) SEQUENCE DESCRIPTION: SEQ ID NO:37:

CCGGCTTCTC TCTTC                                                          15

(2) INFORMATION FOR SEQ ID NO:38:

(i) SEQUENCE CHARACTERISTICS:
           (A) LENGTH: 51 base pairs
           (B) TYPE: nucleic acid
           (C) STRANDEDNESS: single
           (D) TOPOLOGY: linear (ix) FEATURE:
           (A) NAME/KEY: CDS
           (B) LOCATION: 1..51

(ix) FEATURE:
           (A) NAME/KEY: -
           (B) LOCATION: (3^4)
           (D) OTHER INFORMATION: /note= "Represents nucleotides 4
                through 243 of SEQ ID NO:8 and corresponding codons,
                amino acids 2 through 81 of SEQ ID NO:9."

(xi) SEQUENCE DESCRIPTION: SEQ ID NO:38:

ATG CTC GAG AAA AGG GAG GCC TTT AGA TCT CGA GTA CCC GGG ACC ATG       48
Met Leu Glu Lys Arg Glu Ala Phe Arg Ser Arg Val Pro Gly Thr Met
 10                  15                  20                  25

TTT                                                                   51
Phe (2) INFORMATION FOR SEQ ID NO:39:

(i) SEQUENCE CHARACTERISTICS:
           (A) LENGTH: 17 amino acids
           (B) TYPE: amino acid
           (D) TOPOLOGY: linear (ii) MOLECULE TYPE: protein (xi) SEQUENCE DESCRIPTION: SEQ ID NO:39:

Met Leu Glu Lys Arg Glu Ala Phe Arg Ser Arg Val Pro Gly Thr Met
 1               5                  10                  15

Phe (2) INFORMATION FOR SEQ ID NO:40:

(i) SEQUENCE CHARACTERISTICS:
           (A) LENGTH: 33 base pairs
           (B) TYPE: nucleic acid
           (C) STRANDEDNESS: single
           (D) TOPOLOGY: linear (ix) FEATURE:
           (A) NAME/KEY: CDS
           (B) LOCATION: 1..33

(ix) FEATURE:
           (A) NAME/KEY: -
           (B) LOCATION: (3^4)
           (D) OTHER INFORMATION: /note= "Represents nucleotides 4
                through 243 of SEQ ID NO:8 and corresponding codons,
                amino acids 2 through 81 of SEQ ID NO:9."

(xi) SEQUENCE DESCRIPTION: SEQ ID NO:40:

ATG CTC GAG AAA AGG GAG GCC GGG ACC ATG TTT                           33
Met Leu Glu Lys Arg Glu Ala Gly Thr Met Phe
         20                  25
```

(2) INFORMATION FOR SEQ ID NO:41:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:41:

```
Met Leu Glu Lys Arg Glu Ala Gly Thr Met Phe
 1               5                  10
```

(2) INFORMATION FOR SEQ ID NO:42:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..48

(ix) FEATURE:
        (A) NAME/KEY: -
        (B) LOCATION: (3^4)
        (D) OTHER INFORMATION: /note= "Represents nucleotides 3
            through 96 of SEQ ID NO:10, including corresponding
            amino acids."

(ix) FEATURE:
        (A) NAME/KEY: -
        (B) LOCATION: (36^37)
        (D) OTHER INFORMATION: /note= "Represents nucleotides 346
            through 837 of SEQ ID NO:2, including corresponding
            amino acids."

(ix) FEATURE:
        (A) NAME/KEY: -
        (B) LOCATION: (42^43)
        (D) OTHER INFORMATION: /note= "Represents nucleotides 844
            through 2022 of SEQ ID NO:2, including corresponding
            amino acids."

(xi) SEQUENCE DESCRIPTION: SEQ ID NO:42:

```
ATG GGA GCC AGA TCT CGA GTA CCC GGG ACC ATG TTT ACA ATG GGA TAA     48
Met Gly Ala Arg Ser Arg Val Pro Gly Thr Met Phe Thr Met Gly  *
            15                  20                  25
```

(2) INFORMATION FOR SEQ ID NO:43:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:43:

```
Met Gly Ala Arg Ser Arg Val Pro Gly Thr Met Phe Thr Met Gly
 1               5                  10                  15
```

(2) INFORMATION FOR SEQ ID NO:44:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:44:

Met Xaa Xaa Ile Gly Ile
1               5

(2) INFORMATION FOR SEQ ID NO:45:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:45:

Val Xaa Val Gly Ala Val
1               5

(2) INFORMATION FOR SEQ ID NO:46:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:46:

Met Arg Cys Ile Gly Ile
1               5

(2) INFORMATION FOR SEQ ID NO:47:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..48

(ix) FEATURE:
        (A) NAME/KEY: -
        (B) LOCATION: (3^4)
        (D) OTHER INFORMATION: /note= "Represents nucleotides 4
            through 57 of SEQ ID NO:8 and corresponding codons,
            amino acids 2 through 19 of SEQ ID NO:9."

(ix) FEATURE:
        (A) NAME/KEY: -
        (B) LOCATION: (6^7)
        (D) OTHER INFORMATION: /note= "Represents nucleotides 61
            through 255 of SEQ ID NO:8 and corresponding codons,
            amino acids 21 through 85 of SEQ ID NO:9."

(ix) FEATURE:
        (A) NAME/KEY: -
        (B) LOCATION: (39^40)
        (D) OTHER INFORMATION: /note= "Represents nucleotides 844
            through 1710 of SEQ ID NO:2, including corresponding
            amino acids."

(xi) SEQUENCE DESCRIPTION: SEQ ID NO:47:

ATG GCT GAG GCC TTT AGA TCT CGA GTA CCC GGG ACC ATG AAA TAA TAG      48
Met Ala Glu Ala Phe Arg Ser Arg Val Pro Gly Thr Met Lys  *   *
                 20              25              30

(2) INFORMATION FOR SEQ ID NO:48:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:48:

Met Ala Glu Ala Phe Arg Ser Arg Val Pro Gly Thr Met Lys
 1               5                  10

(2) INFORMATION FOR SEQ ID NO:49:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..24

(ix) FEATURE:
        (A) NAME/KEY: -
        (B) LOCATION: (3^4)
        (D) OTHER INFORMATION: /note= "Represents nucleotides 4
            through 255 of SEQ ID NO:8 and corresponding codons,
            amino acids 2 through 85 of SEQ ID NO:9."

(ix) FEATURE:
        (A) NAME/KEY: -
        (B) LOCATION: (18^19)
        (D) OTHER INFORMATION: /note= "Represents nucleotides 844
            through 1710 of SEQ ID NO:2, including corresponding
            amino acids."

(xi) SEQUENCE DESCRIPTION: SEQ ID NO:49:

ATG GAG GCC GGG ACC ATG AAA TAA                                    24
Met Glu Ala Gly Thr Met Lys  *
                       20

(2) INFORMATION FOR SEQ ID NO:50:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:50:

Met Glu Ala Gly Thr Met Lys
 1               5

(2) INFORMATION FOR SEQ ID NO:51:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..48

(ix) FEATURE:
        (A) NAME/KEY: -
        (B) LOCATION: (3^4)
        (D) OTHER INFORMATION: /note= "Represents nucleotides 3

-continued

```
              through 96 of SEQ ID NO:10, including corresponding
              amino acids."

(ix) FEATURE:
         (A) NAME/KEY: -
         (B) LOCATION: (36^37)
         (D) OTHER INFORMATION: /note= "Represents nucleotides 346
              through 837 of SEQ ID NO:2, including corresponding
              amino acids."

(ix) FEATURE:
         (A) NAME/KEY: -
         (B) LOCATION: (42^43)
         (D) OTHER INFORMATION: /note= "Represents nucleotides 844
              through 2322 of SEQ ID NO:2, including corresponding
              amino acids."

(xi) SEQUENCE DESCRIPTION: SEQ ID NO:51:

ATG GGA GCC AGA TCT CGA GTA CCC GGG ACC ATG TTT ACA ATG GCC TAA       48
Met Gly Ala Arg Ser Arg Val Pro Gly Thr Met Phe Thr Met Ala  *
     10                  15                  20

(2) INFORMATION FOR SEQ ID NO:52:

(i) SEQUENCE CHARACTERISTICS:
         (A) LENGTH: 15 amino acids
         (B) TYPE: amino acid
         (D) TOPOLOGY: linear (ii) MOLECULE TYPE: protein (xi) SEQUENCE DESCRIPTION: SEQ ID NO:52:

Met Gly Ala Arg Ser Arg Val Pro Gly Thr Met Phe Thr Met Ala
  1               5                  10                  15
```